US008852239B2

(12) United States Patent
Jackson et al.

(10) Patent No.: US 8,852,239 B2
(45) Date of Patent: Oct. 7, 2014

(54) SAGITTAL ANGLE SCREW WITH INTEGRAL SHANK AND RECEIVER

(71) Applicants: Roger P Jackson, Prairie Village, KS (US); James L Surber, Kansas City, KS (US)

(72) Inventors: Roger P Jackson, Prairie Village, KS (US); James L Surber, Kansas City, KS (US)

( * ) Notice: Subject to any disclaimer, the term of this patent is extended or adjusted under 35 U.S.C. 154(b) by 0 days.

(21) Appl. No.: 14/181,998

(22) Filed: Feb. 17, 2014

(65) Prior Publication Data

US 2014/0236235 A1 Aug. 21, 2014

Related U.S. Application Data

(60) Provisional application No. 61/850,500, filed on Feb. 15, 2013.

(51) Int. Cl.
*A61B 17/70* (2006.01)
*A61B 17/86* (2006.01)

(52) U.S. Cl.
CPC ......... *A61B 17/7035* (2013.01); *A61B 17/7037* (2013.01); *A61B 17/7091* (2013.01); *A61B 17/7032* (2013.01)
USPC ............................ 606/267; 606/270; 606/306

(58) Field of Classification Search
CPC ........... A61B 17/7032; A61B 17/7035; A61B 17/7091; A61B 17/7037; A61B 17/7005; A61B 17/7007; A61B 17/86; A61B 17/7008; A61B 17/7004; A61B 17/7083; A61B 17/7025; A61B 17/8685; A61B 17/1671; A61B 17/1757; A61B 17/702; A61B 17/7023; A61B 2017/0256

USPC ......... 606/301–308, 264–272, 246, 257, 251, 606/253, 278, 287, 328
See application file for complete search history.

(56) References Cited

U.S. PATENT DOCUMENTS

| 154,864 A | 9/1874 | Harvey |
| 791,548 A | 6/1905 | Fischer |
| 1,300,275 A | 4/1919 | Johnson |
| 1,330,673 A | 2/1920 | Anderson |
| 1,472,464 A | 10/1923 | Ellison |
| 2,083,092 A | 6/1937 | Richer |
| 2,201,087 A | 5/1940 | Hallowell |
| 2,239,352 A | 4/1941 | Cherry |
| 2,243,717 A | 5/1941 | Moreira |

(Continued)

FOREIGN PATENT DOCUMENTS

| AU | 2012203959 | 8/2012 |
| DE | 373809 | 4/1923 |

(Continued)

OTHER PUBLICATIONS

Brochure of Tyco/Healthcare/Surgical Dynamics on Spiral Radius 90D, Publication Date: Sep. 2001, pp. 1-8.

(Continued)

*Primary Examiner* — Pedro Philogene
(74) *Attorney, Agent, or Firm* — John C. McMahon

(57) ABSTRACT

A spinal bone screw has a receiver with upstanding arms forming a channel for receiving a longitudinal connecting member, such as a rod, the receiver being integral with a threaded shank. The receiver further includes inner surfaces in sliding engagement with an insert, the insert having a seating surface for the rod. The insert and rod being pivotable with respect to the bone screw in a single plane.

29 Claims, 14 Drawing Sheets

(56) References Cited

U.S. PATENT DOCUMENTS

| | | |
|---|---|---|
| 2,295,314 A | 9/1942 | Whitney |
| 2,346,346 A | 4/1944 | Anderson |
| 2,362,999 A | 11/1944 | Elmer |
| 2,445,978 A | 7/1948 | Stellin |
| 2,531,892 A | 11/1950 | Reese |
| 2,532,815 A | 12/1950 | Kindsvatter et al. |
| 2,537,029 A | 1/1951 | Cambern |
| 2,553,337 A | 5/1951 | Shafer |
| 2,778,265 A | 1/1957 | Brown |
| 2,813,450 A | 11/1957 | Dzus |
| 2,877,681 A | 3/1959 | Brown |
| 2,927,332 A | 3/1960 | Moore |
| 2,969,250 A | 1/1961 | Kull |
| 3,013,244 A | 12/1961 | Rudy |
| 3,143,029 A | 8/1964 | Brown |
| D200,217 S | 2/1965 | Curtiss |
| 3,236,275 A | 2/1966 | Smith |
| 3,370,341 A | 2/1968 | Allsop |
| 3,444,775 A | 5/1969 | Hills |
| 3,498,174 A | 3/1970 | Schuster et al. |
| 3,584,667 A | 6/1971 | Reiland |
| 3,604,487 A | 9/1971 | Gilbert |
| 3,640,416 A | 2/1972 | Temple |
| 3,812,757 A | 5/1974 | Reiland |
| 3,963,322 A | 6/1976 | Gryctko |
| 3,989,284 A | 11/1976 | Blose |
| 3,997,138 A | 12/1976 | Crock et al. |
| 4,013,071 A | 3/1977 | Rosenberg |
| 4,033,139 A | 7/1977 | Frederick |
| 4,041,939 A | 8/1977 | Hall |
| 4,103,422 A | 8/1978 | Weiss et al. |
| 4,190,091 A | 2/1980 | Colognori |
| 4,269,246 A | 5/1981 | Larson et al. |
| 4,347,845 A | 9/1982 | Mayfield |
| 4,369,769 A | 1/1983 | Edwards |
| 4,373,754 A | 2/1983 | Bollfrass et al. |
| 4,409,968 A | 10/1983 | Drummond |
| 4,448,191 A | 5/1984 | Rodnyansky et al. |
| 4,484,570 A | 11/1984 | Sutter et al. |
| 4,492,500 A | 1/1985 | Ewing |
| 4,506,917 A | 3/1985 | Hansen |
| 4,577,448 A | 3/1986 | Howorth |
| 4,600,224 A | 7/1986 | Blose |
| 4,600,225 A | 7/1986 | Blose |
| 4,641,636 A | 2/1987 | Cotrel |
| 4,653,481 A | 3/1987 | Howland et al. |
| 4,653,486 A | 3/1987 | Coker |
| 4,703,954 A | 11/1987 | Ortloff et al. |
| 4,707,001 A | 11/1987 | Johnson |
| 4,743,260 A | 5/1988 | Burton |
| 4,748,260 A | 5/1988 | Marlett |
| 4,759,672 A | 7/1988 | Nilsen et al. |
| 4,763,644 A | 8/1988 | Webb |
| 4,764,068 A | 8/1988 | Crispell |
| 4,790,297 A | 12/1988 | Luque |
| 4,805,602 A | 2/1989 | Puno et al. |
| 4,815,453 A | 3/1989 | Cotrel |
| 4,836,196 A | 6/1989 | Park et al. |
| 4,838,264 A | 6/1989 | Bremer et al. |
| 4,850,775 A | 7/1989 | Lee et al. |
| 4,877,020 A | 10/1989 | Vich |
| 4,887,596 A | 12/1989 | Sherman |
| 4,917,606 A | 4/1990 | Miller |
| 4,946,458 A | 8/1990 | Harms et al. |
| 4,950,269 A | 8/1990 | Gaines, Jr. |
| 4,961,740 A | 10/1990 | Ray et al. |
| 5,005,562 A | 4/1991 | Cotrel |
| 5,019,080 A | 5/1991 | Hemer |
| 5,022,791 A | 6/1991 | Isler |
| 5,034,011 A | 7/1991 | Howland |
| 5,042,982 A | 8/1991 | Harms et al. |
| 5,056,492 A | 10/1991 | Banse |
| 5,067,428 A | 11/1991 | Dickerson et al. |
| 5,067,955 A | 11/1991 | Cotrel |
| 5,073,074 A | 12/1991 | Corrigan et al. |
| 5,084,048 A | 1/1992 | Jacob et al. |
| 5,092,635 A | 3/1992 | DeLange et al. |
| 5,102,412 A | 4/1992 | Rogozinski |
| 5,129,388 A | 7/1992 | Vignaud et al. |
| 5,129,899 A | 7/1992 | Small et al. |
| 5,147,360 A | 9/1992 | Dubousset |
| 5,147,363 A | 9/1992 | Harle |
| 5,154,719 A | 10/1992 | Cotrel |
| 5,176,483 A | 1/1993 | Baumann et al. |
| 5,176,678 A | 1/1993 | Tsou |
| 5,176,679 A | 1/1993 | Lin |
| 5,176,680 A | 1/1993 | Vignaud et al. |
| 5,180,393 A | 1/1993 | Commarmond |
| 5,201,734 A | 4/1993 | Cozad et al. |
| 5,207,678 A | 5/1993 | Harms et al. |
| 5,217,497 A | 6/1993 | Mehdian |
| 5,257,993 A | 11/1993 | Asher et al. |
| 5,261,907 A | 11/1993 | Vignaud et al. |
| 5,263,953 A | 11/1993 | Bagby |
| 5,275,601 A | 1/1994 | Gogolewski et al. |
| 5,282,707 A | 2/1994 | Palm |
| 5,282,862 A | 2/1994 | Baker et al. |
| 5,282,863 A | 2/1994 | Burton |
| 5,306,275 A | 4/1994 | Bryan |
| 5,312,404 A | 5/1994 | Asher et al. |
| 5,321,901 A | 6/1994 | Kelly |
| 5,330,472 A | 7/1994 | Metz-Stavenhagen |
| 5,334,203 A | 8/1994 | Wagner |
| 5,346,493 A | 9/1994 | Stahurski et al. |
| 5,354,292 A | 10/1994 | Braeuer et al. |
| 5,354,299 A | 10/1994 | Coleman |
| 5,358,289 A | 10/1994 | Banker et al. |
| 5,360,431 A | 11/1994 | Puno et al. |
| 5,364,400 A | 11/1994 | Rego, Jr. et al. |
| 5,375,823 A | 12/1994 | Navas |
| 5,382,248 A | 1/1995 | Jacobson et al. |
| 5,385,583 A | 1/1995 | Cotrel |
| 5,387,211 A | 2/1995 | Saadatmanesh et al. |
| 5,387,212 A | 2/1995 | Yuan et al. |
| 5,395,371 A | 3/1995 | Miller et al. |
| 5,409,488 A | 4/1995 | Ulrich |
| 5,409,489 A | 4/1995 | Sioufi |
| 5,415,661 A | 5/1995 | Holmes |
| 5,423,816 A | 6/1995 | Lin |
| 5,427,418 A | 6/1995 | Watts |
| 5,429,639 A | 7/1995 | Judet |
| 5,434,001 A | 7/1995 | Yamada et al. |
| 5,443,467 A | 8/1995 | Biedermann et al. |
| 5,466,237 A | 11/1995 | Byrd, III et al. |
| 5,466,238 A | 11/1995 | Lin |
| 5,468,241 A | 11/1995 | Metz-Stavenhagen et al. |
| 5,474,551 A | 12/1995 | Finn et al. |
| 5,474,555 A | 12/1995 | Puno et al. |
| 5,476,462 A | 12/1995 | Allard et al. |
| 5,476,464 A | 12/1995 | Metz-Stavenhagen et al. |
| 5,480,401 A | 1/1996 | Navas |
| 5,484,440 A | 1/1996 | Allard |
| 5,487,742 A | 1/1996 | Cotrel |
| 5,489,307 A | 2/1996 | Kuslich et al. |
| 5,490,750 A | 2/1996 | Gundy |
| 5,499,892 A | 3/1996 | Reed |
| 5,501,684 A | 3/1996 | Schlapfer et al. |
| 5,505,731 A | 4/1996 | Tornier |
| 5,507,745 A | 4/1996 | Logroscino et al. |
| 5,507,747 A | 4/1996 | Yuan et al. |
| 5,534,001 A | 7/1996 | Schlapfer et al. |
| 5,540,688 A | 7/1996 | Navas |
| 5,545,165 A | 8/1996 | Biedermann et al. |
| 5,549,607 A | 8/1996 | Olson et al. |
| 5,549,608 A | 8/1996 | Errico et al. |
| 5,554,157 A | 9/1996 | Errico et al. |
| 5,562,660 A | 10/1996 | Grob |
| 5,562,663 A | 10/1996 | Wisnewski et al. |
| 5,569,247 A | 10/1996 | Morrison |
| 5,569,251 A | 10/1996 | Baker et al. |
| 5,578,033 A | 11/1996 | Errico et al. |
| 5,584,834 A | 12/1996 | Errico et al. |
| 5,586,984 A | 12/1996 | Errico et al. |
| 5,591,166 A | 1/1997 | Bernhardt et al. |

(56) References Cited

U.S. PATENT DOCUMENTS

| | | |
|---|---|---|
| 5,601,553 A | 2/1997 | Trebing et al. |
| 5,605,458 A | 2/1997 | Bailey et al. |
| 5,607,304 A | 3/1997 | Bailey et al. |
| 5,607,425 A | 3/1997 | Rogozinski |
| 5,607,426 A | 3/1997 | Ralph et al. |
| 5,607,428 A | 3/1997 | Lin |
| 5,609,593 A | 3/1997 | Errico et al. |
| 5,609,594 A | 3/1997 | Errico et al. |
| 5,611,800 A | 3/1997 | Davis et al. |
| 5,628,740 A | 5/1997 | Mullane |
| 5,630,817 A | 5/1997 | Rokegem |
| 5,641,256 A | 6/1997 | Gundy |
| 5,643,260 A | 7/1997 | Doherty |
| 5,643,261 A | 7/1997 | Schafer et al. |
| 5,647,873 A | 7/1997 | Errico et al. |
| 5,653,710 A | 8/1997 | Harle |
| 5,662,652 A | 9/1997 | Schafer et al. |
| 5,662,653 A | 9/1997 | Songer et al. |
| 5,667,508 A | 9/1997 | Errico et al. |
| 5,669,909 A | 9/1997 | Zdeblick et al. |
| 5,669,911 A | 9/1997 | Errico et al. |
| 5,672,175 A | 9/1997 | Martin |
| 5,672,176 A | 9/1997 | Biedermann |
| 5,676,665 A | 10/1997 | Bryan |
| 5,676,703 A | 10/1997 | Gelbard |
| 5,681,319 A | 10/1997 | Biedermann et al. |
| 5,683,390 A | 11/1997 | Metz-Stavenhagen et al. |
| 5,683,391 A | 11/1997 | Boyd |
| 5,690,630 A | 11/1997 | Errico et al. |
| 5,702,393 A | 12/1997 | Pfaifer |
| 5,711,709 A | 1/1998 | McCoy |
| 5,713,705 A | 2/1998 | Grunbichler |
| 5,713,898 A | 2/1998 | Stucker et al. |
| 5,716,356 A | 2/1998 | Biedermann et al. |
| 5,720,751 A | 2/1998 | Jackson |
| 5,723,013 A | 3/1998 | Jeanson et al. |
| 5,725,527 A | 3/1998 | Biedermann et al. |
| 5,725,528 A | 3/1998 | Errico et al. |
| 5,728,098 A | 3/1998 | Sherman et al. |
| 5,733,286 A | 3/1998 | Errico et al. |
| 5,738,685 A | 4/1998 | Halm et al. |
| 5,741,254 A | 4/1998 | Henry et al. |
| 5,752,957 A | 5/1998 | Ralph et al. |
| 5,782,833 A | 7/1998 | Haider |
| 5,797,911 A | 8/1998 | Sherman et al. |
| 5,800,435 A | 9/1998 | Errico et al. |
| 5,800,547 A | 9/1998 | Schafer et al. |
| 5,817,094 A | 10/1998 | Errico et al. |
| 5,863,293 A | 1/1999 | Richelsoph |
| 5,873,878 A | 2/1999 | Harms et al. |
| D407,302 S | 3/1999 | Lawson |
| 5,876,402 A | 3/1999 | Errico et al. |
| 5,879,351 A | 3/1999 | Viart |
| 5,882,350 A | 3/1999 | Ralph et al. |
| 5,902,303 A | 5/1999 | Eckhof et al. |
| RE36,221 E | 6/1999 | Breard et al. |
| 5,910,141 A | 6/1999 | Morrison et al. |
| 5,910,142 A | 6/1999 | Tatar |
| 5,928,236 A | 7/1999 | Augagneur et al. |
| 5,938,663 A | 8/1999 | Petreto |
| 5,941,880 A | 8/1999 | Errico et al. |
| 5,944,465 A | 8/1999 | Janitzki |
| 5,951,553 A | 9/1999 | Betz et al. |
| 5,961,517 A | 10/1999 | Biedermann et al. |
| 5,964,760 A | 10/1999 | Richelsoph |
| 5,964,767 A | 10/1999 | Tapia et al. |
| 5,997,539 A | 12/1999 | Errico et al. |
| 6,001,098 A | 12/1999 | Metz-Stavenhagen et al. |
| 6,004,349 A | 12/1999 | Jackson |
| 6,010,503 A | 1/2000 | Richelsoph et al. |
| 6,019,759 A | 2/2000 | Rogozinski |
| 6,022,350 A | 2/2000 | Ganem |
| 6,053,078 A | 4/2000 | Parker |
| 6,056,753 A | 5/2000 | Jackson |
| 6,063,088 A | 5/2000 | Winslow |
| 6,074,391 A | 6/2000 | Metz-Stavenhagen et al. |
| 6,077,262 A | 6/2000 | Schlapfer et al. |
| 6,086,588 A | 7/2000 | Ameil et al. |
| 6,090,110 A | 7/2000 | Metz-Stavenhagen |
| 6,090,111 A | 7/2000 | Nichols |
| 6,099,528 A | 8/2000 | Saurat |
| 6,110,172 A | 8/2000 | Jackson |
| 6,113,601 A | 9/2000 | Tatar |
| 6,117,137 A | 9/2000 | Halm et al. |
| 6,129,763 A | 10/2000 | Chauvin et al. |
| 6,132,431 A | 10/2000 | Nilsson et al. |
| 6,136,002 A | 10/2000 | Shih et al. |
| 6,136,003 A | 10/2000 | Hoeck et al. |
| 6,143,032 A | 11/2000 | Schafer et al. |
| 6,146,383 A | 11/2000 | Studer et al. |
| 6,149,533 A | 11/2000 | Finn |
| 6,162,223 A | 12/2000 | Orsak et al. |
| 6,168,597 B1 | 1/2001 | Biedermann et al. |
| 6,183,472 B1 | 2/2001 | Lutz |
| 6,186,718 B1 | 2/2001 | Fogard |
| 6,193,719 B1 | 2/2001 | Gournay et al. |
| 6,193,720 B1 | 2/2001 | Yuan et al. |
| 6,214,012 B1 | 4/2001 | Karpman et al. |
| RE37,161 E | 5/2001 | Michelson et al. |
| 6,224,596 B1 | 5/2001 | Jackson |
| 6,224,598 B1 | 5/2001 | Jackson |
| 6,235,028 B1 | 5/2001 | Brumfield et al. |
| 6,235,034 B1 | 5/2001 | Bray |
| 6,241,730 B1 | 6/2001 | Alby |
| 6,241,731 B1 | 6/2001 | Fiz |
| 6,248,105 B1 | 6/2001 | Schlapfer et al. |
| 6,248,107 B1 | 6/2001 | Foley et al. |
| 6,251,112 B1 | 6/2001 | Jackson |
| 6,254,602 B1 | 7/2001 | Justis |
| 6,261,039 B1 | 7/2001 | Reed |
| 6,267,764 B1 | 7/2001 | Elberg |
| 6,267,765 B1 | 7/2001 | Taylor et al. |
| 6,280,445 B1 | 8/2001 | Morrison et al. |
| 6,287,308 B1 | 9/2001 | Betz et al. |
| 6,296,643 B1 | 10/2001 | Hopf et al. |
| 6,299,613 B1 | 10/2001 | Ogilvie et al. |
| 6,299,616 B1 | 10/2001 | Beger |
| 6,302,888 B1 | 10/2001 | Mellinger et al. |
| 6,309,391 B1 | 10/2001 | Crandall et al. |
| 6,315,564 B1 | 11/2001 | Levisman |
| 6,322,108 B1 | 11/2001 | Riesselmann et al. |
| RE37,665 E | 4/2002 | Ralph et al. |
| 6,368,321 B1 | 4/2002 | Jackson |
| 6,379,356 B1 | 4/2002 | Jackson |
| 6,402,757 B1 | 6/2002 | Moore et al. |
| 6,440,133 B1 | 8/2002 | Beale et al. |
| 6,443,956 B1 | 9/2002 | Ray |
| 6,467,958 B1 | 10/2002 | Sasaki et al. |
| 6,471,703 B1 | 10/2002 | Ashman |
| 6,478,797 B1 | 11/2002 | Paul |
| 6,478,798 B1 | 11/2002 | Howland |
| 6,485,491 B1 | 11/2002 | Farris et al. |
| 6,485,492 B1 | 11/2002 | Halm et al. |
| 6,485,494 B1 | 11/2002 | Haider |
| 6,520,962 B1 | 2/2003 | Taylor et al. |
| 6,527,804 B1 | 3/2003 | Gauchet et al. |
| 6,533,786 B1 | 3/2003 | Needham et al. |
| 6,554,831 B1 | 4/2003 | Rivard et al. |
| 6,554,834 B1 | 4/2003 | Crozet et al. |
| 6,562,040 B1 | 5/2003 | Wagner |
| 6,565,565 B1 | 5/2003 | Yuan et al. |
| 6,565,567 B1 | 5/2003 | Haider |
| 6,595,992 B1 | 7/2003 | Wagner et al. |
| 6,602,255 B1 | 8/2003 | Campbell et al. |
| 6,613,050 B1 | 9/2003 | Wagner et al. |
| 6,616,667 B1 | 9/2003 | Steiger et al. |
| 6,648,885 B1 | 11/2003 | Friesem |
| 6,648,888 B1 | 11/2003 | Shluzas |
| 6,652,526 B1 | 11/2003 | Arafiles |
| 6,652,765 B1 | 11/2003 | Beaty |
| 6,656,179 B1 | 12/2003 | Schaefer et al. |
| 6,663,632 B1 | 12/2003 | Frigg |
| 6,673,073 B1 | 1/2004 | Schaefer |
| 6,676,661 B1 | 1/2004 | Benlloch et al. |

(56) References Cited

U.S. PATENT DOCUMENTS

| | | |
|---|---|---|
| 6,712,818 B1 | 3/2004 | Michelson |
| 6,716,214 B1 | 4/2004 | Jackson |
| 6,743,231 B1 | 6/2004 | Gray et al. |
| 6,755,829 B1 | 6/2004 | Bono et al. |
| 6,778,861 B1 | 8/2004 | Liebrecht et al. |
| 6,872,208 B1 | 3/2005 | McBride et al. |
| 6,896,677 B1 | 5/2005 | Lin |
| 7,001,389 B1 | 2/2006 | Navarro et al. |
| RE39,035 E | 3/2006 | Finn et al. |
| RE39,089 E | 5/2006 | Ralph et al. |
| 7,081,116 B1 | 7/2006 | Carly |
| 7,316,684 B1 | 1/2008 | Baccelli et al. |
| 7,686,833 B1 | 3/2010 | Muhanna et al. |
| 7,766,943 B1 | 8/2010 | Fallin et al. |
| 7,833,251 B1 | 11/2010 | Ahlgren et al. |
| 7,901,436 B2 * | 3/2011 | Baccelli ............ 606/272 |
| 8,043,340 B1 | 10/2011 | Law |
| 8,048,124 B2 * | 11/2011 | Chin et al. ............ 606/264 |
| 8,092,499 B1 | 1/2012 | Roth |
| 8,167,914 B1 | 5/2012 | Hunt et al. |
| 8,197,517 B1 | 6/2012 | Lab et al. |
| 8,211,110 B1 | 7/2012 | Corin et al. |
| 8,236,035 B1 | 8/2012 | Bedor |
| 8,388,659 B1 | 3/2013 | Lab et al. |
| 8,439,924 B1 | 5/2013 | McBride et al. |
| 8,470,009 B1 | 6/2013 | Rezach |
| 2001/0007941 A1 | 7/2001 | Steiner et al. |
| 2001/0010000 A1 | 7/2001 | Gertzbein et al. |
| 2001/0011172 A1 | 8/2001 | Orbay et al. |
| 2001/0012937 A1 | 8/2001 | Schaffler-Wachter et al. |
| 2001/0023350 A1 | 9/2001 | Choi |
| 2001/0037111 A1 | 11/2001 | Dixon et al. |
| 2001/0041894 A1 | 11/2001 | Campbell et al. |
| 2001/0047173 A1 | 11/2001 | Schlapfer et al. |
| 2001/0047174 A1 | 11/2001 | Donno et al. |
| 2001/0047175 A1 | 11/2001 | Doubler et al. |
| 2001/0052438 A1 | 12/2001 | Spencer |
| 2002/0004683 A1 | 1/2002 | Michelson |
| 2002/0007184 A1 | 1/2002 | Ogilvie et al. |
| 2002/0010467 A1 | 1/2002 | Cooper et al. |
| 2002/0013586 A1 | 1/2002 | Justis et al. |
| 2002/0016594 A1 | 2/2002 | Schlapfer et al. |
| 2002/0022764 A1 | 2/2002 | Smith et al. |
| 2002/0022842 A1 | 2/2002 | Horvath et al. |
| 2002/0029040 A1 | 3/2002 | Morrison et al. |
| 2002/0035365 A1 | 3/2002 | Kumar et al. |
| 2002/0035366 A1 | 3/2002 | Walder et al. |
| 2002/0035367 A1 | 3/2002 | Ritland |
| 2002/0045898 A1 | 4/2002 | Freid et al. |
| 2002/0045899 A1 | 4/2002 | Errico et al. |
| 2002/0049446 A1 | 4/2002 | Harkey, III et al. |
| 2002/0055740 A1 | 5/2002 | Lieberman |
| 2002/0055741 A1 | 5/2002 | Schlapfer et al. |
| 2002/0058942 A1 | 5/2002 | Biedermann et al. |
| 2002/0068975 A1 | 6/2002 | Teitelbaum et al. |
| 2002/0072750 A1 | 6/2002 | Jackson |
| 2002/0072751 A1 | 6/2002 | Jackson |
| 2002/0082602 A1 | 6/2002 | Biedermann et al. |
| 2002/0082603 A1 | 6/2002 | Dixon et al. |
| 2002/0087159 A1 | 7/2002 | Thomas |
| 2002/0087161 A1 | 7/2002 | Randall et al. |
| 2002/0091386 A1 | 7/2002 | Martin et al. |
| 2002/0095153 A1 | 7/2002 | Jones et al. |
| 2002/0095154 A1 | 7/2002 | Atkinson et al. |
| 2002/0095881 A1 | 7/2002 | Shreiner |
| 2002/0103487 A1 | 8/2002 | Errico et al. |
| 2002/0111627 A1 | 8/2002 | Vincent-Prestigiacomo |
| 2002/0116001 A1 | 8/2002 | Schafer et al. |
| 2002/0120270 A1 | 8/2002 | Trieu et al. |
| 2002/0123752 A1 | 9/2002 | Schultheiss et al. |
| 2002/0133154 A1 | 9/2002 | Saint Martin |
| 2002/0133158 A1 | 9/2002 | Saint Martin |
| 2002/0133159 A1 | 9/2002 | Jackson |
| 2002/0138076 A1 | 9/2002 | Biedermann et al. |
| 2002/0138077 A1 | 9/2002 | Ferree |
| 2002/0143328 A1 | 10/2002 | Shluzas et al. |
| 2002/0143330 A1 | 10/2002 | Shluzas |
| 2002/0143332 A1 | 10/2002 | Lin et al. |
| 2002/0143338 A1 | 10/2002 | Orbay et al. |
| 2002/0143341 A1 | 10/2002 | Biedermann et al. |
| 2002/0161368 A1 | 10/2002 | Foley et al. |
| 2002/0161370 A1 | 10/2002 | Frigg et al. |
| 2002/0173791 A1 | 11/2002 | Howland |
| 2002/0183747 A1 | 12/2002 | Jao et al. |
| 2002/0198526 A1 | 12/2002 | Shaolian et al. |
| 2003/0004519 A1 | 1/2003 | Torode et al. |
| 2003/0023243 A1 | 1/2003 | Biedermann et al. |
| 2003/0028191 A1 | 2/2003 | Shluzas |
| 2003/0032957 A1 | 2/2003 | McKinley |
| 2003/0055426 A1 | 3/2003 | Carbone et al. |
| 2003/0055427 A1 | 3/2003 | Graf |
| 2003/0060826 A1 | 3/2003 | Foley et al. |
| 2003/0073995 A1 | 4/2003 | Reed |
| 2003/0073996 A1 | 4/2003 | Doubler et al. |
| 2003/0073998 A1 | 4/2003 | Pagliuca et al. |
| 2003/0078580 A1 | 4/2003 | Shitoto |
| 2003/0083657 A1 | 5/2003 | Drewry et al. |
| 2003/0083667 A1 | 5/2003 | Ralph et al. |
| 2003/0093077 A1 | 5/2003 | Schlapfer et al. |
| 2003/0093078 A1 | 5/2003 | Ritland |
| 2003/0100896 A1 | 5/2003 | Biedermann et al. |
| 2003/0100897 A1 | 5/2003 | Metz-Stavenhagen |
| 2003/0100904 A1 | 5/2003 | Biedermann |
| 2003/0105460 A1 | 6/2003 | Crandall et al. |
| 2003/0109880 A1 | 6/2003 | Shirado et al. |
| 2003/0114852 A1 | 6/2003 | Biedermann et al. |
| 2003/0120275 A1 | 6/2003 | Lenke et al. |
| 2003/0125741 A1 | 7/2003 | Biedermann et al. |
| 2003/0125749 A1 | 7/2003 | Yuan et al. |
| 2003/0130659 A1 | 7/2003 | Haider |
| 2003/0130661 A1 | 7/2003 | Osman |
| 2003/0135210 A1 | 7/2003 | Dixon et al. |
| 2003/0135217 A1 | 7/2003 | Buttermann et al. |
| 2003/0139745 A1 | 7/2003 | Ashman |
| 2003/0149431 A1 | 8/2003 | Varieur |
| 2003/0149432 A1 | 8/2003 | Frigg et al. |
| 2003/0149435 A1 | 8/2003 | Baynham et al. |
| 2003/0153911 A1 | 8/2003 | Shluzas |
| 2003/0153912 A1 | 8/2003 | Graf |
| 2003/0153920 A1 | 8/2003 | Ralph et al. |
| 2003/0163133 A1 | 8/2003 | Altarac et al. |
| 2003/0167058 A1 | 9/2003 | Shluzas |
| 2003/0171749 A1 | 9/2003 | Le Couedic et al. |
| 2003/0176863 A1 | 9/2003 | Ueyama et al. |
| 2003/0181913 A1 | 9/2003 | Lieberman |
| 2003/0187433 A1 | 10/2003 | Lin |
| 2003/0187434 A1 | 10/2003 | Lin |
| 2003/0191470 A1 | 10/2003 | Ritland |
| 2003/0199872 A1 | 10/2003 | Markworth et al. |
| 2003/0199873 A1 | 10/2003 | Richelsoph |
| 2003/0208204 A1 | 11/2003 | Bailey et al. |
| 2003/0212398 A1 | 11/2003 | Jackson |
| 2003/0216735 A1 | 11/2003 | Altarac et al. |
| 2003/0220642 A1 | 11/2003 | Freudiger |
| 2003/0220643 A1 | 11/2003 | Ferree |
| 2003/0225408 A1 | 12/2003 | Nichols et al. |
| 2003/0229345 A1 | 12/2003 | Stahurski |
| 2003/0229347 A1 | 12/2003 | Sherman et al. |
| 2003/0236529 A1 | 12/2003 | Shluzas et al. |
| 2004/0006342 A1 | 1/2004 | Altarac et al. |
| 2004/0039384 A1 | 2/2004 | Boehm, Jr. et al. |
| 2004/0039385 A1 | 2/2004 | Mazda et al. |
| 2004/0049189 A1 | 3/2004 | Le Couedic et al. |
| 2004/0049190 A1 | 3/2004 | Biedermann et al. |
| 2004/0073215 A1 | 4/2004 | Carli |
| 2004/0073218 A1 | 4/2004 | Dahners |
| 2004/0078051 A1 | 4/2004 | Davison et al. |
| 2004/0078082 A1 | 4/2004 | Lange |
| 2004/0087949 A1 | 5/2004 | Bono et al. |
| 2004/0087950 A1 | 5/2004 | Teitelbaum |
| 2004/0087952 A1 | 5/2004 | Borgstrom et al. |
| 2004/0092934 A1 | 5/2004 | Howland |
| 2004/0092938 A1 | 5/2004 | Carli |
| 2004/0097933 A1 | 5/2004 | Lourdel et al. |

(56) References Cited

U.S. PATENT DOCUMENTS

| | | |
|---|---|---|
| 2004/0106925 A1 | 6/2004 | Culbert |
| 2004/0111091 A1 | 6/2004 | Ogilvie et al. |
| 2004/0122442 A1 | 6/2004 | Lewis |
| 2004/0127904 A1 | 7/2004 | Konieczynski et al. |
| 2004/0133207 A1 | 7/2004 | Abdou |
| 2004/0138660 A1 | 7/2004 | Serhan |
| 2004/0138662 A1 | 7/2004 | Landry et al. |
| 2004/0147928 A1 | 7/2004 | Landry et al. |
| 2004/0147929 A1 | 7/2004 | Biedermann et al. |
| 2004/0147937 A1 | 7/2004 | Dunbar, Jr. et al. |
| 2004/0153068 A1 | 8/2004 | Janowski et al. |
| 2004/0158245 A1 | 8/2004 | Chin |
| 2004/0158247 A1 | 8/2004 | Sitiso et al. |
| 2004/0158258 A1 | 8/2004 | Bonati et al. |
| 2004/0162560 A1 | 8/2004 | Raynor et al. |
| 2004/0167523 A1 | 8/2004 | Jackson |
| 2004/0167525 A1 | 8/2004 | Jackson |
| 2004/0172025 A1 | 9/2004 | Drewry et al. |
| 2004/0172031 A1 | 9/2004 | Rubecamp et al. |
| 2004/0172032 A1 | 9/2004 | Jackson |
| 2004/0176776 A1 | 9/2004 | Zubok et al. |
| 2004/0186473 A1 | 9/2004 | Cournoyer et al. |
| 2004/0186474 A1 | 9/2004 | Matthis et al. |
| 2004/0186475 A1 | 9/2004 | Falahee |
| 2004/0210216 A1 | 10/2004 | Farris et al. |
| 2004/0210227 A1 | 10/2004 | Trail et al. |
| 2004/0215190 A1 | 10/2004 | Nguyen et al. |
| 2004/0215191 A1 | 10/2004 | Kitchen |
| 2004/0220567 A1 | 11/2004 | Eisermann et al. |
| 2004/0220671 A1 | 11/2004 | Ralph et al. |
| 2004/0225289 A1 | 11/2004 | Biedermann et al. |
| 2004/0230100 A1 | 11/2004 | Shluzas |
| 2004/0236327 A1 | 11/2004 | Paul et al. |
| 2004/0236328 A1 | 11/2004 | Paul et al. |
| 2004/0236330 A1 | 11/2004 | Purcell et al. |
| 2004/0249378 A1 | 12/2004 | Saint Martin et al. |
| 2004/0254574 A1 | 12/2004 | Morrison et al. |
| 2004/0260283 A1 | 12/2004 | Wu et al. |
| 2004/0267264 A1 | 12/2004 | Konieczynski et al. |
| 2005/0010219 A1 | 1/2005 | Dalton |
| 2005/0027296 A1 | 2/2005 | Thramann et al. |
| 2005/0033298 A1 | 2/2005 | Hawkes et al. |
| 2005/0033436 A1 | 2/2005 | Schlapfer et al. |
| 2005/0033439 A1 | 2/2005 | Gordon et al. |
| 2005/0038430 A1 | 2/2005 | McKinley |
| 2005/0038432 A1 | 2/2005 | Shaolian et al. |
| 2005/0038433 A1 | 2/2005 | Young |
| 2005/0049588 A1 | 3/2005 | Jackson |
| 2005/0049589 A1 | 3/2005 | Jackson |
| 2005/0055026 A1 | 3/2005 | Biedermann et al. |
| 2005/0065514 A1 | 3/2005 | Studer |
| 2005/0065515 A1 | 3/2005 | Jahng |
| 2005/0065516 A1 | 3/2005 | Jahng |
| 2005/0065517 A1 | 3/2005 | Chin |
| 2005/0070899 A1 | 3/2005 | Doubler et al. |
| 2005/0070901 A1 | 3/2005 | David |
| 2005/0080415 A1 | 4/2005 | Keyer et al. |
| 2005/0085812 A1 | 4/2005 | Sherman et al. |
| 2005/0085813 A1 | 4/2005 | Spitler et al. |
| 2005/0085815 A1 | 4/2005 | Harms et al. |
| 2005/0085816 A1 | 4/2005 | Michelson |
| 2005/0090821 A1 | 4/2005 | Berrevoets et al. |
| 2005/0096652 A1 | 5/2005 | Burton |
| 2005/0096653 A1 | 5/2005 | Doubler et al. |
| 2005/0096654 A1 | 5/2005 | Lin |
| 2005/0107788 A1 | 5/2005 | Beaurain et al. |
| 2005/0113927 A1 | 5/2005 | Malek |
| 2005/0119658 A1 | 6/2005 | Ralph et al. |
| 2005/0124991 A1 | 6/2005 | Jahng |
| 2005/0131404 A1 | 6/2005 | Mazda et al. |
| 2005/0131405 A1 | 6/2005 | Molz, IV et al. |
| 2005/0131406 A1 | 6/2005 | Reiley et al. |
| 2005/0131407 A1 | 6/2005 | Sicvol et al. |
| 2005/0131408 A1 | 6/2005 | Sicvol et al. |
| 2005/0131413 A1 | 6/2005 | O'Driscoll et al. |
| 2005/0131419 A1 | 6/2005 | McCord et al. |
| 2005/0131421 A1 | 6/2005 | Anderson et al. |
| 2005/0131422 A1 | 6/2005 | Anderson |
| 2005/0137594 A1 | 6/2005 | Doubler et al. |
| 2005/0137597 A1 | 6/2005 | Butler et al. |
| 2005/0141986 A1 | 6/2005 | Flesher |
| 2005/0143737 A1 | 6/2005 | Pafford et al. |
| 2005/0143823 A1 | 6/2005 | Boyd et al. |
| 2005/0149020 A1 | 7/2005 | Jahng |
| 2005/0149053 A1 | 7/2005 | Varieur |
| 2005/0154389 A1 | 7/2005 | Selover et al. |
| 2005/0154390 A1 | 7/2005 | Biedermann et al. |
| 2005/0154391 A1 | 7/2005 | Doherty et al. |
| 2005/0159750 A1 | 7/2005 | Doherty |
| 2005/0165400 A1 | 7/2005 | Fernandez |
| 2005/0171540 A1 | 8/2005 | Lim et al. |
| 2005/0171543 A1 | 8/2005 | Timm et al. |
| 2005/0177154 A1 | 8/2005 | Moumene et al. |
| 2005/0177166 A1 | 8/2005 | Timm et al. |
| 2005/0182401 A1 | 8/2005 | Timm et al. |
| 2005/0182410 A1 | 8/2005 | Jackson |
| 2005/0187548 A1 | 8/2005 | Butler et al. |
| 2005/0187555 A1 | 8/2005 | Biedermann et al. |
| 2005/0192571 A1 | 9/2005 | Abdelgany |
| 2005/0192572 A1 | 9/2005 | Abdelgany et al. |
| 2005/0192573 A1 | 9/2005 | Abdelgany et al. |
| 2005/0192579 A1 | 9/2005 | Jackson |
| 2005/0192580 A1 | 9/2005 | Dalton |
| 2005/0192589 A1 | 9/2005 | Raymond et al. |
| 2005/0203511 A1 | 9/2005 | Wilson-MacDonald et al. |
| 2005/0203513 A1 | 9/2005 | Jahng et al. |
| 2005/0203514 A1 | 9/2005 | Jahng et al. |
| 2005/0203516 A1 | 9/2005 | Harms et al. |
| 2005/0203518 A1 | 9/2005 | Biedermann et al. |
| 2005/0203519 A1 | 9/2005 | Harms et al. |
| 2005/0215999 A1 | 9/2005 | Birkmeyer et al. |
| 2005/0216000 A1 | 9/2005 | Colleran et al. |
| 2005/0216001 A1 | 9/2005 | David |
| 2005/0216003 A1 | 9/2005 | Biedermann et al. |
| 2005/0228326 A1 | 10/2005 | Kalfas et al. |
| 2005/0228379 A1 | 10/2005 | Jackson |
| 2005/0228385 A1 | 10/2005 | Lee et al. |
| 2005/0228400 A1 | 10/2005 | Chao |
| 2005/0228501 A1 | 10/2005 | Miller et al. |
| 2005/0234450 A1 | 10/2005 | Barker |
| 2005/0234451 A1 | 10/2005 | Markworth |
| 2005/0234452 A1 | 10/2005 | Malandain |
| 2005/0234453 A1 | 10/2005 | Shaolian et al. |
| 2005/0234454 A1 | 10/2005 | Chin |
| 2005/0234456 A1 | 10/2005 | Malandain |
| 2005/0234459 A1 | 10/2005 | Falahee et al. |
| 2005/0240181 A1 | 10/2005 | Boomer et al. |
| 2005/0240183 A1 | 10/2005 | Vaughan |
| 2005/0245930 A1 | 11/2005 | Timm et al. |
| 2005/0251137 A1 | 11/2005 | Ball |
| 2005/0251139 A1 | 11/2005 | Roh |
| 2005/0251140 A1 | 11/2005 | Shaolian et al. |
| 2005/0251141 A1 | 11/2005 | Frigg et al. |
| 2005/0260058 A1 | 11/2005 | Cassagne, III |
| 2005/0261687 A1 | 11/2005 | Garamszegi et al. |
| 2005/0267470 A1 | 12/2005 | McBride |
| 2005/0267471 A1 | 12/2005 | Biedermann et al. |
| 2005/0267472 A1 | 12/2005 | Biedermann et al. |
| 2005/0267474 A1 | 12/2005 | Dalton |
| 2005/0267477 A1 | 12/2005 | Jackson |
| 2005/0273099 A1 | 12/2005 | Baccelli et al. |
| 2005/0273101 A1 | 12/2005 | Schumacher |
| 2005/0277919 A1 | 12/2005 | Slivka et al. |
| 2005/0277922 A1 | 12/2005 | Trieu et al. |
| 2005/0277923 A1 | 12/2005 | Sweeney |
| 2005/0277925 A1 | 12/2005 | Mujwid |
| 2005/0277927 A1 | 12/2005 | Guenther et al. |
| 2005/0277928 A1 | 12/2005 | Boschert |
| 2005/0277931 A1 | 12/2005 | Sweeney et al. |
| 2005/0277934 A1 | 12/2005 | Vardiman |
| 2005/0278023 A1 | 12/2005 | Zwirkoski |
| 2005/0283152 A1 | 12/2005 | Lindemann et al. |
| 2005/0283157 A1 | 12/2005 | Coates et al. |
| 2005/0283238 A1 | 12/2005 | Reiley |

(56) References Cited

U.S. PATENT DOCUMENTS

| | | |
|---|---|---|
| 2005/0283244 A1 | 12/2005 | Gordon et al. |
| 2005/0288669 A1 | 12/2005 | Abdou |
| 2005/0288670 A1 | 12/2005 | Panjabi |
| 2005/0288672 A1 | 12/2005 | Ferree |
| 2005/0288673 A1 | 12/2005 | Catbagan et al. |
| 2006/0004359 A1 | 1/2006 | Kramer et al. |
| 2006/0004363 A1 | 1/2006 | Brockmeyer et al. |
| 2006/0009767 A1 | 1/2006 | Kiester |
| 2006/0009769 A1 | 1/2006 | Lieberman |
| 2006/0009770 A1 | 1/2006 | Speirs et al. |
| 2006/0009780 A1 | 1/2006 | Foley et al. |
| 2006/0015099 A1 | 1/2006 | Cannon et al. |
| 2006/0025767 A1 | 2/2006 | Khalili |
| 2006/0025768 A1 | 2/2006 | Iott et al. |
| 2006/0025770 A1 | 2/2006 | Schlapfer et al. |
| 2006/0025771 A1 | 2/2006 | Jackson |
| 2006/0030850 A1 | 2/2006 | Keegan et al. |
| 2006/0036240 A1 | 2/2006 | Colleran et al. |
| 2006/0036242 A1 | 2/2006 | Nilsson et al. |
| 2006/0036243 A1 | 2/2006 | Sasso et al. |
| 2006/0036244 A1 | 2/2006 | Spitler et al. |
| 2006/0036246 A1 | 2/2006 | Carl et al. |
| 2006/0036252 A1 | 2/2006 | Baynham et al. |
| 2006/0036254 A1 | 2/2006 | Lim |
| 2006/0036256 A1 | 2/2006 | Carl et al. |
| 2006/0036259 A1 | 2/2006 | Carl et al. |
| 2006/0036323 A1 | 2/2006 | Carl et al. |
| 2006/0036324 A1 | 2/2006 | Sachs et al. |
| 2006/0052780 A1 | 3/2006 | Errico et al. |
| 2006/0052783 A1 | 3/2006 | Dant et al. |
| 2006/0052784 A1 | 3/2006 | Dant et al. |
| 2006/0052786 A1 | 3/2006 | Dant et al. |
| 2006/0058788 A1 | 3/2006 | Hammer et al. |
| 2006/0058790 A1 | 3/2006 | Carl et al. |
| 2006/0064090 A1 | 3/2006 | Park |
| 2006/0064091 A1 | 3/2006 | Ludwig et al. |
| 2006/0064092 A1 | 3/2006 | Howland |
| 2006/0069390 A1 | 3/2006 | Frigg et al. |
| 2006/0074418 A1 | 4/2006 | Jackson |
| 2006/0074419 A1 | 4/2006 | Taylor et al. |
| 2006/0079894 A1 | 4/2006 | Colleran et al. |
| 2006/0079895 A1 | 4/2006 | McLeer |
| 2006/0079896 A1 | 4/2006 | Kwak et al. |
| 2006/0079898 A1 | 4/2006 | Ainsworth |
| 2006/0079899 A1 | 4/2006 | Ritland |
| 2006/0084977 A1 | 4/2006 | Lieberman |
| 2006/0084980 A1 | 4/2006 | Melkent et al. |
| 2006/0084981 A1 | 4/2006 | Shluzas |
| 2006/0084982 A1 | 4/2006 | Kim |
| 2006/0084983 A1 | 4/2006 | Kim |
| 2006/0084984 A1 | 4/2006 | Kim |
| 2006/0084985 A1 | 4/2006 | Kim |
| 2006/0084987 A1 | 4/2006 | Kim |
| 2006/0084988 A1 | 4/2006 | Kim |
| 2006/0084989 A1 | 4/2006 | Dickinson et al. |
| 2006/0084991 A1 | 4/2006 | Borgstrom et al. |
| 2006/0085069 A1 | 4/2006 | Kim |
| 2006/0085070 A1 | 4/2006 | Kim |
| 2006/0089643 A1 | 4/2006 | Mujwid |
| 2006/0089644 A1 | 4/2006 | Felix |
| 2006/0089645 A1 | 4/2006 | Eckman |
| 2006/0095035 A1 | 5/2006 | Jones et al. |
| 2006/0095037 A1 | 5/2006 | Jones et al. |
| 2006/0095038 A1 | 5/2006 | Jackson |
| 2006/0100621 A1 | 5/2006 | Jackson |
| 2006/0100622 A1 | 5/2006 | Jackson |
| 2006/0106381 A1 | 5/2006 | Ferree et al. |
| 2006/0106394 A1 | 5/2006 | Colleran |
| 2006/0111713 A1 | 5/2006 | Jackson |
| 2006/0111715 A1 | 5/2006 | Jackson |
| 2006/0116677 A1 | 6/2006 | Burd et al. |
| 2006/0122597 A1 | 6/2006 | Jones et al. |
| 2006/0122599 A1 | 6/2006 | Drewry et al. |
| 2006/0129147 A1 | 6/2006 | Biedermann et al. |
| 2006/0129149 A1 | 6/2006 | Iott et al. |
| 2006/0129239 A1 | 6/2006 | Kwak |
| 2006/0142758 A1 | 6/2006 | Petit |
| 2006/0142760 A1 | 6/2006 | McDonnell |
| 2006/0149228 A1 | 7/2006 | Schlapfer et al. |
| 2006/0149229 A1 | 7/2006 | Kwak et al. |
| 2006/0149238 A1 | 7/2006 | Sherman et al. |
| 2006/0149240 A1 | 7/2006 | Jackson |
| 2006/0149241 A1 | 7/2006 | Richelsoph et al. |
| 2006/0149251 A1 | 7/2006 | Ziolo et al. |
| 2006/0155277 A1 | 7/2006 | Metz-Stavenhagen |
| 2006/0161152 A1 | 7/2006 | Ensign et al. |
| 2006/0166535 A1 | 7/2006 | Brumfield et al. |
| 2006/0167454 A1 | 7/2006 | Ludwig et al. |
| 2006/0167455 A1 | 7/2006 | Clement et al. |
| 2006/0173456 A1 | 8/2006 | Hawkes et al. |
| 2006/0184171 A1 | 8/2006 | Biedermann |
| 2006/0184180 A1 | 8/2006 | Augostino |
| 2006/0189983 A1 | 8/2006 | Fallin et al. |
| 2006/0189985 A1 | 8/2006 | Lewis |
| 2006/0195090 A1 | 8/2006 | Suddaby |
| 2006/0195093 A1 | 8/2006 | Jahng |
| 2006/0195198 A1 | 8/2006 | James |
| 2006/0200023 A1 | 9/2006 | Melkent et al. |
| 2006/0200130 A1 | 9/2006 | Hawkins et al. |
| 2006/0200131 A1 | 9/2006 | Chao et al. |
| 2006/0200132 A1 | 9/2006 | Chao et al. |
| 2006/0200133 A1 | 9/2006 | Jackson |
| 2006/0200149 A1 | 9/2006 | Hoy et al. |
| 2006/0212033 A1 | 9/2006 | Rothman et al. |
| 2006/0212034 A1 | 9/2006 | Triplett et al. |
| 2006/0217713 A1 | 9/2006 | Serhan et al. |
| 2006/0217716 A1 | 9/2006 | Baker et al. |
| 2006/0217719 A1 | 9/2006 | Albert et al. |
| 2006/0229608 A1 | 10/2006 | Foster et al. |
| 2006/0229609 A1 | 10/2006 | Wang |
| 2006/0229613 A1 | 10/2006 | Timm |
| 2006/0229614 A1 | 10/2006 | Foley et al. |
| 2006/0229615 A1 | 10/2006 | Abdou |
| 2006/0241593 A1 | 10/2006 | Sherman et al. |
| 2006/0241595 A1 | 10/2006 | Molz, IV et al. |
| 2006/0241600 A1 | 10/2006 | Ensign et al. |
| 2006/0241601 A1 | 10/2006 | Trautwein et al. |
| 2006/0241603 A1 | 10/2006 | Jackson |
| 2006/0247624 A1 | 11/2006 | Banouskou et al. |
| 2006/0247630 A1 | 11/2006 | Iott et al. |
| 2006/0247631 A1 | 11/2006 | Ahn et al. |
| 2006/0247632 A1 | 11/2006 | Winslow et al. |
| 2006/0247633 A1 | 11/2006 | Winslow et al. |
| 2006/0247658 A1 | 11/2006 | Pond, Jr. et al. |
| 2006/0260483 A1 | 11/2006 | Hartmann et al. |
| 2006/0264933 A1 | 11/2006 | Baker et al. |
| 2006/0264934 A1 | 11/2006 | Fallin |
| 2006/0264935 A1 | 11/2006 | White |
| 2006/0264936 A1 | 11/2006 | Partin et al. |
| 2006/0264962 A1 | 11/2006 | Chin et al. |
| 2006/0276787 A1 | 12/2006 | Zubok et al. |
| 2006/0276789 A1 | 12/2006 | Jackson |
| 2006/0276791 A1 | 12/2006 | Shluzas |
| 2006/0276792 A1 | 12/2006 | Ensign et al. |
| 2006/0282075 A1 | 12/2006 | Labrom et al. |
| 2006/0282076 A1 | 12/2006 | Labrom et al. |
| 2006/0282077 A1 | 12/2006 | Labrom et al. |
| 2006/0282078 A1 | 12/2006 | Labrom et al. |
| 2006/0282079 A1 | 12/2006 | Labrom et al. |
| 2006/0282080 A1 | 12/2006 | Albert |
| 2006/0293657 A1 | 12/2006 | Hartmann |
| 2006/0293659 A1 | 12/2006 | Alvarez |
| 2006/0293663 A1 | 12/2006 | Walkenhorst |
| 2006/0293666 A1 | 12/2006 | Matthis et al. |
| 2006/0293693 A1 | 12/2006 | Farr et al. |
| 2007/0005062 A1 | 1/2007 | Lange et al. |
| 2007/0005063 A1 | 1/2007 | Bruneau et al. |
| 2007/0005137 A1 | 1/2007 | Kwak |
| 2007/0016190 A1 | 1/2007 | Martinez et al. |
| 2007/0016194 A1 | 1/2007 | Shaolian et al. |
| 2007/0016200 A1 | 1/2007 | Jackson |
| 2007/0021750 A1 | 1/2007 | Shluzas et al. |
| 2007/0032123 A1 | 2/2007 | Timm et al. |
| 2007/0043356 A1 | 2/2007 | Timm et al. |

(56) References Cited

U.S. PATENT DOCUMENTS

| | | |
|---|---|---|
| 2007/0043357 A1 | 2/2007 | Kirschman |
| 2007/0043358 A1 | 2/2007 | Molz, IV et al. |
| 2007/0043359 A1 | 2/2007 | Altarac et al. |
| 2007/0043364 A1 | 2/2007 | Cawley et al. |
| 2007/0049931 A1 | 3/2007 | Justis et al. |
| 2007/0049933 A1 | 3/2007 | Ahn et al. |
| 2007/0049936 A1 | 3/2007 | Colleran et al. |
| 2007/0055236 A1 | 3/2007 | Hudgins et al. |
| 2007/0055239 A1 | 3/2007 | Sweeney et al. |
| 2007/0055240 A1 | 3/2007 | Matthis et al. |
| 2007/0055241 A1 | 3/2007 | Matthis et al. |
| 2007/0055242 A1 | 3/2007 | Bailly |
| 2007/0055244 A1 | 3/2007 | Jackson |
| 2007/0073289 A1 | 3/2007 | Kwak et al. |
| 2007/0073290 A1 | 3/2007 | Boehm, Jr. |
| 2007/0073291 A1 | 3/2007 | Cordaro et al. |
| 2007/0073293 A1 | 3/2007 | Martz et al. |
| 2007/0073294 A1 | 3/2007 | Chin et al. |
| 2007/0078460 A1 | 4/2007 | Frigg et al. |
| 2007/0078461 A1 | 4/2007 | Shluzas |
| 2007/0083199 A1 | 4/2007 | Baccelli |
| 2007/0088357 A1 | 4/2007 | Johnson et al. |
| 2007/0088359 A1 | 4/2007 | Woods et al. |
| 2007/0090238 A1 | 4/2007 | Justis |
| 2007/0093813 A1 | 4/2007 | Callahan et al. |
| 2007/0093814 A1 | 4/2007 | Callahan, II et al. |
| 2007/0093815 A1 | 4/2007 | Callahan, II et al. |
| 2007/0093818 A1 | 4/2007 | Biedermann et al. |
| 2007/0093819 A1 | 4/2007 | Albert |
| 2007/0093824 A1 | 4/2007 | Hestad et al. |
| 2007/0093826 A1 | 4/2007 | Hawkes et al. |
| 2007/0093833 A1 | 4/2007 | Kuiper et al. |
| 2007/0100341 A1 | 5/2007 | Reglos et al. |
| 2007/0118117 A1 | 5/2007 | Altarac et al. |
| 2007/0118118 A1 | 5/2007 | Kwak et al. |
| 2007/0118119 A1 | 5/2007 | Hestad |
| 2007/0118122 A1 | 5/2007 | Butler et al. |
| 2007/0118123 A1 | 5/2007 | Strausbaugh et al. |
| 2007/0118124 A1 | 5/2007 | Biedermann et al. |
| 2007/0123867 A1 | 5/2007 | Kirschman |
| 2007/0123870 A1 | 5/2007 | Jeon et al. |
| 2007/0156142 A1 | 7/2007 | Rezach et al. |
| 2007/0161986 A1 | 7/2007 | Levy |
| 2007/0161991 A1 | 7/2007 | Altarac et al. |
| 2007/0161994 A1 | 7/2007 | Lowery et al. |
| 2007/0161995 A1 | 7/2007 | Trautwein et al. |
| 2007/0161996 A1 | 7/2007 | Biedermann et al. |
| 2007/0161997 A1 | 7/2007 | Thramann et al. |
| 2007/0161999 A1 | 7/2007 | Biedermann et al. |
| 2007/0167948 A1 | 7/2007 | Abdou |
| 2007/0167949 A1 | 7/2007 | Altarac et al. |
| 2007/0173818 A1 | 7/2007 | Hestad et al. |
| 2007/0173819 A1 | 7/2007 | Sandlin |
| 2007/0173820 A1 | 7/2007 | Trieu |
| 2007/0173822 A1 | 7/2007 | Bruneau et al. |
| 2007/0173828 A1 | 7/2007 | Firkins et al. |
| 2007/0173832 A1 | 7/2007 | Tebbe et al. |
| 2007/0191832 A1 | 8/2007 | Trieu |
| 2007/0191839 A1 | 8/2007 | Justis et al. |
| 2007/0191841 A1 | 8/2007 | Justis et al. |
| 2007/0191846 A1 | 8/2007 | Bruneau et al. |
| 2007/0198014 A1 | 8/2007 | Graf et al. |
| 2007/0208344 A1 | 9/2007 | Young |
| 2007/0213720 A1 | 9/2007 | Gordon et al. |
| 2007/0225707 A1 | 9/2007 | Wisnewski et al. |
| 2007/0225708 A1 | 9/2007 | Biedermann et al. |
| 2007/0225711 A1 | 9/2007 | Ensign |
| 2007/0233073 A1 | 10/2007 | Wisnewski et al. |
| 2007/0233078 A1 | 10/2007 | Justis et al. |
| 2007/0233080 A1 | 10/2007 | Na et al. |
| 2007/0233085 A1 | 10/2007 | Biedermann et al. |
| 2007/0233086 A1 | 10/2007 | Harms et al. |
| 2007/0233089 A1 | 10/2007 | Dipoto et al. |
| 2007/0233092 A1 | 10/2007 | Falahee |
| 2007/0233094 A1 | 10/2007 | Colleran et al. |
| 2007/0233095 A1 | 10/2007 | Schlaepfer |
| 2007/0233155 A1 | 10/2007 | Lovell |
| 2007/0244481 A1 | 10/2007 | Timm |
| 2007/0244482 A1 | 10/2007 | Aferzon |
| 2007/0250061 A1 | 10/2007 | Chin et al. |
| 2007/0260243 A1 | 11/2007 | Kagami |
| 2007/0270813 A1 | 11/2007 | Garamszegi |
| 2007/0270821 A1 | 11/2007 | Trieu et al. |
| 2007/0270836 A1 | 11/2007 | Bruneau et al. |
| 2007/0270837 A1 | 11/2007 | Eckhardt et al. |
| 2007/0270838 A1 | 11/2007 | Bruneau et al. |
| 2007/0270843 A1 | 11/2007 | Matthis et al. |
| 2007/0270869 A1 | 11/2007 | Young et al. |
| 2007/0276371 A1 | 11/2007 | Baynham et al. |
| 2007/0276379 A1 | 11/2007 | Miller et al. |
| 2007/0276380 A1 | 11/2007 | Jahng et al. |
| 2007/0288004 A1 | 12/2007 | Alvarez |
| 2007/0288012 A1 | 12/2007 | Colleran et al. |
| 2007/0293862 A1 | 12/2007 | Jackson |
| 2008/0009862 A1 | 1/2008 | Hoffman |
| 2008/0009864 A1 | 1/2008 | Forton et al. |
| 2008/0015578 A1 | 1/2008 | Erickson et al. |
| 2008/0015579 A1 | 1/2008 | Whipple |
| 2008/0015580 A1 | 1/2008 | Chao |
| 2008/0015597 A1 | 1/2008 | Whipple |
| 2008/0021454 A1 | 1/2008 | Chao et al. |
| 2008/0021455 A1 | 1/2008 | Chao et al. |
| 2008/0021462 A1 | 1/2008 | Trieu |
| 2008/0021464 A1 | 1/2008 | Morin et al. |
| 2008/0021465 A1 | 1/2008 | Shadduck et al. |
| 2008/0027432 A1 | 1/2008 | Strauss et al. |
| 2008/0039843 A1 | 2/2008 | Abdou |
| 2008/0045951 A1 | 2/2008 | Fanger et al. |
| 2008/0045955 A1 | 2/2008 | Berrevoets et al. |
| 2008/0051780 A1 | 2/2008 | Vaidya et al. |
| 2008/0051787 A1 | 2/2008 | Remington et al. |
| 2008/0058811 A1 | 3/2008 | Alleyne et al. |
| 2008/0058812 A1 | 3/2008 | Zehnder |
| 2008/0065071 A1 | 3/2008 | Park |
| 2008/0065073 A1 | 3/2008 | Perriello et al. |
| 2008/0065075 A1 | 3/2008 | Dant |
| 2008/0065077 A1 | 3/2008 | Ferree |
| 2008/0065079 A1 | 3/2008 | Bruneau et al. |
| 2008/0071273 A1 | 3/2008 | Hawkes et al. |
| 2008/0071274 A1 | 3/2008 | Ensign |
| 2008/0077136 A1 | 3/2008 | Triplett et al. |
| 2008/0077138 A1 | 3/2008 | Cohen et al. |
| 2008/0077139 A1 | 3/2008 | Landry et al. |
| 2008/0077143 A1 | 3/2008 | Shluzas |
| 2008/0086131 A1 | 4/2008 | Daly et al. |
| 2008/0086132 A1 | 4/2008 | Biedermann et al. |
| 2008/0091213 A1 | 4/2008 | Jackson |
| 2008/0097441 A1 | 4/2008 | Hayes et al. |
| 2008/0103502 A1 | 5/2008 | Capote et al. |
| 2008/0108992 A1 | 5/2008 | Barry et al. |
| 2008/0114362 A1 | 5/2008 | Justis et al. |
| 2008/0114403 A1 | 5/2008 | Kuester et al. |
| 2008/0119849 A1 | 5/2008 | Beardsley et al. |
| 2008/0119857 A1 | 5/2008 | Potash |
| 2008/0125777 A1 | 5/2008 | Veldman et al. |
| 2008/0125787 A1 | 5/2008 | Doubler et al. |
| 2008/0125813 A1 | 5/2008 | Erickson et al. |
| 2008/0132957 A1 | 6/2008 | Matthis et al. |
| 2008/0140075 A1 | 6/2008 | Ensign et al. |
| 2008/0140076 A1 | 6/2008 | Jackson |
| 2008/0140133 A1 | 6/2008 | Allard et al. |
| 2008/0140136 A1 | 6/2008 | Jackson |
| 2008/0147121 A1 | 6/2008 | Justis et al. |
| 2008/0147122 A1 | 6/2008 | Jackson |
| 2008/0147129 A1 | 6/2008 | Biedermann et al. |
| 2008/0147195 A1 | 6/2008 | Kwak et al. |
| 2008/0154279 A1 | 6/2008 | Schumacher et al. |
| 2008/0154308 A1 | 6/2008 | Sherman et al. |
| 2008/0154315 A1 | 6/2008 | Jackson |
| 2008/0161857 A1 | 7/2008 | Hestad et al. |
| 2008/0161863 A1 | 7/2008 | Arnold et al. |
| 2008/0167687 A1 | 7/2008 | Colleran et al. |
| 2008/0172090 A1 | 7/2008 | Molz |
| 2008/0172091 A1 | 7/2008 | Anderson |

(56) References Cited

U.S. PATENT DOCUMENTS

| | | |
|---|---|---|
| 2008/0172096 A1 | 7/2008 | Hawkins |
| 2008/0177316 A1 | 7/2008 | Bergeron et al. |
| 2008/0177317 A1 | 7/2008 | Jackson |
| 2008/0177321 A1 | 7/2008 | Drewry et al. |
| 2008/0177322 A1 | 7/2008 | Davis et al. |
| 2008/0177323 A1 | 7/2008 | Null et al. |
| 2008/0177388 A1 | 7/2008 | Patterson et al. |
| 2008/0183212 A1 | 7/2008 | Veldman et al. |
| 2008/0183213 A1 | 7/2008 | Veldman et al. |
| 2008/0183215 A1 | 7/2008 | Altarac et al. |
| 2008/0183216 A1 | 7/2008 | Jackson |
| 2008/0183223 A1 | 7/2008 | Jeon et al. |
| 2008/0188898 A1 | 8/2008 | Jackson |
| 2008/0195153 A1 | 8/2008 | Thompson |
| 2008/0195155 A1 | 8/2008 | Hoffman et al. |
| 2008/0195159 A1 | 8/2008 | Kloss et al. |
| 2008/0200918 A1 | 8/2008 | Spitler et al. |
| 2008/0200956 A1 | 8/2008 | Beckwith et al. |
| 2008/0215095 A1 | 9/2008 | Biedermann et al. |
| 2008/0215100 A1 | 9/2008 | Matthis et al. |
| 2008/0228184 A1 | 9/2008 | Hestad |
| 2008/0228228 A1 | 9/2008 | Hestad et al. |
| 2008/0234736 A1 | 9/2008 | Trieu et al. |
| 2008/0234737 A1 | 9/2008 | Boschert |
| 2008/0234738 A1 | 9/2008 | Zylber et al. |
| 2008/0234739 A1 | 9/2008 | Hudgins et al. |
| 2008/0234744 A1 | 9/2008 | Zylber et al. |
| 2008/0234756 A1 | 9/2008 | Sutcliffe et al. |
| 2008/0234759 A1 | 9/2008 | Marino |
| 2008/0234761 A1 | 9/2008 | Jackson |
| 2008/0243052 A1 | 10/2008 | Pond et al. |
| 2008/0243185 A1 | 10/2008 | Felix et al. |
| 2008/0243193 A1 | 10/2008 | Ensign et al. |
| 2008/0249570 A1 | 10/2008 | Carson et al. |
| 2008/0262548 A1 | 10/2008 | Lange et al. |
| 2008/0262551 A1 | 10/2008 | Rice et al. |
| 2008/0262554 A1 | 10/2008 | Hayes et al. |
| 2008/0262556 A1 | 10/2008 | Jacofsky et al. |
| 2008/0269742 A1 | 10/2008 | Levy et al. |
| 2008/0269804 A1 | 10/2008 | Holt |
| 2008/0269805 A1 | 10/2008 | Dekutoski et al. |
| 2008/0275456 A1 | 11/2008 | Vonwiller et al. |
| 2008/0275504 A1 | 11/2008 | Bonin et al. |
| 2008/0287994 A1 | 11/2008 | Perez-Cruet et al. |
| 2008/0288002 A1 | 11/2008 | Crall et al. |
| 2008/0294203 A1 | 11/2008 | Kovach et al. |
| 2008/0300630 A1 | 12/2008 | Bonnema et al. |
| 2008/0300631 A1 | 12/2008 | Tornier |
| 2008/0300633 A1 | 12/2008 | Jackson |
| 2008/0306513 A1 | 12/2008 | Winslow et al. |
| 2008/0306525 A1 | 12/2008 | Mitchell et al. |
| 2008/0306526 A1 | 12/2008 | Winslow et al. |
| 2008/0306533 A1 | 12/2008 | Winslow et al. |
| 2008/0306536 A1 | 12/2008 | Frigg et al. |
| 2008/0306540 A1 | 12/2008 | Mitchell et al. |
| 2008/0306543 A1 | 12/2008 | Cain et al. |
| 2008/0312655 A1 | 12/2008 | Kirschman et al. |
| 2008/0312692 A1 | 12/2008 | Brennan et al. |
| 2008/0312696 A1 | 12/2008 | Butters et al. |
| 2008/0312701 A1 | 12/2008 | Butters et al. |
| 2008/0312703 A1 | 12/2008 | Hestad et al. |
| 2008/0312704 A1 | 12/2008 | Hestad et al. |
| 2008/0319482 A1 | 12/2008 | Jackson |
| 2008/0319490 A1 | 12/2008 | Jackson |
| 2009/0005787 A1 | 1/2009 | Crall et al. |
| 2009/0005813 A1 | 1/2009 | Crall et al. |
| 2009/0005814 A1 | 1/2009 | Miller et al. |
| 2009/0012567 A1 | 1/2009 | Biedermann et al. |
| 2009/0018557 A1 | 1/2009 | Pisharodi |
| 2009/0018583 A1 | 1/2009 | Song et al. |
| 2009/0024165 A1 | 1/2009 | Ferree |
| 2009/0024169 A1 | 1/2009 | Triplett et al. |
| 2009/0030457 A1 | 1/2009 | Janowski et al. |
| 2009/0036929 A1 | 2/2009 | Reglos et al. |
| 2009/0036932 A1 | 2/2009 | Rouyer et al. |
| 2009/0036934 A1 | 2/2009 | Biedermann et al. |
| 2009/0048601 A1 | 2/2009 | Forton et al. |
| 2009/0048631 A1 | 2/2009 | Bhatnagar et al. |
| 2009/0062860 A1 | 3/2009 | Frasier et al. |
| 2009/0062865 A1 | 3/2009 | Schumacher |
| 2009/0062866 A1 | 3/2009 | Jackson |
| 2009/0062867 A1 | 3/2009 | Schumacher |
| 2009/0062914 A1 | 3/2009 | Marino |
| 2009/0069849 A1 | 3/2009 | Oh et al. |
| 2009/0069852 A1 | 3/2009 | Farris et al. |
| 2009/0069853 A1 | 3/2009 | Schumacher |
| 2009/0076550 A1 | 3/2009 | Bernhardt, Jr. et al. |
| 2009/0076552 A1 | 3/2009 | Tornier |
| 2009/0082666 A1 | 3/2009 | Geist et al. |
| 2009/0082812 A1 | 3/2009 | Lewis |
| 2009/0082815 A1 | 3/2009 | Zylber et al. |
| 2009/0082819 A1 | 3/2009 | Blain et al. |
| 2009/0088769 A1 | 4/2009 | Poletti |
| 2009/0088799 A1 | 4/2009 | Yeh |
| 2009/0088803 A1 | 4/2009 | Justis et al. |
| 2009/0088807 A1 | 4/2009 | Castaneda et al. |
| 2009/0093820 A1 | 4/2009 | Trieu et al. |
| 2009/0093843 A1 | 4/2009 | Lemoine et al. |
| 2009/0093846 A1 | 4/2009 | Hestad et al. |
| 2009/0099606 A1 | 4/2009 | Hestad et al. |
| 2009/0099608 A1 | 4/2009 | Szczesny |
| 2009/0105769 A1 | 4/2009 | Rock et al. |
| 2009/0105770 A1 | 4/2009 | Berrevoets et al. |
| 2009/0105771 A1 | 4/2009 | Lei et al. |
| 2009/0105820 A1 | 4/2009 | Jackson |
| 2009/0112265 A1 | 4/2009 | Hudgins et al. |
| 2009/0112266 A1 | 4/2009 | Weng et al. |
| 2009/0112269 A1 | 4/2009 | Lieberman et al. |
| 2009/0118772 A1 | 5/2009 | Diederich et al. |
| 2009/0131983 A1 | 5/2009 | Biedermann et al. |
| 2009/0138044 A1 | 5/2009 | Bergeron et al. |
| 2009/0138052 A1 | 5/2009 | Biedermann et al. |
| 2009/0143827 A1 | 6/2009 | Levy et al. |
| 2009/0143828 A1 | 6/2009 | Stad et al. |
| 2009/0149885 A1 | 6/2009 | Durward et al. |
| 2009/0149892 A1 | 6/2009 | Stad et al. |
| 2009/0157120 A1 | 6/2009 | Marino et al. |
| 2009/0163901 A1 | 6/2009 | Fisher et al. |
| 2009/0163953 A1 | 6/2009 | Biedermann et al. |
| 2009/0163954 A1 | 6/2009 | Kwak |
| 2009/0163955 A1 | 6/2009 | Moumene et al. |
| 2009/0163956 A1 | 6/2009 | Biedermann et al. |
| 2009/0163961 A1 | 6/2009 | Kirschman |
| 2009/0163963 A1 | 6/2009 | Berrevoets |
| 2009/0171392 A1 | 7/2009 | Garcia-Bengochea et al. |
| 2009/0171395 A1 | 7/2009 | Jeon et al. |
| 2009/0177232 A1 | 7/2009 | Kiester |
| 2009/0177237 A1 | 7/2009 | Zucherman et al. |
| 2009/0182380 A1 | 7/2009 | Abdelgany |
| 2009/0182430 A1 | 7/2009 | Tyber et al. |
| 2009/0192548 A1 | 7/2009 | Jeon et al. |
| 2009/0192551 A1 | 7/2009 | Cianfrani et al. |
| 2009/0198280 A1 | 8/2009 | Spratt et al. |
| 2009/0198281 A1 | 8/2009 | Rice et al. |
| 2009/0198289 A1 | 8/2009 | Manderson |
| 2009/0198291 A1 | 8/2009 | Kevin et al. |
| 2009/0216278 A1 | 8/2009 | Song |
| 2009/0216280 A1 | 8/2009 | Hutchinson |
| 2009/0221877 A1 | 9/2009 | Woods |
| 2009/0228045 A1 | 9/2009 | Hayes et al. |
| 2009/0240292 A1 | 9/2009 | Butler et al. |
| 2009/0248030 A1 | 10/2009 | Butler et al. |
| 2009/0248075 A1 | 10/2009 | Ogilvie et al. |
| 2009/0248077 A1 | 10/2009 | Johns |
| 2009/0248083 A1 | 10/2009 | Patterson et al. |
| 2009/0248088 A1 | 10/2009 | Biedermann |
| 2009/0254125 A1 | 10/2009 | Predick |
| 2009/0259254 A1 | 10/2009 | Pisharodi |
| 2009/0259257 A1 | 10/2009 | Prevost |
| 2009/0259258 A1 | 10/2009 | Perez-Cruet et al. |
| 2009/0264895 A1 | 10/2009 | Gasperut et al. |
| 2009/0264896 A1 | 10/2009 | Biedermann et al. |
| 2009/0264930 A1 | 10/2009 | McBride |
| 2009/0264933 A1 | 10/2009 | Carls et al. |

(56) References Cited

U.S. PATENT DOCUMENTS

| | | |
|---|---|---|
| 2009/0270916 A1 | 10/2009 | Ramsay et al. |
| 2009/0270917 A1 | 10/2009 | Boehm |
| 2009/0270920 A1 | 10/2009 | Douget et al. |
| 2009/0270921 A1 | 10/2009 | Krause |
| 2009/0270922 A1 | 10/2009 | Biedermann et al. |
| 2009/0275981 A1 | 11/2009 | Abdelgany et al. |
| 2009/0275983 A1 | 11/2009 | Veldman et al. |
| 2009/0275985 A1 | 11/2009 | Jackson |
| 2009/0275986 A1 | 11/2009 | Prevost et al. |
| 2009/0281542 A1 | 11/2009 | Justis |
| 2009/0281571 A1 | 11/2009 | Weaver et al. |
| 2009/0281572 A1 | 11/2009 | White |
| 2009/0281573 A1 | 11/2009 | Biedermann et al. |
| 2009/0281574 A1 | 11/2009 | Jackson |
| 2009/0287252 A1 | 11/2009 | Marik et al. |
| 2009/0287253 A1 | 11/2009 | Felix et al. |
| 2009/0299411 A1 | 12/2009 | Laskowitz et al. |
| 2009/0299415 A1 | 12/2009 | Pimenta |
| 2009/0306719 A1 | 12/2009 | Meyer, III et al. |
| 2009/0306720 A1 | 12/2009 | Doubler et al. |
| 2009/0312804 A1 | 12/2009 | Gamache et al. |
| 2009/0326582 A1 | 12/2009 | Songer et al. |
| 2009/0326583 A1 | 12/2009 | Moumene et al. |
| 2009/0326586 A1 | 12/2009 | Duarte |
| 2010/0004692 A1 | 1/2010 | Biedermann et al. |
| 2010/0004694 A1 | 1/2010 | Little |
| 2010/0004695 A1 | 1/2010 | Stad et al. |
| 2010/0010540 A1 | 1/2010 | Park |
| 2010/0010542 A1 | 1/2010 | Jackson |
| 2010/0010543 A1 | 1/2010 | Jackson |
| 2010/0023061 A1 | 1/2010 | Randol et al. |
| 2010/0030224 A1 | 2/2010 | Winslow et al. |
| 2010/0030272 A1 | 2/2010 | Winslow et al. |
| 2010/0030283 A1 | 2/2010 | King et al. |
| 2010/0036417 A1 | 2/2010 | James et al. |
| 2010/0036422 A1 | 2/2010 | Flynn et al. |
| 2010/0036423 A1 | 2/2010 | Hayes et al. |
| 2010/0036425 A1 | 2/2010 | Barrus et al. |
| 2010/0036432 A1 | 2/2010 | Ely |
| 2010/0036443 A1 | 2/2010 | Hutton et al. |
| 2010/0042149 A1 | 2/2010 | Chao et al. |
| 2010/0042152 A1 | 2/2010 | Semler et al. |
| 2010/0042155 A1 | 2/2010 | Biedermann et al. |
| 2010/0042156 A1 | 2/2010 | Harms et al. |
| 2010/0057125 A1 | 3/2010 | Viker |
| 2010/0057126 A1 | 3/2010 | Hestad |
| 2010/0057131 A1 | 3/2010 | Ely |
| 2010/0063544 A1 | 3/2010 | Butler |
| 2010/0063545 A1 | 3/2010 | Richelsoph |
| 2010/0063546 A1 | 3/2010 | Miller et al. |
| 2010/0063547 A1 | 3/2010 | Morin et al. |
| 2010/0063550 A1 | 3/2010 | Felix et al. |
| 2010/0063552 A1 | 3/2010 | Chin et al. |
| 2010/0069919 A1 | 3/2010 | Carls et al. |
| 2010/0069969 A1 | 3/2010 | Ampuero et al. |
| 2010/0082066 A1 | 4/2010 | Biyani |
| 2010/0087858 A1 | 4/2010 | Abdou |
| 2010/0087862 A1 | 4/2010 | Biedermann et al. |
| 2010/0087863 A1 | 4/2010 | Biedermann et al. |
| 2010/0087864 A1 | 4/2010 | Klein et al. |
| 2010/0087865 A1 | 4/2010 | Biedermann et al. |
| 2010/0094343 A1 | 4/2010 | Pham et al. |
| 2010/0094348 A1 | 4/2010 | Biedermann et al. |
| 2010/0094349 A1 | 4/2010 | Hammer et al. |
| 2010/0094352 A1 | 4/2010 | Iott et al. |
| 2010/0094353 A1 | 4/2010 | Shim et al. |
| 2010/0100136 A1 | 4/2010 | Won et al. |
| 2010/0100137 A1 | 4/2010 | Justis et al. |
| 2010/0106189 A1 | 4/2010 | Miller |
| 2010/0106192 A1 | 4/2010 | Barry |
| 2010/0114165 A1 | 5/2010 | Ely |
| 2010/0114170 A1 | 5/2010 | Barrus et al. |
| 2010/0114171 A1 | 5/2010 | Boachie-Adjei et al. |
| 2010/0114179 A1 | 5/2010 | Moore et al. |
| 2010/0114180 A1 | 5/2010 | Rock et al. |
| 2010/0114182 A1 | 5/2010 | Wilcox et al. |
| 2010/0121386 A1 | 5/2010 | Peultier et al. |
| 2010/0125302 A1 | 5/2010 | Hammill, Sr. et al. |
| 2010/0137908 A1 | 6/2010 | Zhang |
| 2010/0137912 A1 | 6/2010 | Alcock et al. |
| 2010/0137918 A1 | 6/2010 | Wilcox et al. |
| 2010/0137920 A1 | 6/2010 | Hammill, Sr. et al. |
| 2010/0152776 A1 | 6/2010 | Keyer et al. |
| 2010/0152785 A1 | 6/2010 | Forton et al. |
| 2010/0160965 A1 | 6/2010 | Viker |
| 2010/0160967 A1 | 6/2010 | Capozzoli |
| 2010/0160968 A1 | 6/2010 | Joshi et al. |
| 2010/0160974 A1 | 6/2010 | Viker |
| 2010/0160976 A1 | 6/2010 | Biedermann et al. |
| 2010/0168796 A1 | 7/2010 | Eliasen et al. |
| 2010/0168800 A1 | 7/2010 | Biedermann et al. |
| 2010/0168801 A1 | 7/2010 | Biedermann et al. |
| 2010/0168803 A1 | 7/2010 | Hestad et al. |
| 2010/0174322 A1 | 7/2010 | Abdelgany et al. |
| 2010/0179602 A1 | 7/2010 | Dauster et al. |
| 2010/0191293 A1 | 7/2010 | Jackson |
| 2010/0204735 A1 | 8/2010 | Gephart et al. |
| 2010/0211104 A1 | 8/2010 | Moumene et al. |
| 2010/0211105 A1 | 8/2010 | Moumene et al. |
| 2010/0211114 A1 | 8/2010 | Jackson |
| 2010/0222822 A1 | 9/2010 | Farris et al. |
| 2010/0222828 A1 | 9/2010 | Stad et al. |
| 2010/0234902 A1 | 9/2010 | Biedermann et al. |
| 2010/0249843 A1 | 9/2010 | Wegzyn, III |
| 2010/0249846 A1 | 9/2010 | Simonson |
| 2010/0249856 A1 | 9/2010 | Iott et al. |
| 2010/0262185 A1 | 10/2010 | Gelfand et al. |
| 2010/0262187 A1 | 10/2010 | Marik et al. |
| 2010/0262190 A1 | 10/2010 | Ballard et al. |
| 2010/0262191 A1 | 10/2010 | Marik et al. |
| 2010/0262192 A1 | 10/2010 | Foley |
| 2010/0274285 A1 | 10/2010 | Rouleau |
| 2010/0274287 A1 | 10/2010 | Rouleau et al. |
| 2010/0274288 A1 | 10/2010 | Prevost et al. |
| 2010/0298891 A1 | 11/2010 | Jackson |
| 2010/0305621 A1 | 12/2010 | Wang et al. |
| 2010/0312288 A1 | 12/2010 | Hammill, Sr. et al. |
| 2010/0331885 A1 | 12/2010 | Remington et al. |
| 2011/0004256 A1 | 1/2011 | Biedermann et al. |
| 2011/0009906 A1 | 1/2011 | Hestad et al. |
| 2011/0009911 A1 | 1/2011 | Hammill et al. |
| 2011/0029022 A1 | 2/2011 | Zehnder et al. |
| 2011/0040338 A1 | 2/2011 | Jackson |
| 2011/0046683 A1 | 2/2011 | Biedermann et al. |
| 2011/0093015 A1 | 4/2011 | Ramsay et al. |
| 2011/0093021 A1 | 4/2011 | Fanger et al. |
| 2011/0106174 A1 | 5/2011 | Rezach |
| 2011/0106175 A1 | 5/2011 | Rezach |
| 2011/0130792 A1 | 6/2011 | Nydegger et al. |
| 2011/0152939 A1 | 6/2011 | Aldridge |
| 2011/0152949 A1 | 6/2011 | Biedermann et al. |
| 2011/0160778 A1 | 6/2011 | Elsbury |
| 2011/0166610 A1 | 7/2011 | Altarac et al. |
| 2011/0178558 A1 | 7/2011 | Barry |
| 2011/0178560 A1 | 7/2011 | Butler et al. |
| 2011/0184469 A1 | 7/2011 | Ballard et al. |
| 2011/0184471 A1 | 7/2011 | Foley et al. |
| 2011/0190822 A1 | 8/2011 | Spitler et al. |
| 2011/0196430 A1 | 8/2011 | Walsh |
| 2011/0202094 A1 | 8/2011 | Pereira et al. |
| 2011/0202095 A1 | 8/2011 | Semler et al. |
| 2011/0230915 A1 | 9/2011 | Anderson et al. |
| 2011/0238119 A1 | 9/2011 | Moumene et al. |
| 2011/0251644 A1 | 10/2011 | Hestad et al. |
| 2011/0257685 A1 | 10/2011 | Hay et al. |
| 2011/0257687 A1 | 10/2011 | Trieu et al. |
| 2011/0257689 A1 | 10/2011 | Fiechter et al. |
| 2011/0257690 A1 | 10/2011 | Rezach |
| 2011/0263945 A1 | 10/2011 | Peterson et al. |
| 2011/0313460 A1 | 12/2011 | Mclean et al. |
| 2011/0313463 A1 | 12/2011 | McLean |
| 2011/0313471 A1 | 12/2011 | McLean et al. |
| 2012/0029568 A1 | 2/2012 | Jackson |
| 2012/0046699 A1 | 2/2012 | Jones et al. |

(56) References Cited

U.S. PATENT DOCUMENTS

| | | | |
|---|---|---|---|
| 2012/0053636 | A1 | 3/2012 | Schmocker |
| 2012/0078307 | A1 | 3/2012 | Nihalani |
| 2012/0197314 | A1 | 8/2012 | Farris |
| 2012/0232598 | A1 | 9/2012 | Hestad et al. |
| 2012/0310284 | A1 | 12/2012 | Gerchow |
| 2013/0103097 | A1 | 4/2013 | May et al. |

FOREIGN PATENT DOCUMENTS

| | | |
|---|---|---|
| DE | 3630863 | 3/1988 |
| DE | G9202745.8 | 4/1992 |
| DE | 4425392 | 11/1995 |
| DE | 29806563 | 6/1998 |
| DE | 29810798 | 12/1999 |
| DE | 19951145 | 5/2001 |
| DE | 102007055745 | 7/2008 |
| EP | 0195455 | 9/1986 |
| EP | 0172130 | 2/1987 |
| EP | 0276153 | 7/1988 |
| EP | 0667127 | 8/1995 |
| EP | 0669109 | 8/1995 |
| EP | 0677277 | 10/1995 |
| EP | 1277444 | 1/2003 |
| EP | 2082709 | 7/2009 |
| EP | 2468198 | 12/2010 |
| ES | 2384773 | 7/2012 |
| FR | 2467312 | 4/1981 |
| FR | 2715825 | 8/1995 |
| FR | 2717370 | 9/1995 |
| FR | 2718946 | 10/1995 |
| FR | 2799949 | 4/2001 |
| FR | 2814936 | 4/2002 |
| FR | 2815535 | 4/2002 |
| FR | 2856578 | 6/2003 |
| FR | 2865377 | 1/2004 |
| FR | 2846233 | 4/2004 |
| FR | 2857850 | 4/2004 |
| FR | 2925288 | 6/2009 |
| GB | 203508 | 9/1923 |
| GB | 2082709 | 3/1982 |
| GB | 2140523 | 11/1984 |
| GB | 2365345 | 2/2002 |
| GB | 2382304 | 5/2003 |
| JP | S4867159 | 9/1973 |
| JP | S50106061 | 8/1975 |
| JP | H10277070 | 10/1998 |
| JP | 2000325358 | 3/2000 |
| JP | 2002052030 | 2/2002 |
| JP | 2002221218 | 8/2002 |
| SU | 371359 | 2/1973 |
| WO | 8909030 | 10/1989 |
| WO | 8912431 | 12/1989 |
| WO | 9116018 | 10/1991 |
| WO | 9116020 | 10/1991 |
| WO | 9203100 | 3/1992 |
| WO | 9321848 | 11/1993 |
| WO | 9325161 | 12/1993 |
| WO | 9410927 | 5/1994 |
| WO | 9410944 | 5/1994 |
| WO | 9426191 | 11/1994 |
| WO | 9428824 | 12/1994 |
| WO | 9501132 | 1/1995 |
| WO | 9513755 | 5/1995 |
| WO | 9528889 | 11/1995 |
| WO | 9531947 | 11/1995 |
| WO | 9535067 | 12/1995 |
| WO | 9606576 | 3/1996 |
| WO | 9621396 | 7/1996 |
| WO | 9625104 | 8/1996 |
| WO | 9628105 | 9/1996 |
| WO | 9628118 | 9/1996 |
| WO | 9641582 | 12/1996 |
| WO | 9714366 | 4/1997 |
| WO | 9714368 | 4/1997 |
| WO | 9727812 | 8/1997 |
| WO | 9730649 | 8/1997 |
| WO | 9737604 | 10/1997 |
| WO | 9737605 | 10/1997 |
| WO | 9812977 | 4/1998 |
| WO | 9815233 | 4/1998 |
| WO | 9825534 | 6/1998 |
| WO | 9832386 | 7/1998 |
| WO | 9834554 | 8/1998 |
| WO | 9834556 | 8/1998 |
| WO | 9838924 | 9/1998 |
| WO | 9903415 | 1/1999 |
| WO | 9905980 | 2/1999 |
| WO | 9932084 | 7/1999 |
| WO | 9938463 | 8/1999 |
| WO | 9947083 | 9/1999 |
| WO | 9949802 | 10/1999 |
| WO | 0015125 | 3/2000 |
| WO | 0022997 | 4/2000 |
| WO | 0027297 | 5/2000 |
| WO | 0072769 | 7/2000 |
| WO | 0065268 | 11/2000 |
| WO | 0066045 | 11/2000 |
| WO | 0106940 | 2/2001 |
| WO | 0108574 | 2/2001 |
| WO | 0110317 | 2/2001 |
| WO | 0115612 | 3/2001 |
| WO | 0122893 | 4/2001 |
| WO | 0128435 | 4/2001 |
| WO | 0128436 | 4/2001 |
| WO | 0145576 | 6/2001 |
| WO | 0149191 | 7/2001 |
| WO | 0158370 | 8/2001 |
| WO | 0167972 | 9/2001 |
| WO | 0167974 | 9/2001 |
| WO | 0222030 | 3/2002 |
| WO | 0234150 | 5/2002 |
| WO | 02054966 | 7/2002 |
| WO | 02102259 | 12/2002 |
| WO | 03007828 | 1/2003 |
| WO | 03026523 | 4/2003 |
| WO | 03037199 | 5/2003 |
| WO | 03047442 | 6/2003 |
| WO | 03068083 | 8/2003 |
| WO | 03068088 | 8/2003 |
| WO | 03084415 | 10/2003 |
| WO | 03094699 | 11/2003 |
| WO | 2004021900 | 3/2004 |
| WO | 2004022108 | 3/2004 |
| WO | 2004041100 | 5/2004 |
| WO | 2004075778 | 9/2004 |
| WO | 2004089245 | 10/2004 |
| WO | 2004098452 | 11/2004 |
| WO | 2004105577 | 12/2004 |
| WO | 2004107997 | 12/2004 |
| WO | 2005000136 | 1/2005 |
| WO | 2005000137 | 1/2005 |
| WO | 2005013839 | 2/2005 |
| WO | 2005018466 | 3/2005 |
| WO | 2005018471 | 3/2005 |
| WO | 2005020829 | 3/2005 |
| WO | 2005030068 | 4/2005 |
| WO | 2005065374 | 7/2005 |
| WO | 2005072632 | 8/2005 |
| WO | 2005082262 | 9/2005 |
| WO | 2005087121 | 9/2005 |
| WO | 2005099400 | 10/2005 |
| WO | 2005102195 | 11/2005 |
| WO | 2005104969 | 11/2005 |
| WO | 2006005198 | 1/2006 |
| WO | 2006017616 | 2/2006 |
| WO | 2006020530 | 2/2006 |
| WO | 2006042188 | 4/2006 |
| WO | 2006047711 | 5/2006 |
| WO | 2006054111 | 5/2006 |
| WO | 2006065607 | 6/2006 |
| WO | 2006066685 | 6/2006 |
| WO | 2006068711 | 6/2006 |
| WO | 2006071742 | 7/2006 |

(56) References Cited

FOREIGN PATENT DOCUMENTS

| | | |
|---|---|---|
| WO | 2006079531 | 8/2006 |
| WO | 2006096240 | 9/2006 |
| WO | 2006096351 | 9/2006 |
| WO | 2006104874 | 10/2006 |
| WO | 2006110463 | 10/2006 |
| WO | 2006116437 | 11/2006 |
| WO | 2006119447 | 11/2006 |
| WO | 2007002409 | 1/2007 |
| WO | 2007038350 | 4/2007 |
| WO | 2007040750 | 4/2007 |
| WO | 2007040888 | 4/2007 |
| WO | 2007041702 | 4/2007 |
| WO | 2007053566 | 5/2007 |
| WO | 2007060534 | 5/2007 |
| WO | 2007075454 | 7/2007 |
| WO | 2007081849 | 8/2007 |
| WO | 2007087469 | 8/2007 |
| WO | 2007087628 | 8/2007 |
| WO | 2007090021 | 8/2007 |
| WO | 2007092056 | 8/2007 |
| WO | 2007092870 | 8/2007 |
| WO | 2007097905 | 8/2007 |
| WO | 2007109470 | 9/2007 |
| WO | 2007114834 | 10/2007 |
| WO | 2007118045 | 10/2007 |
| WO | 2007121030 | 10/2007 |
| WO | 2007121057 | 10/2007 |
| WO | 2007121271 | 10/2007 |
| WO | 2007123920 | 11/2007 |
| WO | 2007124222 | 11/2007 |
| WO | 2007124249 | 11/2007 |
| WO | 2007127595 | 11/2007 |
| WO | 2007127604 | 11/2007 |
| WO | 2007130835 | 11/2007 |
| WO | 2007130840 | 11/2007 |
| WO | 2007130941 | 11/2007 |
| WO | 2007138270 | 12/2007 |
| WO | 2007146032 | 12/2007 |
| WO | 2008005740 | 1/2008 |
| WO | 2008006098 | 1/2008 |
| WO | 2008008511 | 1/2008 |
| WO | 2008013892 | 1/2008 |
| WO | 2008027860 | 3/2008 |
| WO | 2008033742 | 3/2008 |
| WO | 2008036975 | 3/2008 |
| WO | 2008037256 | 4/2008 |
| WO | 2008039777 | 4/2008 |
| WO | 2008042948 | 4/2008 |
| WO | 2008048923 | 4/2008 |
| WO | 2008048953 | 4/2008 |
| WO | 2008051737 | 4/2008 |
| WO | 2008069420 | 6/2008 |
| WO | 2008070716 | 6/2008 |
| WO | 2008134703 | 6/2008 |
| WO | 2008078163 | 7/2008 |
| WO | 2008082737 | 7/2008 |
| WO | 2008100590 | 8/2008 |
| WO | 2008118295 | 10/2008 |
| WO | 2008119006 | 10/2008 |
| WO | 2008124772 | 10/2008 |
| WO | 2008140756 | 11/2008 |
| WO | 2008157589 | 12/2008 |
| WO | 2009003153 | 12/2008 |
| WO | 2009006225 | 1/2009 |
| WO | 2009011845 | 1/2009 |
| WO | 2009014540 | 1/2009 |
| WO | 2009015100 | 1/2009 |
| WO | 2009018086 | 2/2009 |
| WO | 2009029928 | 3/2009 |
| WO | 2009055028 | 4/2009 |
| WO | 2009055400 | 4/2009 |
| WO | 2009055407 | 4/2009 |
| WO | 2009152302 | 12/2009 |
| WO | 2009155360 | 12/2009 |
| WO | 2010017631 | 2/2010 |
| WO | 2010018316 | 2/2010 |
| WO | 2010018317 | 2/2010 |
| WO | 2010019857 | 2/2010 |
| WO | 2010030916 | 3/2010 |
| WO | 2010045383 | 4/2010 |
| WO | 2010065648 | 6/2010 |
| WO | 2010078901 | 7/2010 |
| WO | 2010111500 | 9/2010 |
| WO | 2010120989 | 10/2010 |
| WO | 2010147639 | 12/2010 |
| WO | 2011043805 | 4/2011 |
| WO | 2011068818 | 6/2011 |
| WO | 2012033532 | 3/2012 |
| WO | 2012075827 | 6/2012 |
| WO | 2012088890 | 7/2012 |

OTHER PUBLICATIONS

Claris Instrumentation Brochure, G Med, pub. 1997.
EBI Omega 21 Brochure, EBI Spine Systems, pub. 1999.
SDRS Surgical Dynamics Rod System Brochure, Surgical Dynamics, pub. 1998-99.
Spine, Lipcott, Williams & Wilkins, Inc. vol. 24, No. 15, p. 1495.
The Rod Plate System Brochure, Stryker Howmedica Osteonics, pub. Oct. 1999.
Versalok Low Back Fixation System Brochure, Wright Medical Technology, Inc., pub. 1997.
VLS System Variable Locking Screw Brochure, Interpore Cross International, 1999.
Brochure of DePuy Spine on Surgical Technique, Published 2004, pp. 1-36.

* cited by examiner

Fig. 1.
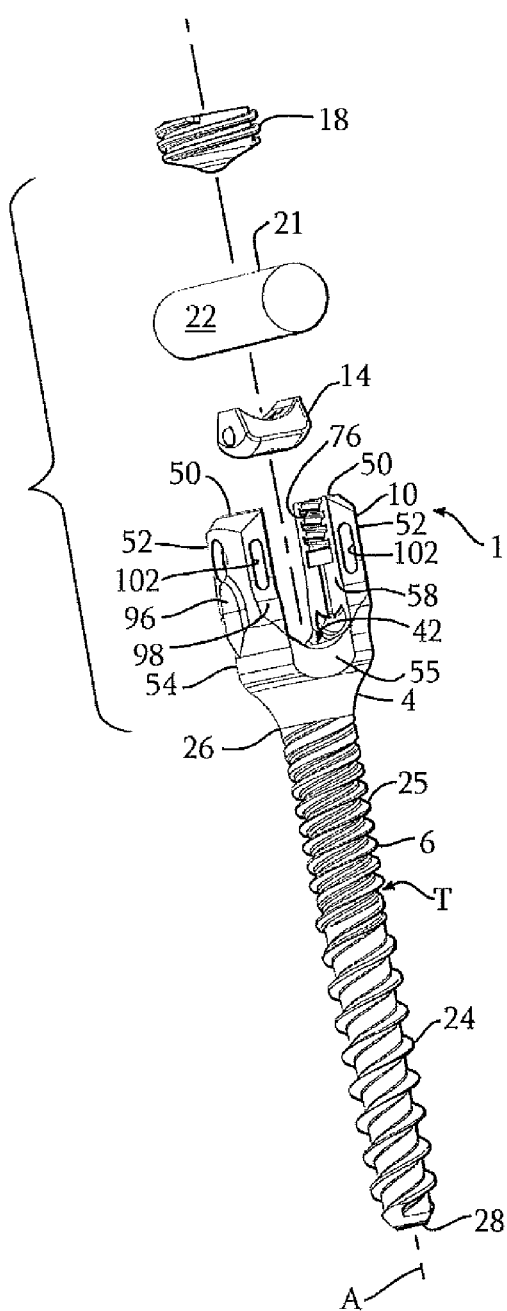
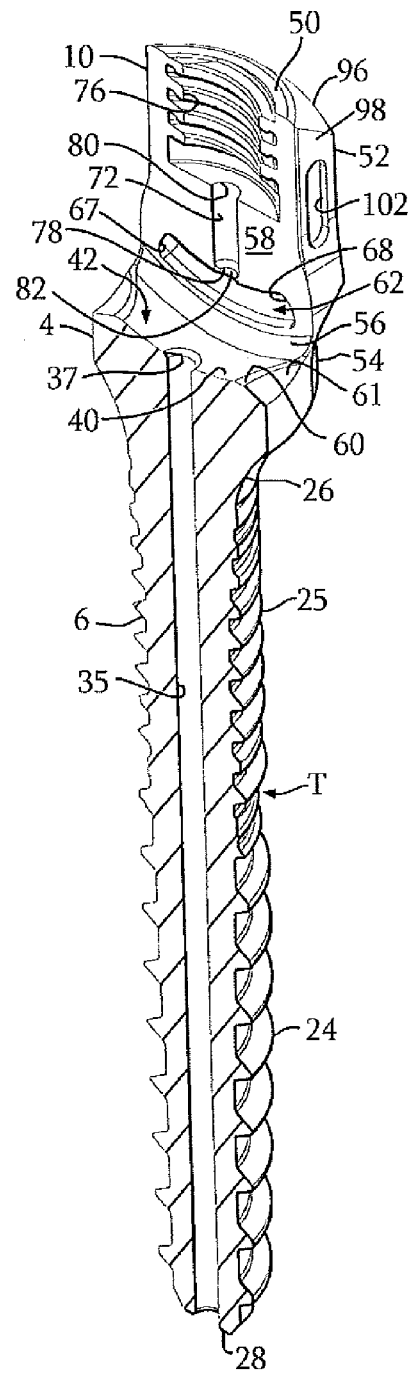
Fig. 2.

Fig. 7.
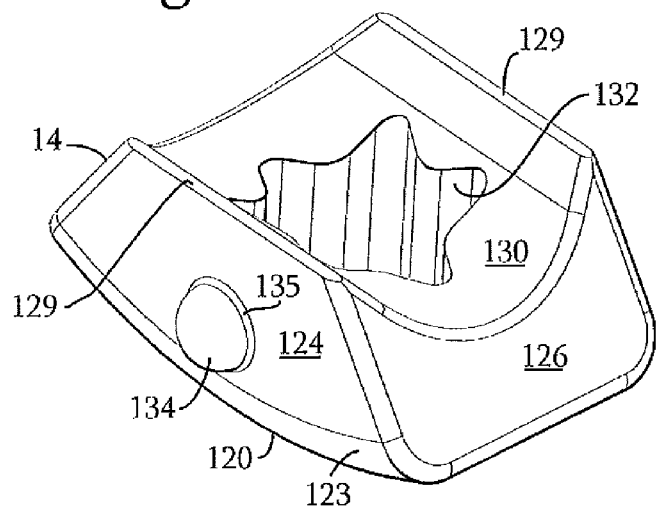
Fig. 8.
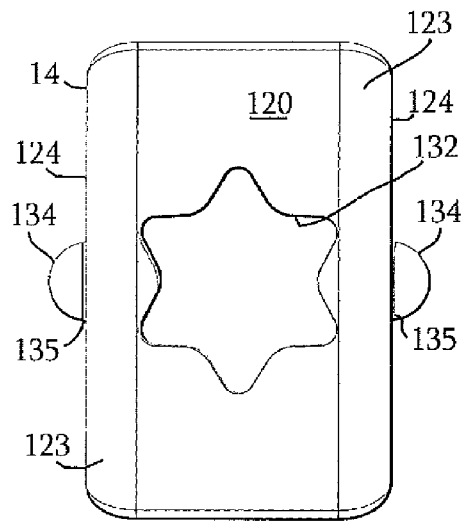
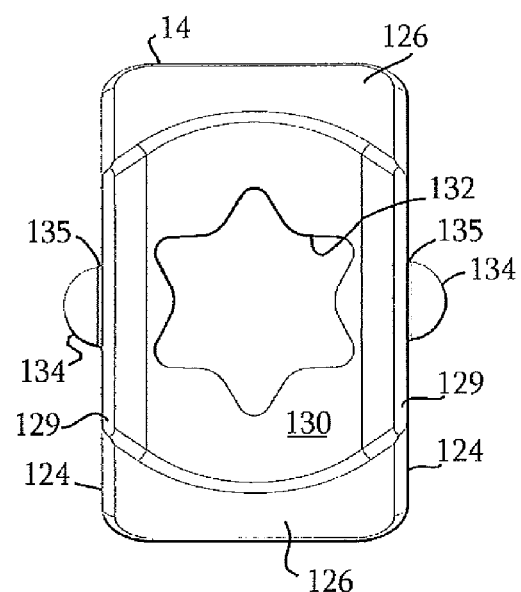
Fig. 9.

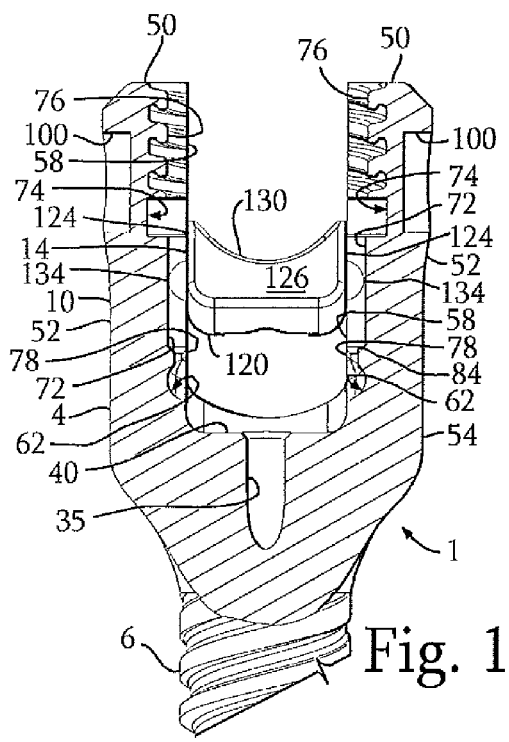
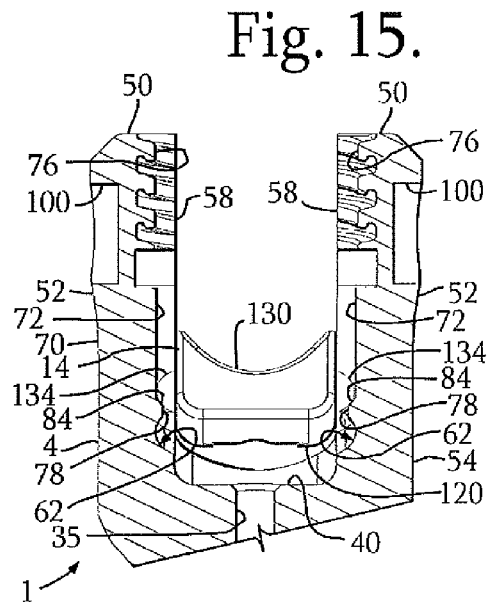
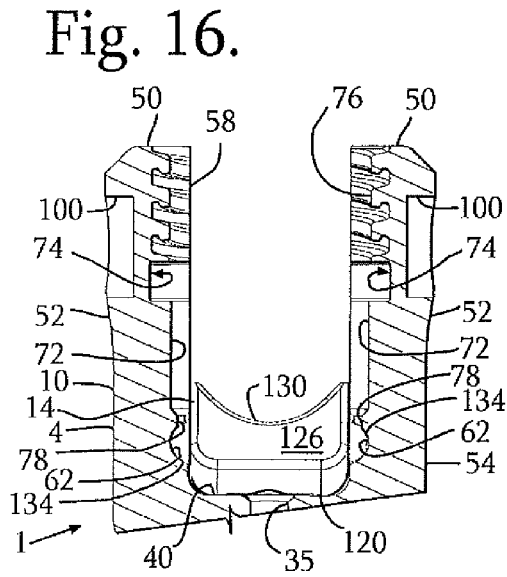
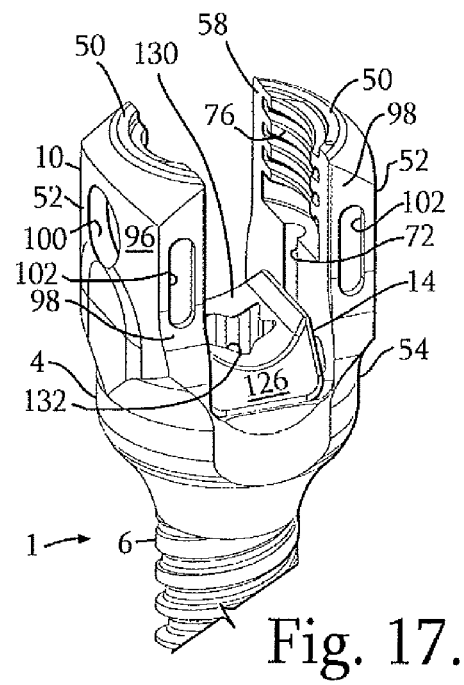

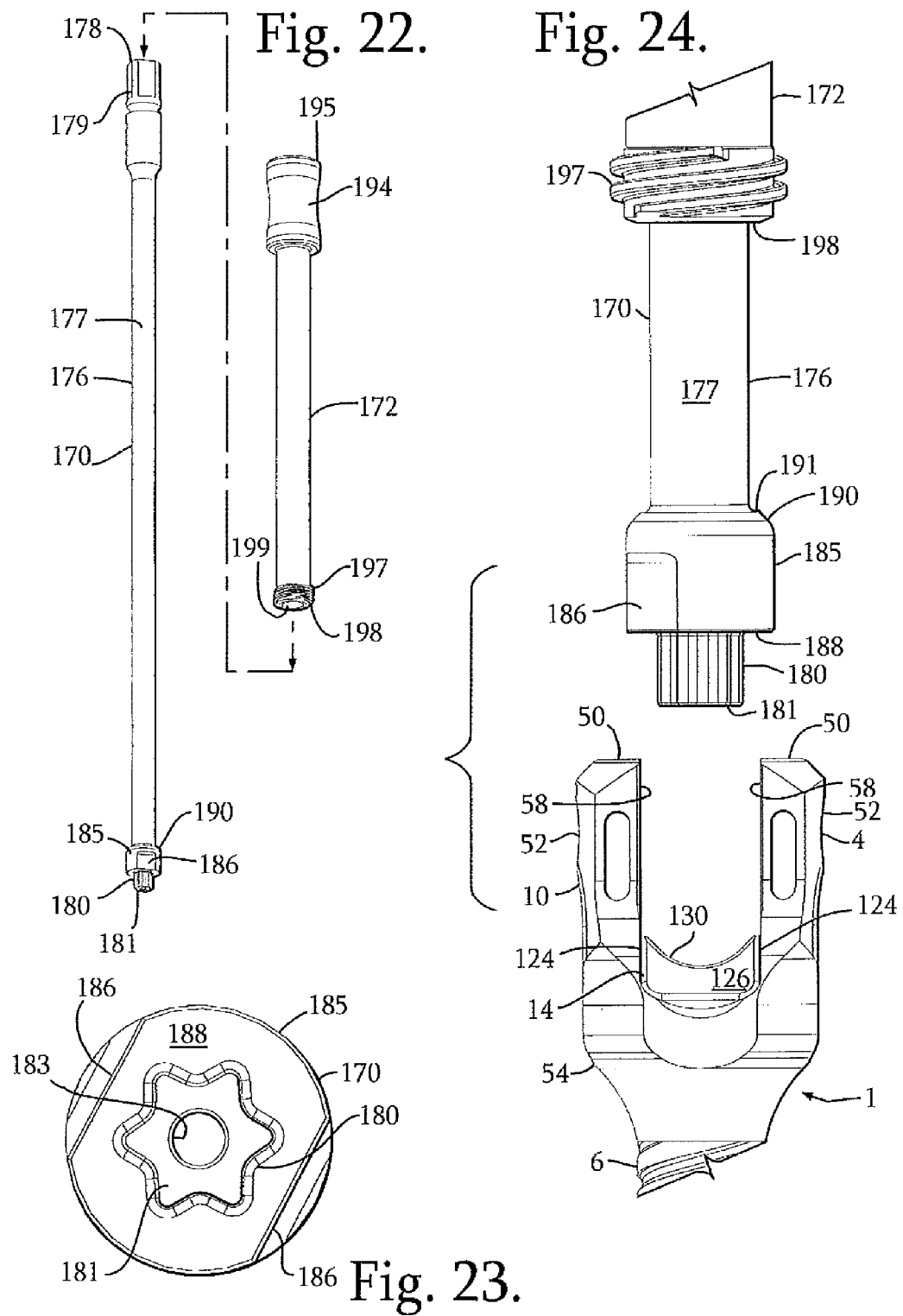

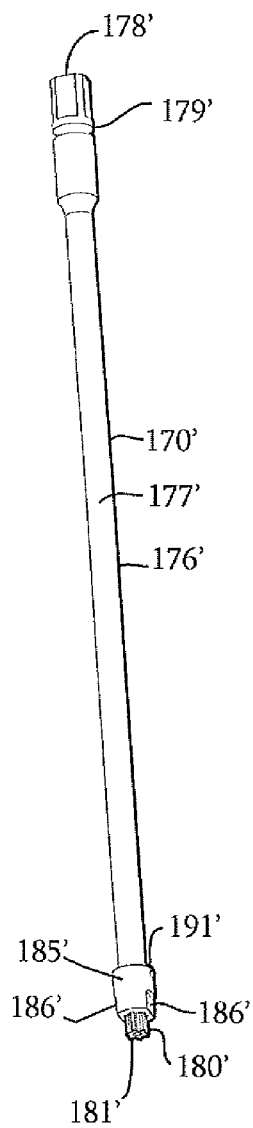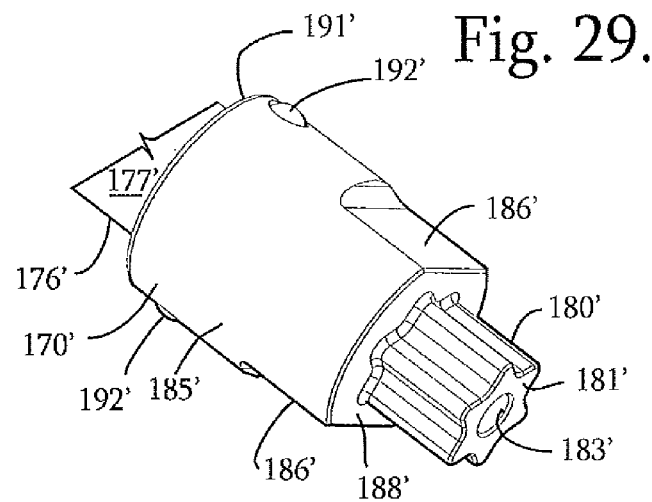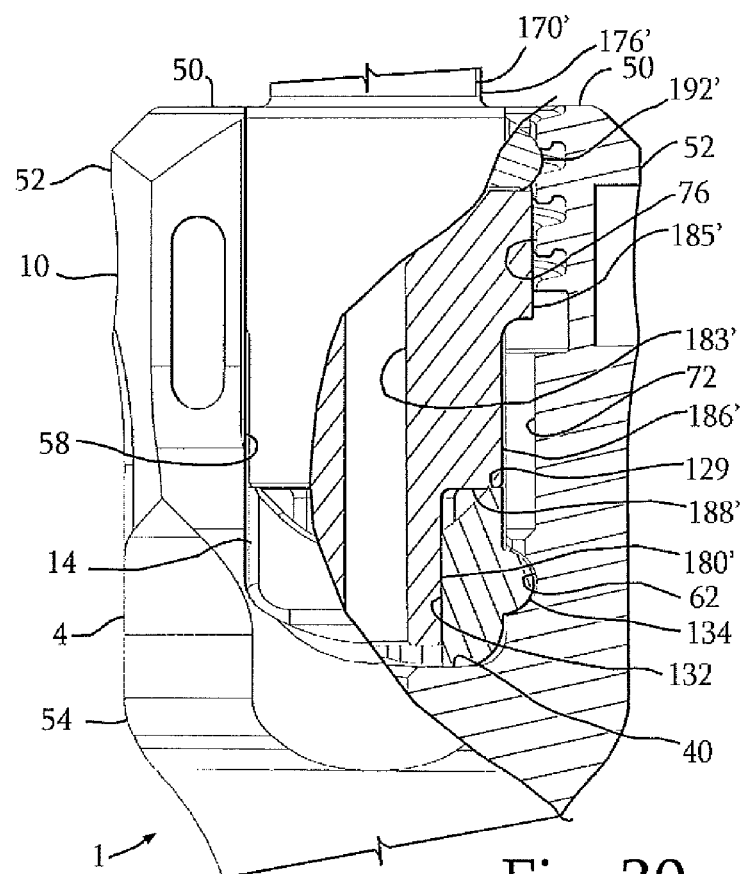

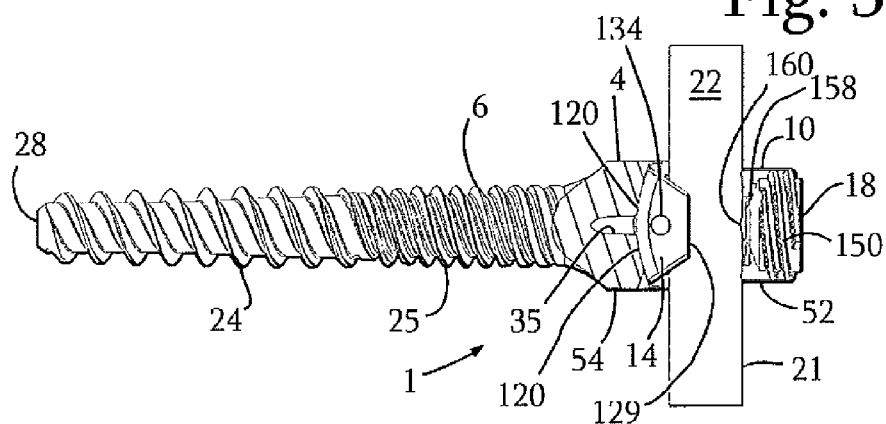
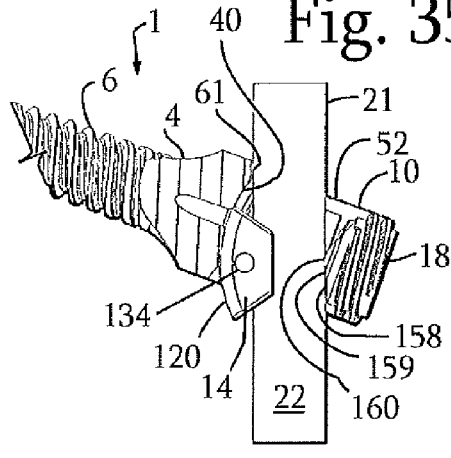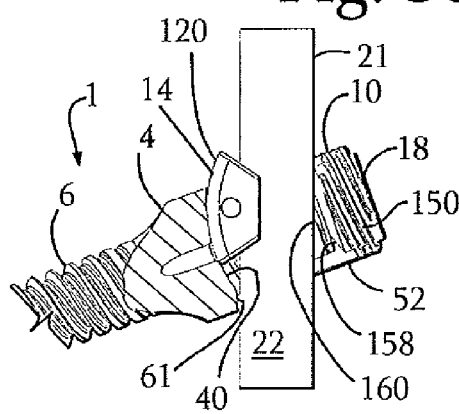
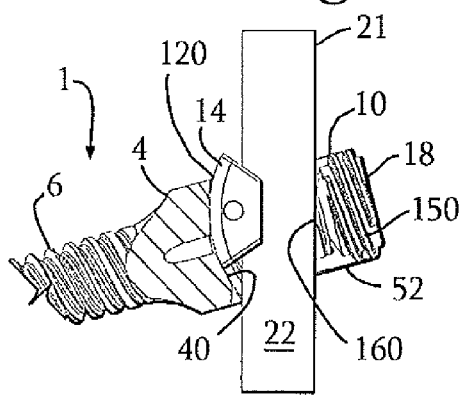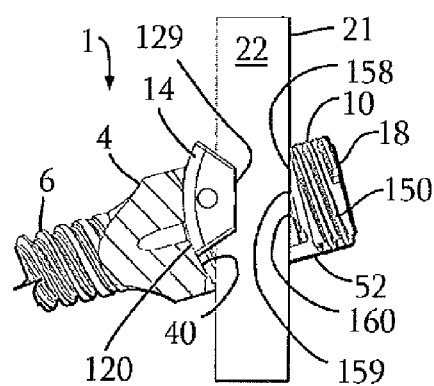

US 8,852,239 B2

SAGITTAL ANGLE SCREW WITH INTEGRAL SHANK AND RECEIVER

CROSS-REFERENCE TO RELATED APPLICATIONS

This application claims the benefit of U.S. Provisional Patent Application Ser. No. 61/850,500 filed Feb. 15, 2013, the disclosure of which is incorporated by reference herein in its entirety.

BACKGROUND OF THE INVENTION

The present invention is directed to bone anchors for use in spinal surgery and particularly to threaded bone screws having angular movement in a single plane.

Bone screws are utilized in many types of spinal surgery in order to secure various implants to vertebrae along the spinal column for the purpose of stabilizing and/or adjusting spinal alignment. Although both closed-ended and open-ended bone screws are known, open-ended screws are particularly well suited for connections to rods and connector arms, because such rods or arms do not need to be passed through a closed bore, but rather can be laid or urged into an open channel within a receiver or head of such a screw. Generally, the screws must be inserted into the bone as an integral unit along with the head, or as a preassembled unit in the form of a shank and pivotal receiver, such as a polyaxial bone screw assembly.

Typical open-ended bone screws include a threaded shank with a pair of parallel projecting branches or arms which form a yoke with a U-shaped slot or channel to receive a rod. Hooks and other types of connectors, as are used in spinal fixation techniques, may also include similar open ends for receiving rods or portions of other fixation and stabilization structure.

A common approach for providing vertebral column support is to implant bone screws into certain bones which then in turn support a longitudinal structure such as a rod, or are supported by such a rod. Bone screws of this type typically have a fixed head or receiver relative to a shank thereof, or may be of a polyaxial screw nature. In the fixed bone screws, the rod receiver head cannot be moved relative to the shank and the rod must be favorably positioned in order for it to be placed within the receiver head. This is sometimes very difficult or impossible to do. Therefore, polyaxial bone screws that provide a ball-and-socket-like joint between a rod receiving bone screw head and associated shank are commonly preferred. However in certain applications, polyaxial screws provide a range of motion that is too great, such as, for example, in the treatment of certain spinal deformities, such as scoliosis, wherein surgical rotation or de-rotation manipulations may be required to correct an undesirable rotation of the vertebrae occurring in combination with a lateral spinal curvature.

SUMMARY OF THE INVENTION

A spinal bone screw shank of a bone screw assembly embodiment of the invention is pivotable in a single plane with respect to an attached longitudinal connecting member. The bone screw includes a threaded shank that is integral with a receiver or head of the bone screw. The receiver includes a pair of spaced upstanding arms forming a channel sized and shaped for receiving a longitudinal connecting member, such as a rod, and having a cavity communicating with the channel, the cavity partially defined by a partially cylindrical seating surface, the surface further defined by a radius that originates at a pivot axis spaced from the bottom surface. The receiver arms include opposed inner surfaces, each surface having an arcuate aperture that also generally follows one or more radii originating at the pivot axis. A discrete insert is located within the receiver cavity, the insert having a bottom surface in sliding engagement with the receiver seating surface. The insert further includes a pair of outwardly extending projections, each projection slidingly captured within one of the receiver arcuate apertures. The insert includes an upper seat sized and shaped for closely receiving the rod. During use, a rod that frictionally engages the insert is in a pivotal relationship with the bone screw shank due to the sliding movement of the insert with respect to the bone screw receiver, such movement and bone screw pivoting advantageously limited to a single plane, which, when the bone screw is implanted into a vertebra, the bone screw is oriented so that the pivotal relationship is in a sagittal plane.

Objects of the invention include providing apparatus and methods that are easy to use and especially adapted for the intended use thereof and wherein the tools are comparatively inexpensive to produce. Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 1 is an exploded perspective view of a bone anchor assembly, shown with a longitudinal connecting member in the form of a rod and with a closure structure, the assembly including a bone screw having a shank and an integral receiver portion or head that forms a channel for receiving the rod and an insert also received by the receiver and slidable with respect to the receiver in a single plane.

FIG. 2 is an enlarged perspective view of the bone screw of FIG. 1 with portions broken away to show the detail thereof.

FIG. 7 is an enlarged perspective view of the insert of FIG. 1.

FIG. 8 is a bottom plan view of the insert of FIG. 7.

FIG. 9 is a top plan view of the insert of FIG. 7.

FIG. 14 is an enlarged and partial front elevational view of the bone screw of FIG. 1 with portions broken away to show the detail thereof and shown in an early stage of assembly with the insert of FIG. 1, also in enlarged front elevation.

FIG. 15 is a partial front elevational view with portions broken away of the bone screw and insert of FIG. 14, showing the insert in a subsequent stage of assembly with the receiver of the bone screw.

FIG. 16 is a partial front elevational view with portions broken away of the bone screw and insert of FIG. 15, showing the insert in a subsequent stage of assembly with the receiver of the bone screw.

FIG. 17 is a partial perspective view of the bone screw and assembled insert of FIG. 16.

FIG. 22 is an exploded perspective view of a driving tool for use with the bone screw assembly of FIG. 1, the driving tool having an inner driver and an outer locking sleeve.

FIG. 23 is an enlarged bottom plan view of the inner driver of FIG. 22.

FIG. 24 is an enlarged and partial front elevational view of the driving tool of FIG. 22 shown assembled and also shown with the bone screw and attached insert of FIG. 17, also in enlarged and partial front elevation, prior to alignment of the inner driver with the insert.

FIG. 28 is a perspective view of an alternative driving/manipulation tool for use with the assembly of FIG. 1.

FIG. 29 is an enlarged and partial perspective view of the tool of FIG. 28.

FIG. 30 is an enlarged and partial front elevational view with portions broken away of the tool of FIG. 28 and also of the bone screw and attached insert of FIG. 17, also shown in enlarged front elevation with portions broken away, the tool shown engaged with the insert.

FIG. 34 is a side elevational view of the bone screw, insert, rod and closure structure assembly of FIG. 1, the bone screw shown with portions broken away to show the detail of the assembly, the closure structure shown in an un-locked position allowing for pivot of the bone screw with respect to the insert and the rod in a sagittal plane, the bone screw shown in a neutral or zero degree pivot with respect to the insert and the rod.

FIG. 35 is a partial side elevational view with portions broken away of the assembly of FIG. 34 but with the bone screw shown pivoted to an angle with respect to the rod that represents about twenty degrees in a cephalic direction.

FIG. 36 is a partial side elevational view with portions broken away of the assembly of FIG. 34 but with the bone screw shown pivoted to about twenty degrees caudal.

FIG. 37 is a partial side elevational view with portions broken away of the assembly of FIG. 34 with the bone screw shown pivoted to about fifteen degrees caudal.

FIG. 38 is a partial side elevational view with portions broken away of the assembly of FIG. 37 and shown with the closure structure in locked frictional engagement with the rod, fixing the angle of the bone screw with respect to the rod.

DETAILED DESCRIPTION OF THE INVENTION

Figure 3:
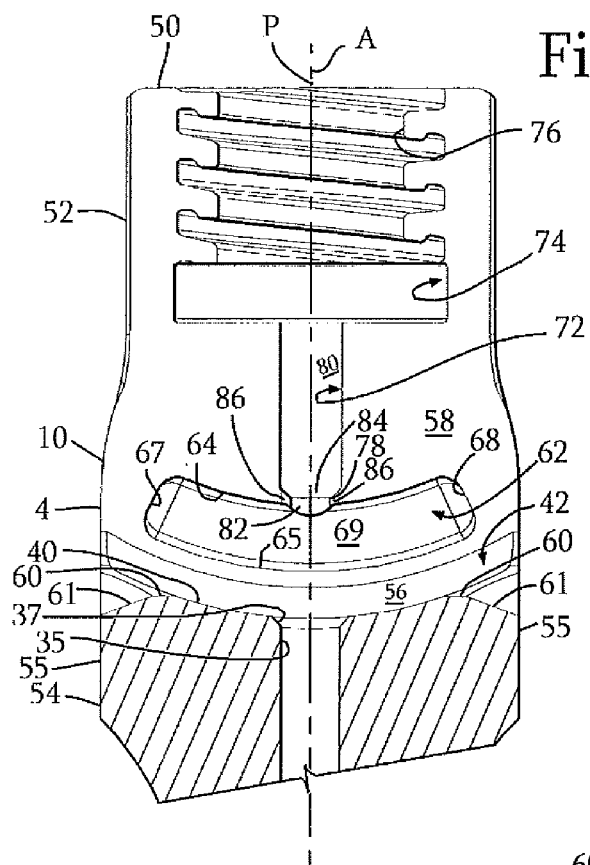
FIG. 3 is an enlarged and partial side elevational view of the bone screw of FIG. 2 with portions broken away to show the detail thereof.

As required, detailed embodiments are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. It is also noted that any reference to the words top, bottom, up and down, and the like, in this application refers to the alignment shown in the various drawings, as well as the normal connotations applied to such devices, and is not intended to restrict positioning of the bone attachment structures in actual use.

Furthermore, the terms lead, pitch and start, as such terms are used to describe helically wound guide and advancement structures, are to be understood as follows: Lead is a distance along the axis of a closure plug, bone screw or other cylindrical body that is covered by one complete rotation (360 degrees) of the plug, screw or other body. Pitch is the distance from a crest (or outer point or location) of one guide and advancement structure form to the next. For example in a single-start thread-form, such as a single start, helically wound v-thread, lead and pitch are the same. Single start means that there is only one ridge or helically wound form wrapped around a cylindrical core and thus there is only one start structure or surface at a base or forward end of the body. For example, each time a single start closure rotates one turn (360 degrees), the closure has advanced axially by a width of one ridge or one helical form. Double-start means that there are two ridges or forms wrapped around a core body and thus there are two starting surfaces or structures on the body. Therefore, each time a double-start threaded (or having a non-threaded, flange form structure) cylindrical body rotates one turn (360 degrees), such a body has advanced axially by a width of two ridges or forms. Multi-start means that there are at least two and may be up to three or more of such ridges or forms wrapped around a core body.

With reference to FIGS. 1-42, the reference number 1 generally represents an open implant in the form of a uni-planar or single plane pivot bone anchor apparatus or assembly that includes a bone screw 4, that further includes a shank or body 6 integral with a rod or other longitudinal connector receiving portion, hereafter identified as a receiver or head 10; an insert 14 located within the receiver portion of the integral bone screw 4 and slidable on an arcuate track formed in the receiver 10; and a multi-start closure structure or top 18 having a double-start helically wound flange-form. However, it is foreseen that the closure structure 18 may also be single start and have other threaded or non-threaded helical guide and advancement structure thereon. The bone screw 4 has an elongate central axis A that extends centrally through the shank 6 and between arms of the integral receiver 10. As will be described in greater detail below, the closure 18 mates with the receiver 10 and presses downwardly against a longitudinal connecting member, such as a rod 21 that in turn presses on the insert 14 so as to capture the rod 21 within the receiver 10 and fix both the rod 21 and the insert 14 in a desired fixed angular position relative to a vertebra (not shown). The longitudinal connecting member that is illustrated as the rod 21 is hard, stiff, non-elastic and cylindrical, having an outer cylindrical surface 22. The illustrated rod 21 is often shown in the drawings in a shortened form convenient for the drawing illustrations. However, an actual rod 21 for use with the assembly 1 would be longer and would, for example, be pre-sized or cut to a length desired to span between two and up to a plurality of bone screws 4 or other bone anchors. The bone screw 4 is initially assembled with the insert 14, typically at a factory setting, prior to implantation of the shank body 6 into a vertebra, as will be described in greater detail below. The bone screw receiver 10 and the insert 14 cooperate in such a manner that the bone screw 4 can be secured at any of a plurality of angles along a single plane, that in the illustrated embodiment is a sagittal plane of a human spine, to enable a desired limited articulated engagement of the bone screw 4 with respect to the rod 21 until both are locked or fixed relative to each other near the end of an implantation procedure.

With particular reference to FIGS. 1-6, the bone screw 4 that includes the shank body 6 further includes more than one helically wound bone implantable thread portion extending from near a neck 26 located adjacent to the receiver 10, to a tip 28 of the body 6 and extending radially outwardly therefrom. The illustrated embodiment shows a combination shank having a two start or dual-form lower portion 24 and a three start or triple-form upper portion 25. In a transition area, generally T, the thread forms 24 and 25 connect and morph together. During manufacture of the shank 6 care is taken to ensure that along the transition length T where the thread form 24 gradually changes or morphs into the thread form 25, the minor diameter of the shank 6 remains substantially constant. Although crest portions may be reduced or removed in places along the transition length T where the thread forms 24 and 25 intersect, a major diameter of the shank at the transition length T, which can be defined as a diameter of a virtual cylinder formed by the thread form crests, is never greater than a major diameter of the thread form 24 or a major diameter of the thread form 25. The transition from a dual lead or start form 24 to a triple lead or start form 25 results in the shank 6 that has a thread form for gripping cancellous bone with a first pitch and another thread form for gripping cortical bone with a second pitch wherein the first pitch is greater than the second pitch, but such a difference in pitch is small in degree and thus provides for a relatively smooth transition between thread forms during insertion of the screw into bone. The smaller second pitch allows for an increased surface area without slowing down an advancement rate of the screw into bone, resulting in a desirable near constant advancement speed without push or pull. During manufacture of the screw body 6, rather than interweaving or interleaving thread forms as is known in the prior art, two distinct thread patterns are machined and as shown in FIGS. 1 and 2, the small transition area or length T is provided wherein the thread form 24 relatively smoothly and gradually changes into the thread form 25. Thus, it is not necessary to have integral multiples of shank threads (e.g., lower two start form transition to an upper four start form) required by an inter-weaving or -leafing process and the associated less desirable greater difference in pitch between lower and upper sections of the shank body. For example, it is foreseen that another desirable thread form transition is a three start helically wound lower thread form section for gripping cancellous bone that transitions into a five start thread form for gripping cortical bone. However, other shank thread types may be used in bone screw embodiments of the invention, including, but not limited to a single or dual start form along an entire surface of the shank as well as other multiple start combinations.

With further reference to FIGS. 1 and 2, during use, the body 6 utilizing the threads 24 and 25 for gripping and advancement is implanted into a vertebra (not shown) leading with the tip 28 and driven down into the vertebra with an installation or driving tool (such as those shown in FIGS. 22-33, for example) so as to be implanted in the vertebra to a location near the neck 26. To provide a biologically active interface with the bone, the threaded shank body 6 may be coated, perforated, made porous or otherwise treated. The treatment may include, but is not limited to a plasma spray coating or other type of coating of a metal or, for example, a calcium phosphate; or a roughening, perforation or indentation in the shank surface, such as by sputtering, sand blasting or acid etching, that allows for bony ingrowth or ongrowth. Certain metal coatings act as a scaffold for bone ingrowth. Bio-ceramic calcium phosphate coatings include, but are not limited to: alpha-tri-calcium phosphate and beta-tri-calcium phosphate ($Ca_3(PO_4)_2$), tetra-calcium phosphate ($Ca_4P_2O_9$), amorphous calcium phosphate and hydroxyapatite ($Ca_{10}(PO_4)_6(OH)_2$). Coating with hydroxyapatite, for example, is desirable as hydroxyapatite is chemically similar to bone with respect to mineral content and has been identified as being bioactive and thus not only supportive of bone ingrowth, but actively taking part in bone bonding.

The shank neck 26 extends axially and upwardly from the shank body 6. The neck 26 may be of the same or have a slightly reduced radius as compared to a top of the threaded portion 25. Further extending axially and outwardly from the neck 26 is the receiver 10. The integral bone screw 4 shown in the drawings is cannulated, having a small central bore 35 extending an entire length of the shank 6 along the axis A. The bore 35 is defined by an inner cylindrical wall of the shank 4 and has a circular opening at the shank tip 28 and an upper opening defined by a frusto-conical surface 37, the surface 37 terminating at a curved receiver seating surface 40 that partially defines a shallow insert receiving cavity, generally 42, the cavity 42 communicating with the cannulation bore 35. The bore 35 provides a passage through the shank 6 interior for a length of wire (not shown) inserted into the vertebra (not shown) prior to the insertion of the bone screw 4, the wire providing a guide for insertion of the shank body 6 into the vertebra.

Figure 4:
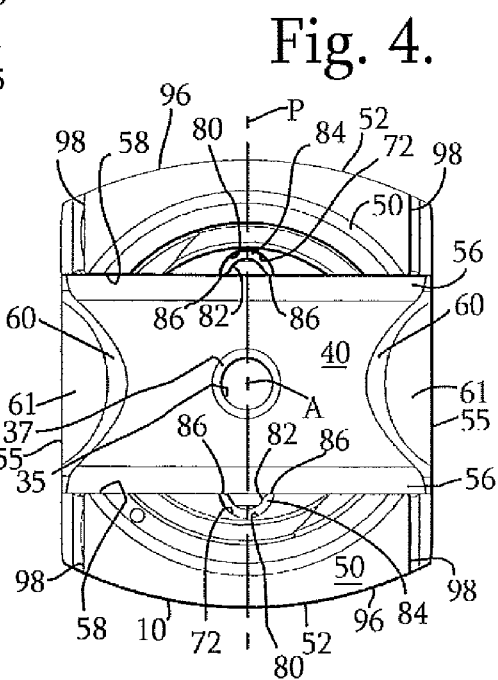
FIG. 4 is a reduced top plan view of the bone screw of FIG. 2.
Figure 5:
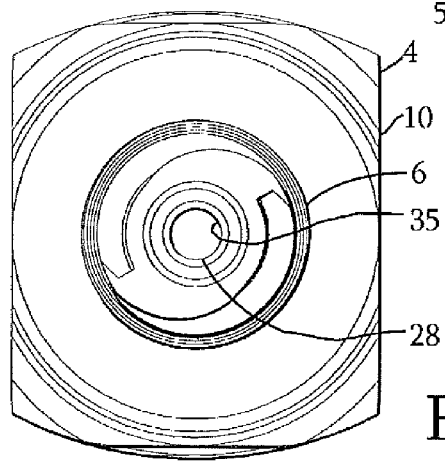
FIG. 5 is a reduced bottom plan view of the bone screw of FIG. 2.
Figure 6:
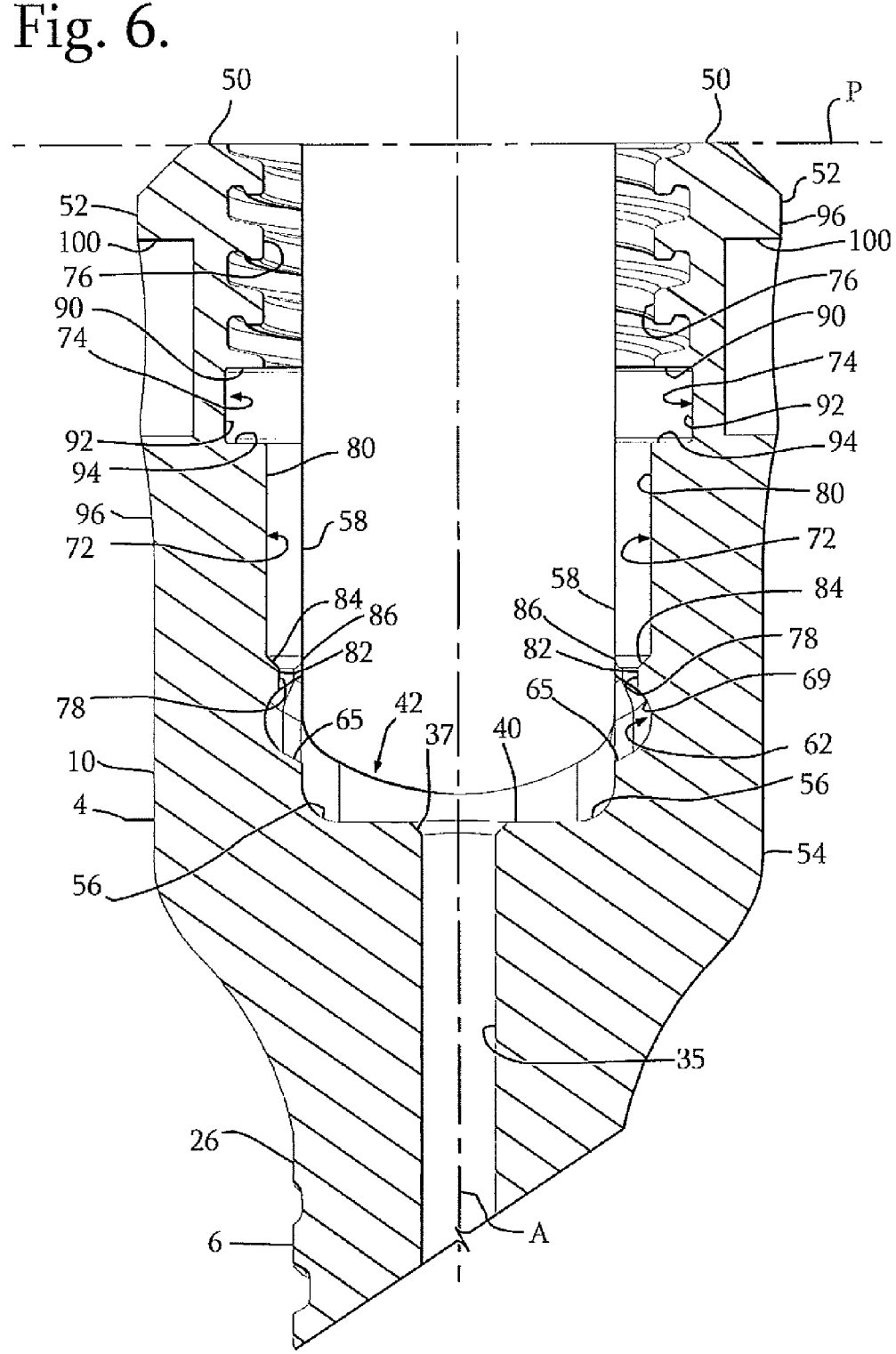
FIG. 6 is an enlarged front elevational view of the bone screw of FIG. 2 with portions broken away to show the detail thereof.
Figure 10:
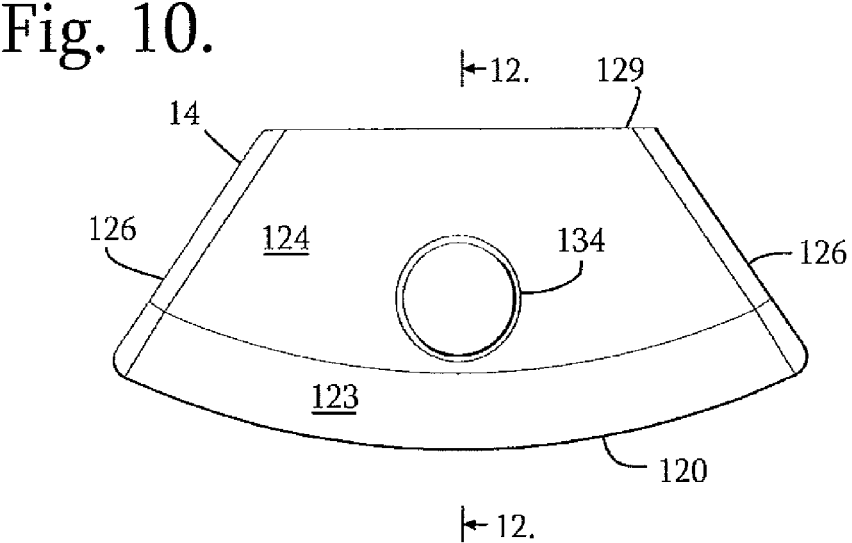
FIG. 10 is an enlarged side elevational view of the insert of FIG. 7.
Figure 11:
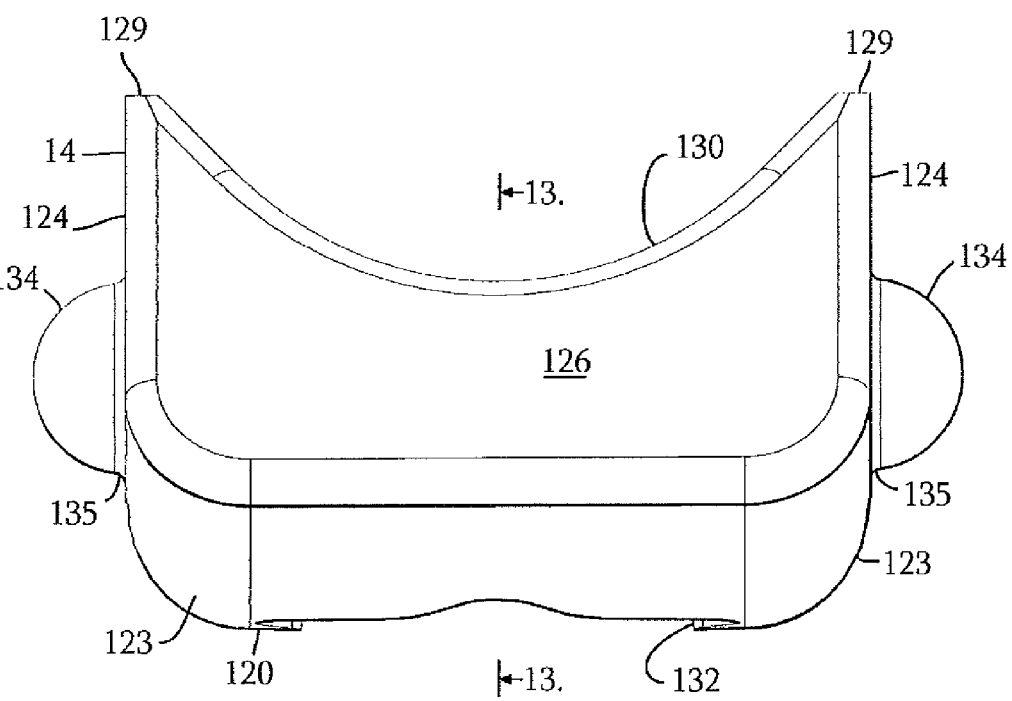
FIG. 11 is an enlarged front elevational view of the insert of FIG. 7.
Figure 12:
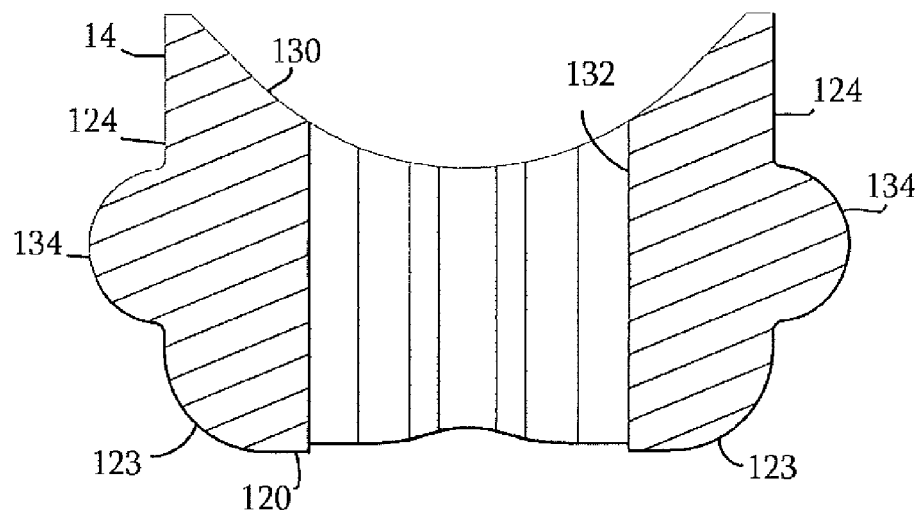
FIG. 12 is an enlarged cross-sectional view taken along the line 12-12 of FIG. 10.
Figure 13:
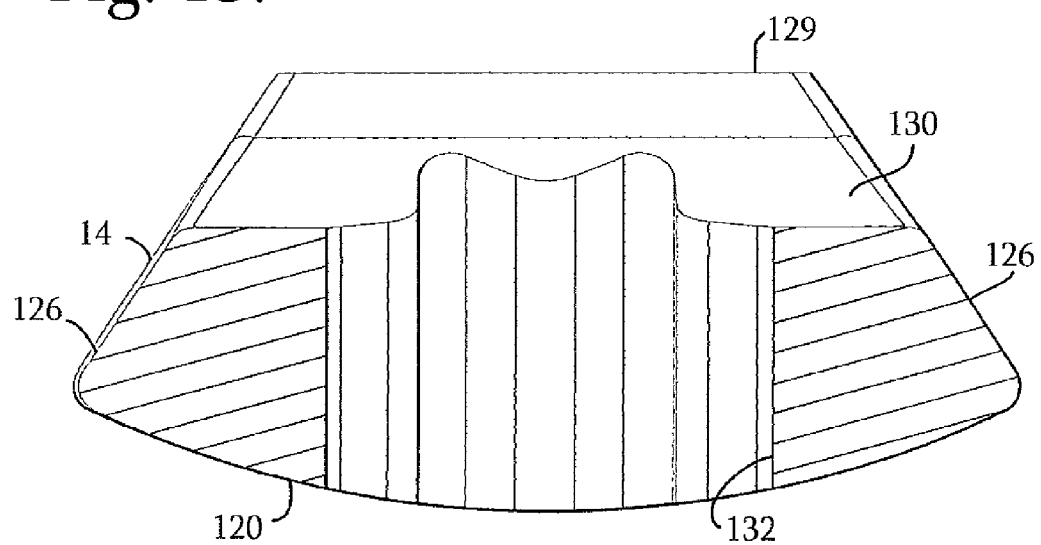
FIG. 13 is an enlarged cross-sectional view taken along the line 13-13 of FIG. 11.
Figure 18:
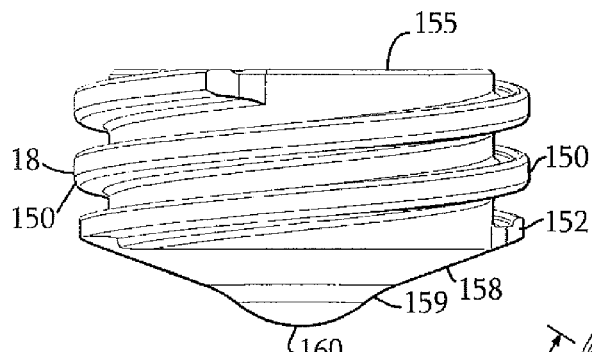
FIG. 18 is an enlarged front elevational view of the closure structure of FIG. 1.
Figure 19:
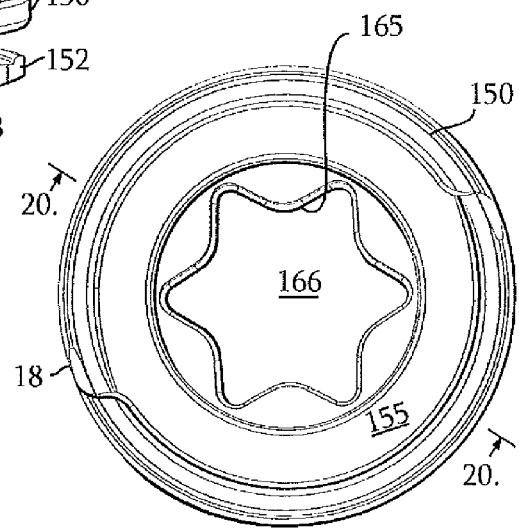
FIG. 19 is a top plan view of the closure structure of FIG. 18.
Figure 20:
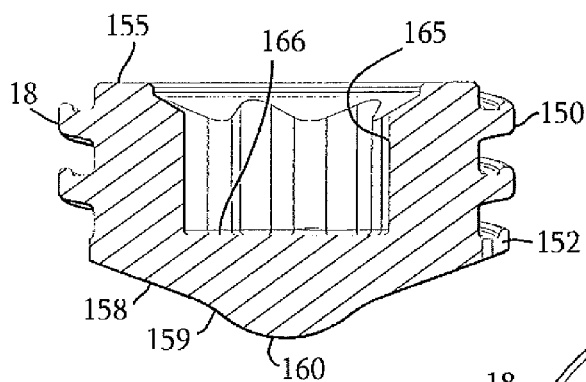
FIG. 20 is a cross-sectional view taken along the line 20-20 of FIG. 19.

With further reference to the bone screw receiver portion 10 shown in FIGS. 2-6, the seating or bottom surface 40 is generally located in a base or bottom portion 54 of the receiver 10, the surface 40 functioning as a cradle for the insert 14 to slide upon about a pivot axis that is located outside of and generally above the insert 14. The base 54 is substantially cylindrical and further includes opposed planar surfaces 55 that are generally located beneath the surface 40 and between the arms 52. In the illustrated embodiment, a pivot axis P for the insert 14 is located at or near substantially planar top surfaces 50 of the opposed receiver arms 52. However, it is foreseen that in other embodiments of the invention a pivot axis for the insert 14 may be positioned at other locations either above or below the receiver top surfaces. As shown in FIGS. 3, 4 and 6, for example, the pivot axis P runs centrally from one receiver arm 52 to the opposed arm 52 and intersects with and is perpendicular to the bone screw central axis of rotation A. The seating surface 40 that cooperates with the insert 14 is arcuate, forming a partial cylinder that is defined by a radius that extends from the pivot axis P to the surface 40, the surface 40 substantially spanning a space between the opposed receiver arms 52. Opposed curved side transition surfaces 56 are located on either side of the surface 40 and extend outwardly from the surface 40 to a respective arm 52 inner substantially planar surface 58 that is parallel to the axis A. As best shown in FIG. 6, each transition surface 56 curves from an orientation being substantially perpendicular to the axis A to an orientation almost parallel with the axis A. Each surface 56 is also arcuate, being defined by radii extending from the pivot axis P. Located at a front and rear of the seating surface 40 and between the arms 52 is an outwardly extending narrow surface or strip 60 and an outwardly and downwardly sloping surface 61. The two opposed strips 60 and adjacent downwardly sloping surfaces 61 are generally positioned transverse to and located beneath a run of the rod 21 and are contoured to receive the rod 21, forming a seat for the rod 21 when the insert 14 (and thus the rod) is in certain angular or pivoted positions with respect to the receiver 10 as will be described in greater detail below and shown, for example, in FIGS. 35 and 36. The outer sloping surfaces 61 terminate at the base planar surfaces 55 that run substantially parallel to the axis A.

Returning to FIGS. 2-4 and 6 and the receiver 10 opposed planar surfaces 58 that partially define the arms 52, the surfaces 58 directly face one another and are disposed parallel to one another, the opposed surfaces 58 being equally spaced from and running parallel to the central axis A. Each surface 58 generally runs from the respective arm top surface 50 to the curved transition surface 56. Each of the surfaces 58 further includes a variety of cut-outs and/or formations formed therein. A pair of opposed arcuate apertures or grooves, generally 62 are centrally formed in lower portions of the surfaces 58 and are each evenly spaced from the seating surface 40. The curvate apertures 62 form a pair of pivot tracks that capture the insert 14 projections, and, in some embodiments, that guide or aid in guiding of the slidable movement of the insert with respect to the bone screw 4. Specifically, with respect to FIG. 3, each aperture 62 is defined by an upper curved surface portion 64 and a lower curved surface portion 65 and terminates at end curved surface portions 67 and 68. A radiused surface portion 69 that may be made up of surfaces of several different radii is located between the top and bottom surface portions 64 and 65 and between the end surface portions 67 and 68. The resulting formation is generally arcuate and is thus defined by radii that originate from the same pivot axis P as the radius of the receiver bottom seating surface 40. It is noted that the pivot aperture 62 may be formed utilizing more or fewer surfaces of different curvatures, the resulting surfaces need only provide a curvate track that closely receives outwardly extending portions of the insert 14 as will be described in greater detail below.

Also formed in each arm inner planar receiver arm surface 58 is a central guide channel or groove, generally 72, that communicates with one of the arcuate apertures 62 and also communicates with a run-out space or area, generally 74, also formed in the planar surface 58 and located below a guide and advancement structure 76, also formed in the planar surface 58, the guide and advancement structure 76 extending to the top surface 50. Each groove 72 runs parallel to the axis A and, similar to the aperture 62, is sized and shaped to closely, slidingly receive a projected portion of the insert 14 as will be described in greater detail below. Near the top surface portion 64 defining the arcuate pivot aperture 62 where the aperture 62 communicates with the groove 72 a projected portion or nub 78 extends generally inwardly from a cylindrical surface 80 defining the groove and toward the axis A. The illustrated nub 78 is partially or somewhat cylindrical and forms a partial constriction band within the groove 72, having an inwardly facing substantially cylindrical surface 82 and a top partially annular surface 84 that slopes upwardly from the surface 82 toward the groove cylindrical surface 80. On each side of the concave cylindrical surface 82 there is a curved, slightly convex surface 86 that spans from the cylindrical surface to the arm planar surface 58. A bottom of the nub 78 is defined by one of the curvate surfaces 69 that partially defines the arcuate pivot aperture 62. The nub or projection 78 forms a constriction, bottle-neck or stop so that a portion of the insert 14 must be forced beyond the projection 78 during assembly and then, after being pressed or forced beyond the nub 78, the insert 14 portion is prohibited by the nub from escaping from the arcuate aperture 62 and thus the insert 14 is prohibited from escaping out of the receiver 10. It is foreseen that in other embodiments the constriction nub 78 may have a different geometry.

As indicated above, each of the arms 52 has the interior planar surface 58 into which is formed a cylindrical form that includes the partial helically wound guide and advancement structure or flange 76 that extends radially inwardly toward the axis A. Each guide and advancement structure 76 begins near the bone screw top surface 50 and terminates at the run-out 74. As best illustrated in FIG. 6, the run-out 74 includes an upper substantially annular surface 90 located adjacent an inner discontinuous cylindrical surface 92 and is also partially defined by a discontinuous annular surface 94 located adjacent the planar surface 58. The annular surface 94 is also adjacent to and cut into by the partial cylindrical surface 80 that defines most of the guide channel 72. Both the discontinuous annular surfaces 90 and 94 are disposed substantially perpendicular to the axis A, while the surface 92 runs parallel to the axis A.

In the illustrated embodiment, the guide and advancement structures 76 are each in the form of a partial helically wound interlocking flangeform configured to mate under rotation with the dual start closure structure 18. Thus, unlike single start advancement structures, the helical forms 76 on the opposing inner arm surfaces that are configured to mate with the dual start closure top 18 are reverse or flipped images of one another, the structures 76 on each arm 52 being aligned with respect to the receiver axis A, so that each closure structure start is simultaneously engaged and captured at each arm 52 at the same time. Although the illustrated guide and advancement structures 76 are shown as interlocking flange forms, it is foreseen that the guide and advancement structures 76 could alternatively be of a different geometry, such as a square-shaped thread, a buttress thread, a reverse angle thread or other thread-like or non-thread-like helically wound discontinuous advancement structure for operably guiding under rotation and advancing a closure structure downward between the receiver arms 52, as well as eventual torquing when the closure structure 18 abuts against the rod 21. Further information on interlocking flange forms is provided, for example, in Applicant's U.S. Pat. No. 6,726,689 that is incorporated by reference herein.

With respect to outer side surfaces 96 of the arms 52 and also substantially planar front and rear surfaces 98 of each of the arms 52, located substantially centrally in each arm outer surface 96 is a shallow recess or aperture 100. The recess 100 does not extend all the way through the arm 52. The recess 100 is sized and shaped for receiving a tool (not shown) used to hold and/or manipulate the bone screw 4. Similarly, each arm surface 98 includes a shallow tool receiving aperture 102. Some or all of the apertures and recesses described herein, including, but not limited to the recesses 100 and 102 may be used for holding the bone screw 4 during assembly with the insert 14; during the implantation of the shank body 6 into a vertebra; during assembly of the bone anchor assembly 1 with the rod 21 and the closure structure 18; and during angular and rotational adjustment of the bone screw 4 with respect to the insert 14 and rod 21 as will be described in greater detail below. It is foreseen that tool receiving recesses, grooves or apertures may be configured in a variety of shapes and sizes and be disposed at other locations on the receiver arm 96 outer and/or inner surfaces as well as surfaces defining the base 54.

With particular reference to FIGS. 1 and 7-13, the pivot insert 14 is illustrated that is sized and shaped to be received by and down-loaded into the receiver 10 at an upper opening defined by the arm top 50 and inner 58 surfaces. In operation, the insert advantageously frictionally engages the rod 21 while being in slidable, pivotable relationship with respect to the entire bone screw 4 that includes the shank 6 and the integral receiver 10. The insert 14 allows for sliding and pivoting movement and adjustment of the rod 22 with respect to the bone screw shank 6, advantageous in certain situations, such as for the treatment of scoliosis wherein the vertebrae are manipulated by rotation, and the bone screw assembly 1 allows for pivoting adjustment of the shank 6 with respect to the rod 21 in the sagittal plane. Then, the shank 6 may be locked in a desired angular position with respect to the rod 21 by the closure 18 pressing down upon the rod 21 that in turn presses the insert 14 into fixed frictional engagement with the seating surface 40 of the bone screw receiver 10.

The insert 14 is of discrete or unitary, substantially solid construction and includes a curved bottom surface 120 adjacent to opposed curved side transition surfaces 123 that are each in turn adjacent to opposed substantially planar side surfaces 124 that are disposed substantially perpendicular to the bottom surface 120. Each of the side surfaces 124 terminate at a substantially planar narrow top rim surface 129. The insert 14 further includes front and rear sloping surfaces 126 into which is cut a curved cradle or saddle surface 130 sized and shaped for closely receiving the rod 21. The cradle surface 130 also extends between the top surfaces 129. A star-shaped drive feature 132 extends completely through the insert from the top saddle or cradle surface 130 to the bottom curved surface 120. Disposed centrally along each of the surfaces 124 is an outwardly extending projection 134 that in the illustrated embodiment is in the form of a rounded knob or partial sphere, the illustrated knob 134 includes another radiused transition surface or flange 135 that is adjacent both to the substantially spherical surface 134 and to the respective planar side surface 124. It is noted that in other embodiments of the invention, the projections 134 may include more or fewer radiused surfaces and may also include one or more surfaces having other geometry. The projection knobs 134 are opposed from one another, each being spaced from the bottom surface 120 and also from the top rims 129.

In operation, when the insert 14 is located within the receiver cavity 42, the bottom surface 120 can be defined by a pivot radius that is the same or substantially similar to the radius previously described herein with respect to the receiver bottom seating surface 40, the receiver axis A and the pivot axis P. This is also evident from FIGS. 34-38, for example, and as will be described in greater detail below. The knobs 134 are sized and shaped and positioned with respect to the bottom surface 120 so that in operation, the knobs 134 extend into the receiver pivot apertures 62 and slide freely therewithin as the insert bottom surface 120 slides along the receiver bottom surface 40. Furthermore, the insert transition surfaces 123 are sized and shaped such that the surfaces 123 are received by and slide freely with respect to the receiver surfaces 56. In operation, the insert substantially planar side surfaces 124 are closely received between the receiver arm opposed surfaces 58, keeping the insert 14 in a desired alignment with the receiver and thus keeping a rod 21 cradled by the insert surface 130 in a desired alignment with not only the receiver, but the entire bone screw 4, including the shank 6 that is integral to the receiver 10, thus always keeping the rod 21 and the shank 6 in a pivotable relationship prior to locking that is in one plane only, along the run of the rod, which is typically and desirably the sagittal plane. Thus, the bone screw assembly 1 has a shank 6 that angulates only in the sagittal plane that provides for improved strength over polyaxial screws and two-piece uni-planar screws, as the bone screw shank 6 is integral with the receiver 10.

Bone screws 4 and inserts 14 of embodiments of the invention may be made from a variety of materials including metal and metal alloys, including but not limited to stainless steel, titanium, titanium alloys and cobalt chrome; or other suitable materials, including plastic polymers. It may be desirable, for example, to form the insert 14 from a harder material, such as cobalt chrome and the integral, one-piece receiver/shank from a less hard material, such as a titanium alloy. In such an arrangement, the insert 14 knobs 134 being pressed through the constriction nubs 78 during assembly, as will be described in greater detail below, will be harder than the nubs 78.

As indicated above, the insert saddle or cradle 130 is in the form of a curved seat sized and shaped to closely, snugly engage the rod 21 or other longitudinal connecting member. It is foreseen that an alternative embodiment may be configured to include planar holding surfaces that closely hold a square or rectangular bar as well as hold a cylindrical rod-shaped, cord, or sleeved tensioned cord longitudinal connecting member.

The drive feature 132 is also a through bore and is sized and shaped to receive a driving tool, such as the tools shown in FIGS. 22-27, for example. As will be described in greater detail below, such tools engage the drive feature 132 when the shank body 6 is driven into bone. Also, the drive feature 132 may receive a guide pin or wire during implantation as will be described below. The illustrated internal drive feature 132 is an aperture formed in the curved surface 130 and has a star shape designed to receive a bit of an Allen wrench type tool into the aperture for rotating and driving the bone screw shank 6 into a vertebra (not shown). It is foreseen that such an internal tool engagement structure may take a variety of tool-engaging forms and may include one or more apertures of various shapes, such as a pair of spaced apart apertures or a hex shape or a multi-lobular aperture, for example. During driving of the bone screw shank 6 into bone, the drive aperture 132 and thus the drive tool is positioned along the axis A of the bone screw 4. In some embodiments, the drive 132 may have additional beveled or stepped surfaces for further enhancing gripping with the driving tool.

With reference to FIGS. 1 and 34-42, the illustrated elongate rod or longitudinal connecting member 21 (of which only a portion has been shown) can be any of a variety of implants utilized in reconstructive spinal surgery, but is typically a cylindrical, elongate structure having the outer substantially smooth, cylindrical surface 22 of uniform diameter. Longitudinal connecting members for use with the assembly 1 may take a variety of shapes, including but not limited to rods or bars of oval, rectangular or other curved or polygonal cross-section. The shape of the insert 14 may be modified so as to closely hold the particular longitudinal connecting member used in the assembly 1. Longitudinal connecting members in the form of rods, bars or other geometric shapes may be made of materials including, but not limited to metal and metal alloys including but not limited to stainless steel, titanium, titanium alloys and cobalt chrome; or other suitable materials, including plastic polymers such as polyetheretherketone (PEEK), ultra-high-molecular weight-polyethylene (UHMWP), polyurethanes and composites, including composites containing carbon fiber, natural or synthetic elastomers such as polyisoprene (natural rubber), and synthetic polymers, copolymers, and thermoplastic elastomers, for example, polyurethane elastomers such as polycarbonate-urethane elastomers.

Some embodiments of the assembly 1 may also be used with longitudinal connecting members that may include a tensioned cord and other components surrounding the cord, including, but not limited to, rigid outer sleeves, spacers, elastic bumpers, end fixing structures and other fixing structures for attaching the cord to a more rigid connecting member. Tensioned cords may be made from a variety of materials, including polyester or other plastic fibers, strands or threads, such as polyethylene-terephthalate. Furthermore, the longitudinal connector may be a component of a longer overall dynamic stabilization connecting member, with cylindrical or bar-shaped portions sized and shaped for being received by the bone screw assembly and/or other bone anchors having a U-shaped, rectangular- or other-shaped channel, for closely receiving the longitudinal connecting member. The longitudinal connecting member may be integral or otherwise fixed to a bendable or damping component that is sized and shaped to be located between adjacent pairs of bone screws or other anchors. A damping component or bumper may be attached to the longitudinal connecting member at one or both sides of the bone screw assembly 1. A rod or bar (or rod or bar component) of a longitudinal connecting member may be made of a variety of materials ranging from deformable plastics to hard metals, depending upon the desired application.

With reference to FIGS. 1 and 18-21, the closure 18 is illustrated having an outer guide and advancement structure 150 in the form of a double-start helically wound splay control flange form. In operation, the closure 18 has an axis of rotation that is the same as the axis of rotation A of the bone screw 4. As will be described in greater detail below, the closure top 18 mates under rotation with the receiver 10, the structure 18 pressing downwardly against the rod 21 cylindrical surface 22 that in turn presses down on the insert 14 that is then frictionally fixed against the receiver seating surface 40 during final locking of the angle of the shank 6 with respect to the rod 21. The closure top or plug 18 thus ultimately frictionally engages and presses against the rod 21 or other longitudinal connecting member, so as to capture, and fix the rod 21 within the receiver 10 and thus fix the rod 21 relative to the vertebra into which the shank 6 is implanted.

The illustrated closure 18 is a multi-start closure outer splay control structure having a double or dual start helically wound guide and advancement structure in the form of the pair of identical helically wound forms 150, each illustrated as a flange form that operably joins with mating flange form structures 76 disposed on the arms 52 of the receiver 10 to result in an interlocking guide and advancement structure or arrangement. Although a particular flange form structure and relationship is shown herein, it is noted that flange forms may be of a variety of geometries, including, for example, those described in Applicant's U.S. patent application Ser. No. 11/101,859 filed Apr. 8, 2005 (US Pub. No. 2005/0182410 published Aug. 18, 2005), which is incorporated by reference herein.

Figure 21:
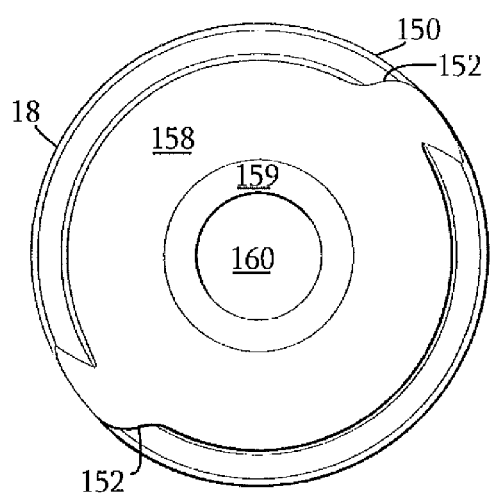
FIG. 21 is a bottom plan view of the closure structure of FIG. 18.

Each form 150 includes a start surface or structure 152 and thus, as shown in FIG. 21, the closure 18 includes two starts 152. The cooperating flange forms 150 and 76 have respective splay regulating contours to control splay of the receiver arms 52 when the inner member 18 is strongly torqued therein. In the illustrated embodiment, the closure 18 is a discrete or singular integral plug. In other embodiments, the closure may include an outer feature and a rotatingly mated inner plug. Embodiments with upper break-off heads or extensions that separate from the closure when installation torque exceeds a selected level are also foreseen. Such closures are disclosed, in Applicant's U.S. Pat. No. 7,967,850 (see, e.g., FIGS. 22-25 and accompanying disclosure).

The illustrated fastener structure 18 further includes a substantially planar top surface 155 and a generally curved or domed shaped bottom surface. In particular, the illustrated embodiment includes a lower substantially frusto-conical surface 158 located adjacent the starts 152 of the guide and advancement structures 150, the surface 158 extending downwardly and inwardly and then merging into another curved surface 159 that also extends generally downwardly and inwardly. The interim surface 159 is also adjacent to a substantially domed bottom surface 160. In the illustrated embodiment, the bottom surface 160 is convex and radiused or partially spherical while the surface 159 that spans between the surfaces 158 and 160 is curved and has a slight concavity. It is foreseen that more or fewer curved surfaces may be included for gripping the rod 21 during initial adjustment of an angle of the rod 21 with respect to the bone screw 4 and then final frictional engagement of the closure 18 against the rod 21 after a desired manipulation of the spine (e.g., distraction, compression and rotation of the spinal segments connected to the rod 21 by two or more bone screw assemblies 1 or other bone anchors) has been performed and a resulting adjusted sagittal plane angular position of the bone screw shank 6 with respect to the rod 21 occurs.

As indicated previously, the closure or fastener structure 18 is substantially cylindrical and the two flange forms 150 project substantially radially outwardly. The closure structure 18 helically wound flange form start structures 152 are located on opposite sides of the closure structure and are both located adjacent the lower surface 158. When the closure structure 18 is rotated into the receiver 10 between receiver arms 52, each having the flange form 76 guide and advancement structure, the start 152 engages mating guide and advancement structure 76 on one arm 52 and the opposite start 150 simultaneously engages guide and advancement structure flange form 76 on the opposing arm 52, both forms 152 being simultaneously captured by the mating forms 76 on the opposed arms 52. Each time the illustrated duel- or double-start closure plug 18 is rotated one complete turn or pass (three hundred sixty degrees) between the implant arm extensions or arms, the closure 18 advances axially toward and then into the receiver 10 a width of two helical flange forms. The closure 18 is sized for at least one complete rotation (three hundred sixty degree) of the closure 18 with respect to the receiver 10 open arms 52 to substantially receive the closure 18 between the implant arms. Multi-start closures may have two or more coarse or fine helical forms, resulting in fewer or greater forms per axial distance spiraling about the closure plug body and thus resulting in plugs that rotate less or more than one complete rotation to be fully received between the implant arms. Preferably, helically wound forms are sized so as to spiral around a cylindrical plug body thereof to an extent that the closure rotates at least ninety-one degrees to fully or substantially receive the closure 18 between the arms of the bone screw receiver or other open implant. Particularly preferred guide and advancement structures are sized for at least one complete turn or pass (three-hundred sixty degree) of the closure between the receiver 10 arms 52 and as many as two to three rotations to be fully received between implant arms. It is foreseen that bone screw receivers 10 and closures 18 may also be designed as single-start flange forms or other non-thread or threadlike forms.

Formed in the substantially planar top surface 155 is a drive feature 165 having a substantially planar base 166. In some embodiments of the invention a further centrally located cannulation bore may be included running from the drive feature 165 to the domed bottom 160 for providing a passage through the closure 18 interior for a length of wire (not shown) inserted therein to provide a guide for insertion of the closure top into the receiver arms 52. The illustrated drive feature 165 has a star-like shape sized and shaped to receive a closure driving tool bit having a cooperating star-shape or form for engaging surfaces of the drive feature 165 and the drive feature base 166 to rotate the closure 18 between the receiver arms 52. It is noted that other drive configurations may be used, including, but not limited to the internal drive features discussed above with respect to the insert 14 drive feature 132.

As indicated above, tools for driving the bone screw 4 and connected insert 14 into bone are shown in FIGS. 22-33. With particular reference to FIGS. 22-27, a driving tool 170 and outer sleeve 172 combination is illustrated. The inner driving tool 170 further includes an elongate and substantially tubular and cylindrical body portion 176 with a cylindrical surface 177 and having a top surface 178 located near a partially faceted handle portion 179 at an upper end thereof and a tool bit 180 having a bottom surface 181 at a lower end thereof. The tool 170 includes an inner cannula or through bore 183. The handle portion 179 has a diameter slightly greater than a diameter of the cylindrical surface 177 of the body portion 176, but it is designed to be small enough to be closely slidingly received by the sleeve 172. Also, located between the bit 180 and the body 176 is an intermediate cylindrical portion 185 having a diameter greater than the diameter of the surface 177 as well as greater than the diameter of the handle portion 179 and further including opposed planar surfaces 186 sized and shaped for being closely received between the planar inner arm surfaces 58 of the receiver arms 52. A substantially planar lower surface 188 extends from the portion 185 cylindrical surface to the tool bit 180, the surface 188 being substantially parallel with the bit bottom surface 181. The illustrated tool bit 180 is integral or otherwise fixed to the portion 185 and is sized and shaped for being closely received by the star-shaped drive 132 of the insert 14. Because the insert drive 132 is a through bore, the bit bottom surface 181 does not seat on a portion of the drive, rather, the planar somewhat annular surface 188 seats on the upper rim surfaces 129 of the insert 14 during driving of the tool bit 181 within the drive 132. Also, the intermediate portion 185 has a graduated upper surface 190 that includes an annular shelf or ledge 191 upon which the outer sleeve 172 can seat as will be described in greater detail below.

The outer sleeve 172 that fits over the inner driver 170 and attaches to the receiver arms 52 during driving of the bone screw 4 into bone is also tubular and includes a handle 194 near a top 195 thereof and a guide and advancement structure 197 near an annular planar bottom surface 198 thereof. A through bore 199 is sized and shaped for receiving the driving tool 170 with the exception of the larger diameter portion 185 that is adjacent the tool bit 180. The guide and advancement structure 197 is illustrated as a flange form similar to the flange form structure 150 of the closure top 18 for mating engagement with the receiver flange form structures 76. However, it is noted that other guide and advancement structures may be used for the tool 172, such as a square thread form sized and shaped to have a helical form that fits within a helical space defined by the flange form structures 76 of the receiver arms 52.

With reference to FIGS. 28-30, a driving tool 170' is shown that is substantially similar to the tool 170 and may or may not be used with the outer drive sleeve 172. Thus, the tool 170' includes a body 176' having an outer cylindrical surface 177', a top surface 178', a faceted handle 179', a star-shaped tool bit 180', a bottom surface 181', an inner through bore 183', an intermediate portion 185' with opposed planar surfaces 186', a planar lower surface 188' and an upper annular shelf 191' of the portion 185' that are the same or substantially similar in form and function to the respective body 176 with cylindrical surface 177, top surface 178, faceted handle 179, star-shaped tool bit 180, bottom surface 181, inner through bore 183, intermediate portion 185 with opposed planar surfaces 186, planar lower surface 188 and annular shelf 191 previously described herein with respect to the driving tool 170. Furthermore, the tool 170' includes a pair of opposed spring-loaded detent nodes 192' extending outwardly from the intermediate portion 185' and located near the shelf 191'. As best shown in FIG. 30, during assembly of the tool 170' into the receiver 10, the spring-loaded nodes 192' are pressed inwardly and then resiliently return to an outwardly extending position shown in FIG. 30 located beneath an upper flange form portion of the flange forms 76, thus pressing the nodes 192' into frictional engagement with portions of the flange forms 76. In some embodiments, this provides sufficient strength and additional frictional engagement and support between the driver 170' and the bone screw 4 such that a user may decide to use the tool 170' alone without the outer sleeve 172.

Figure 31:
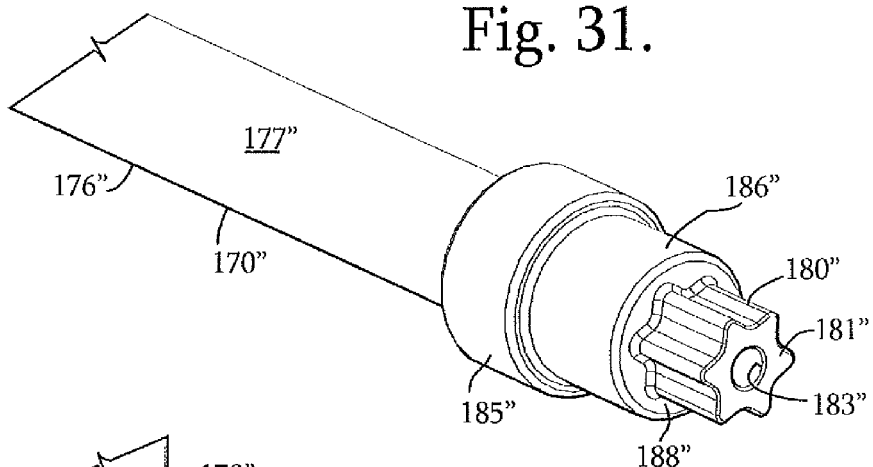
FIG. 31 is an enlarged and partial perspective view of another alternative driving/manipulation tool for use with the bone screw of FIG. 1.
Figure 32:
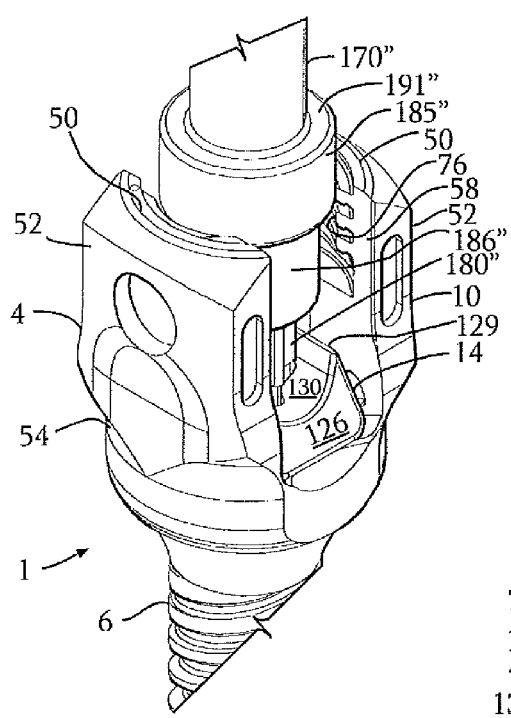
FIG. 32 is another partial perspective view of the tool of FIG. 31 shown with the assembled bone screw receiver and insert of FIG. 17, also in partial perspective view and shown just prior to insertion of the tool into the insert.
Figure 33:
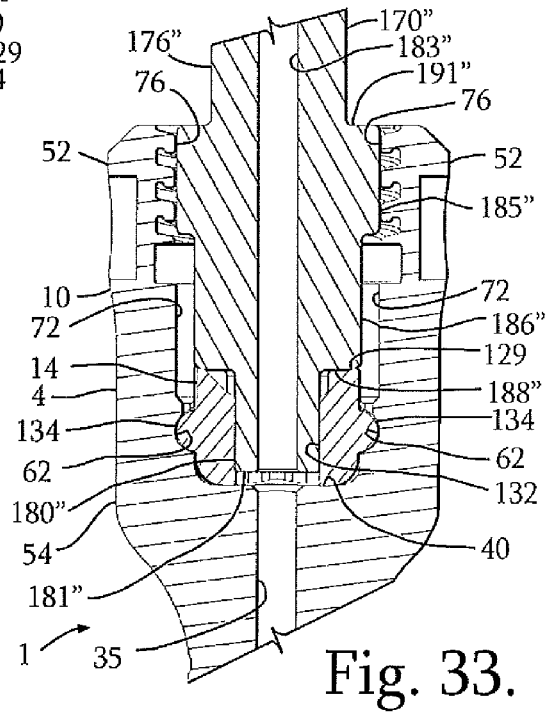
FIG. 33 is an enlarged and partial front elevational view with portions broken away of the tool and bone screw of FIG. 32 and further showing the tool inserted into the insert.

FIGS. 31-33 illustrate an alternative simple driver 170" being used with the bone screw assembly 1. The driver 170" is substantially similar to the drivers 170 and 170' except that the driver 170" does not include a spring-loaded detent feature and the driver 170" further includes a cylindrical portion 186" of reduced diameter in lieu of the opposed planar surfaces 186 of the tool 170. Thus, the driver 170" includes a body 176" having an outer cylindrical surface 177", a top surface 178", a faceted handle (not shown), a star-shaped tool bit 180", a bottom surface 181", an inner through bore 183", an intermediate portion 185", a planar lower surface 188" and an upper annular shelf 191" of the portion 185" that are the same or substantially similar in form and function to the respective body 176 with cylindrical surface 177, top surface 178, faceted handle 179, star-shaped tool bit 180, bottom surface 181, inner through bore 183, intermediate portion 185, planar lower surface 188 and annular shelf 191 previously described herein with respect to the driving tool 170. As noted above, the simple drive 170" does not include opposed planar surfaces useful in aligning the drive bit with the internal drive of the insert as well as providing additional surfaces at the planar insert inner arms for driving the bone screw 4. Rather, the cylindrical portion 186" of reduced diameter is sized to be completely received between the planar surfaces of the receiver arms 52 and thus a particular alignment of the driver and receiver surfaces is not required when using the driver 170".

The receiver 10 with integral shank is assembled with the shank 4 at a factory setting that includes tooling for holding, alignment and manipulation of the component pieces. Pre-assembly of the insert 14 into the receiver 10 is shown in FIGS. 14-17. With particular reference to FIG. 14, the insert 14 is downloaded into the receiver by initially placing the insert bottom surface 120 at an upper opening of the receiver 10 and then between the arm top surfaces 50 with the insert projection knobs 134 each facing an arm inner surface defined at the top of the receiver by the opposed guide and advancement structures 76. Then, the insert 14 is lowered until the projections 134 are each received in an alignment groove 72 as shown in FIG. 14. With reference to FIG. 15, the projections 134 easily slide down the alignment grooves 72 until the projections abut against the nubs 78 projecting inwardly near the intersection of the alignment grooves 72 and the arcuate pivot apertures 62. At this time, and with respect to FIGS. 15 and 16, a substantial downward force is placed on the insert 14 to press the projection knobs 134 of the insert 14 past the top sloping surfaces 84, the side surfaces 86 and the cylindrical surfaces 82 of the nubs 78. During this pushing or pressing step, the nubs 78 as well as the knobs 134 may undergo some deformation and the receiver arms 52 may temporarily splay away from one another. Once the projection knobs 134 are pressed past the cylindrical surfaces 82, the knobs 134 slide freely within the respective arcuate apertures 62 and are captured in the apertures by the nubs 78 (now acting as stops) and the surfaces defining the apertures 62, including the end portions 67 that limit the pivoting and sliding movement of the insert 14 with respect to the receiver 10. With reference to FIGS. 16 and 17, for example, at this time, the insert bottom surface 120 is in sliding engagement with the receiver seating surface 40 and the insert side surfaces 124 and lower curved surfaces 123 are closely received by the respective receiver planar surfaces 58 and lower curved surfaces 56, keeping the insert 14 in a desired alignment with the receiver 10 with the rod receiving cradle 130 aligned with and running centrally between the receiver arms 52. At this time, the insert 14 is slidable with respect to the receiver 10 along the surface 40 and about the pivot axis P, the insert being prohibited from moving upwardly and out of the receiver by the projections 134 being captured in the arcuate pivot track or aperture 62 and the receiver surfaces, particularly the planar surfaces 58 prohibiting any rotation of the insert 14 with respect to the receiver 10 and thus with respect to the shank 6 that is integral with the receiver 10.

With further reference to FIG. 17 and also with reference to FIGS. 22-27, the bone screw assembly 1 made up of the integral shank 6/receiver 10 and the now slidingly captured insert 14 is screwed into a bone, such as a vertebra (not shown), by rotation of the bone screw 4 using a suitable driving tool, such as the driver 170 and outer sleeve 172 to operably drive and rotate the shank body 6 by engagement of the insert 14 at the internal drive 132. The vertebra may be pre-drilled to minimize stressing the bone and have a guide wire (not shown) inserted therein to provide a guide for the placement and angle of the shank 6 with respect to the vertebra. A further tap hole may be made using a tap with the guide wire as a guide. Then, the bone screw assembly 1 is threaded onto the guide wire utilizing the cannulation bore 35 by first threading the wire into the opening at the shank bottom 28 and then out of a top opening defined by the insert 14 drive feature 132 that is axially aligned with the bone screw bore 35 along the axis A. The insert 14 is located centrally on and fully supported by the receiver surface 40 during the driving of the bone screw assembly 1 into the vertebra. The shank 6 is then driven into the vertebra using the wire as a placement guide.

Figures 25, 26, 27:
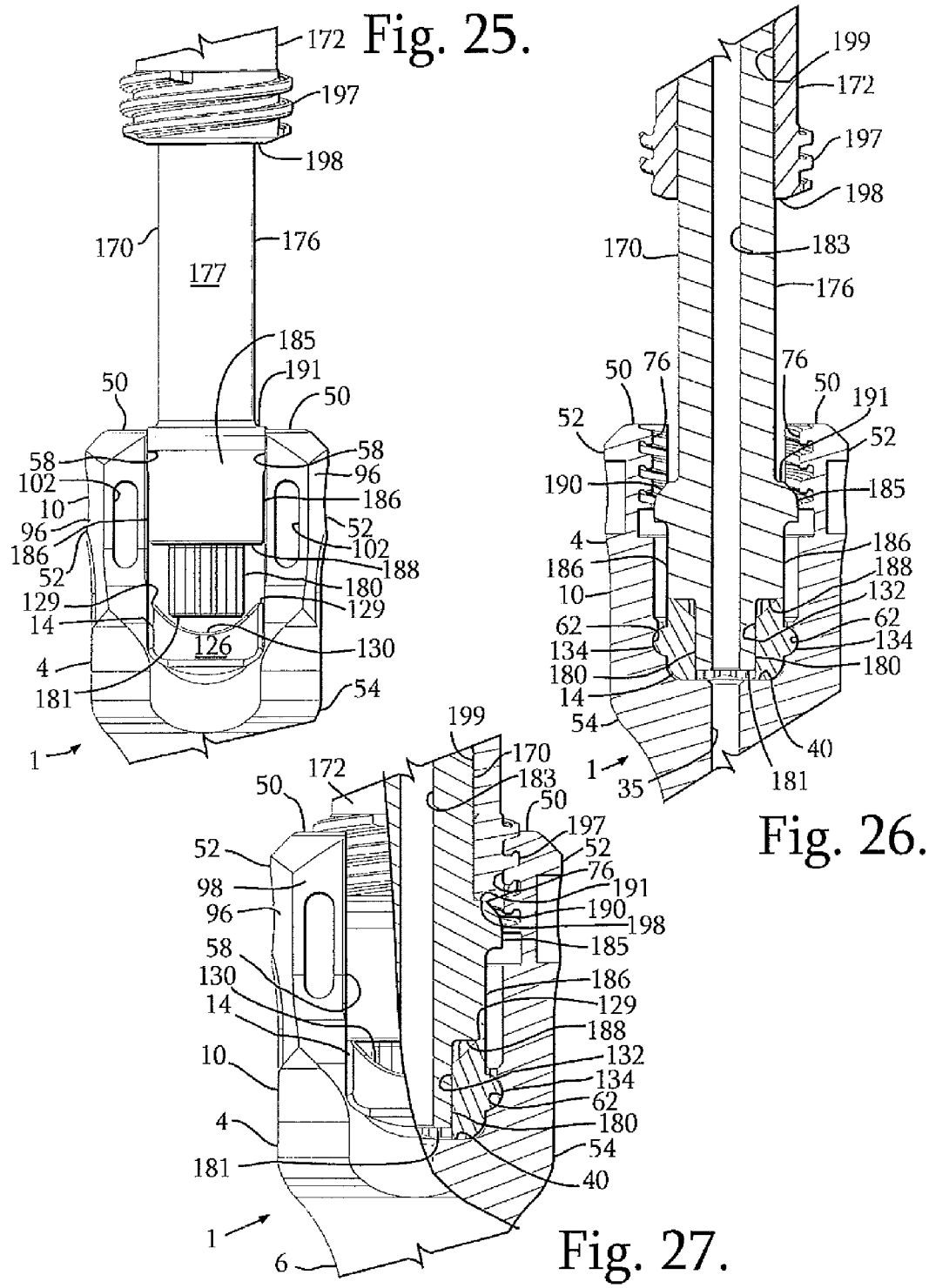
FIG. 25 is a partial front elevational view of the driver and bone screw, similar to FIG. 24, showing the inner driver inserted into the receiver of the bone screw.
FIG. 26 is a partial front elevational view of the driver and bone screw, similar to FIG. 25, but with portions broken away to show the detail thereof showing the inner driver engaged with the insert.
FIG. 27 is an enlarged and partial front elevational view of the driver and bone screw with portions broken away, similar to FIG. 26, and further showing the driver outer sleeve in engagement with the receiver of the bone screw.

With further reference to FIG. 22, the outer sleeve 172 of the driving tool is assembled with the inner driver 170 by placing the sleeve bottom surface 198 over the driver top surface 178 and sliding the tool 170 into the sleeve through bore 199. Thereafter, as illustrated in FIGS. 24 and 25, the resulting combined tool is placed over the bone screw receiver 10 top surfaces 50 with the bit 180 bottom surface 181 leading into the channel formed by the receiver inner arm surfaces 58. The guide wire, if any, may also be received through the drive tool 170 inner through bore 183 by threading the wire into the through bore at the bottom 181 of the tool bit 180 and out the top 178. With specific reference to FIG. 25, the tool 170 must be rotated such that the planar surfaces 186 are received between the inner arm surfaces 58. This step also aligns the star-shape tool bit 180 with the star shape aperture 132 of the insert drive feature. As shown in FIG. 26, the drive tool bit 180 is received in the aperture 132 with the planar surface 188 seating on the insert top surfaces 129. With reference to FIG. 27, thereafter, the outer sleeve 172 is moved downwardly and the guide and advancement structure 197 of the tool 172 is rotatingly mated with the receiver guide and advancement structures 76 located on the arms 52. The tool 172 can be rotated until the bottom surface 198 abuts against the drive tool surface 191 as shown in FIG. 27, placing the outer sleeve 172 into frictional engagement with the inner drive tool 170. The combo-tool 170/172 is now fully frictionally engaged with both the insert drive feature and multiple surfaces of the receiver, including opposed arm planar surfaces 58 and each of the flange form guide and advancement structures 76. At this time, the combo-tool 170/172 may be used to rotate the shank 6 into the vertebra (not shown) over the guide wire. It is foreseen that in other embodiments, the rod 21 (also having a central lumen in some embodiments) and a closure top having a central bore could also be inserted in a percutaneous or minimally invasive surgical manner, utilizing guide wires.

Once the shank 6 is implanted, the combo tool 170/172 may be removed by first rotating the outer sleeve 172 guide and advancement structure 197 out of the receiver guide and advancement structures 76 and the removing the tool bit 180 from the insert 14 and out of the receiver arms 52. At this time, the insert 14 freely pivots with respect to the implanted shank 6.

With reference to FIGS. 28-32, in certain situations the tool 170' may be used to drive the bone screw 4 into bone in lieu of the driver 170 and sleeve 172 described above. In such a situation, the tool 170' is placed over the bone screw receiver 10 top surfaces 50 with the bit 180' bottom surface 181' leading into the channel formed by the receiver inner arm surfaces 58. The guide wire, if any, may also be received through the drive tool 170' inner through bore 183' by threading the wire into the through bore at the bottom 181' of the tool bit 180' and out the top 178'. With specific reference to FIG.

30, the tool 170' must be rotated such that the planar surfaces 186' are received between the inner arm surfaces 58. This step also aligns the star-shape tool bit 180' with the star shape aperture 132 of the insert drive feature. As shown in FIG. 30, the drive tool bit 180' is received in the aperture 132 with the planar surface 188' seating on the insert top surfaces 129. Also, as the tool 170' is lowered into the receiver 10, the spring loaded detent balls 192' that are axially aligned with the tool flat surfaces 186' are pressed inwardly by upper inwardly extending portions of each of the receiver guide and advancement structures 76. After the tool 170' is lowered slightly, each of the detent balls 192' resiliently springs outwardly into a location between guide and advancement structure flange forms as shown in FIG. 30. At this time, the tool planar surface 188' also abuts against the insert 14 upper rim surfaces 129. The tool 170' is now fully frictionally engaged with both the insert drive feature and multiple surfaces of the receiver, include opposed arm planar surfaces 58 and portions of each of the flange form guide and advancement structures 76. At this time, the tool 170' may be used to rotate the shank 6 and thus drive the shank 6 into the vertebra (not shown) over the guide wire. Disassembly of the tool from the assembly 1 is then accomplished in reverse order to the procedure described herein for the assembly.

With reference to FIGS. 31-33, in certain situations the tool 170" may be used to drive the bone screw 4 into bone in lieu of the driver 170 and sleeve 172 described above. In such a situation, the tool 170" is placed over the bone screw receiver 10 top surfaces 50 with the bit 180" bottom surface 181" leading into the channel formed by the receiver inner arm surfaces 58. The guide wire, if any, may also be received through the drive tool 170" inner through bore 183" by threading the wire into the through bore at the bottom 181" of the tool bit 180" and out the top 178". With specific reference to FIG. 32, the tool 170" outer cylindrical surface 186" is received between the receiver arms 52 and the bit 180" is inserted into the insert drive 132. The tool 170" is now ready to rotate the shank 6 into the vertebra (not shown) over the guide wire. Disassembly of the tool 170" is accomplished in reverse order to the procedure described herein for assembly.

With reference to FIGS. 1 and 34-40, the rod 21 is eventually positioned in an open or percutaneous manner in cooperation with the at least two bone screw assemblies 1. The closure structure 18 is then inserted into and advanced between the arms 52 of each of the receivers 10. The closure structure 18 is rotated, using a tool engaged with the drive 165 until a selected pressure is reached at which point the domed bottom surface is in engagement with the rod outer surface 22, as shown, for example, in FIG. 34. At this time, the rod is captured between the closure 18 and the insert 14, but the insert 14 is slidable with respect to the receiver seating surface 40, resulting in the shank 6 being pivotable with respect to the rod in a single plane, shown in FIGS. 34-40 as a sagittal plane. For example, as vertebrae are manipulated during surgery, including, but not limited to contraction and distraction manipulations along the rod as well as rotational manipulations in the transverse plane, the bone screw assembly sliding insert 14 allows the bone screw shanks 6 to adjust in the sagittal plane. For example, FIG. 34 illustrates a bone screw in a neutral position. After manipulation, the bone screw assembly 1 may adjust as much as about twenty degrees cephalic as shown in FIG. 35 or as much as about twenty degrees caudal as shown in FIG. 36. Both FIGS. 37 and 38 show the assembly in a finally adjusted position that is about fifteen degrees caudal. FIG. 38 shows a final lock down of the closure 18 against the rod 21 wherein the frusto-conical surface 158 as well as portions of the interim surface 159 and domed surface 160 are in frictional engagement with the rod outer surface 22. At this time, the rod presses the insert bottom surface 120 into frictional engagement with the receiver seating surface 40, thus fixing the angle of the shank 6 (and also the vertebra attached to the shank 6) with respect to the rod 21.

If removal of the rod 21 from any of the bone screw assemblies 1 is necessary, or if it is desired to release the rod 21 at a particular location, disassembly is accomplished by using the driving tool (not shown) that mates with the internal drive 165 on the closure 18 to release the frictional engagement between the closure surfaces 158, 159 and 160 from the rod surface 22. Further disassembly may then be accomplished in reverse order to the procedure described previously herein for the assembly.

Figure 39:
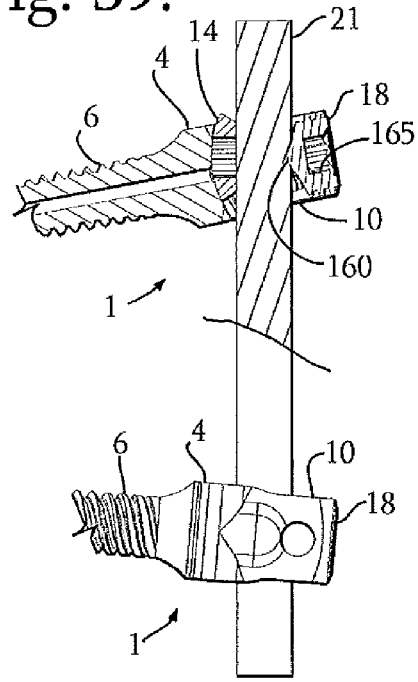
FIG. 39 is a partial side elevational view with portions broken away showing two bone screw assemblies of FIG. 1 attached to a rod, showing a kyphotic arrangement along the sagittal plane.
Figure 40:
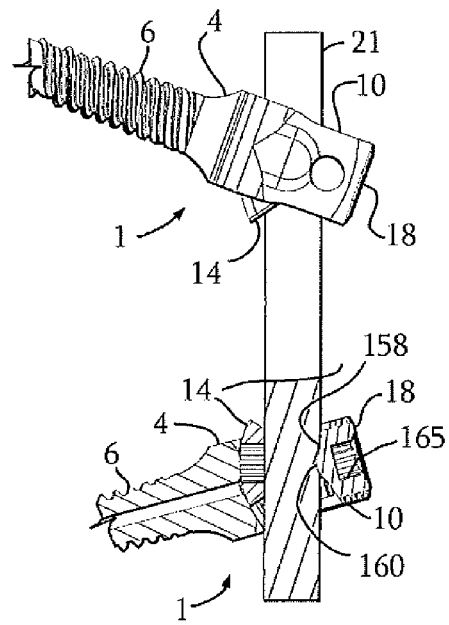
FIG. 40 is a partial side elevational view with portions broken away showing two bone screw assemblies of FIG. 1 attached to a rod, showing a lordotic arrangement along the sagittal plane.

With reference to FIGS. 39 and 40, in each figure, two bone screw assemblies 1 are shown with a rod 21 and after being allowed to adjust in response to spinal orientation. FIG. 39 illustrates a kyphotic arrangement of the two bone screws 1 along the sagittal plane and FIG. 40 illustrates a lordotic arrangement of the two bone screws 1 along the sagittal plane.

Figure 41:
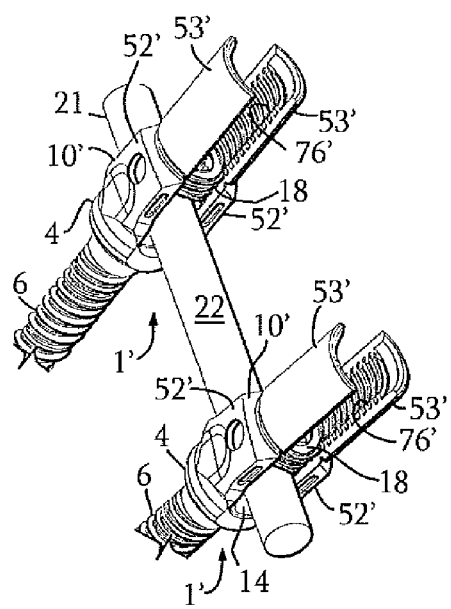
FIG. 41 is a partial perspective view showing two alternative bone screw assemblies of FIG. 1 attached to a rod, each of the screws including upper break-off tabs to support rod reduction.

FIG. 41 illustrates two bone screw assemblies 1', each assembled with a rod 21 and a closure 18. Each assembly 1' is identical to the assembly 1 previously described herein with the exception that each bone screw 10' of the assembly 1' further includes a pair of opposed break-off tabs or extensions 53', each extension 53' integral with a respective receiver arm 52' and having inner guide and advancement structure 76' that helically winds along an inner surface of each extension 53' and attached receiver arm 52'. The break-off extensions 53' aid in the assembly step of reducing the rod 21 into the bone screw receivers 10' by rotating the closures 18' downwardly through the extensions and into the receiver arms 52' while abutting against the rod 21. FIG. 41 illustrates the assemblies 1' at a stage just prior to the extensions 53' being broken off of the receiver arms 52'.

Figure 42:
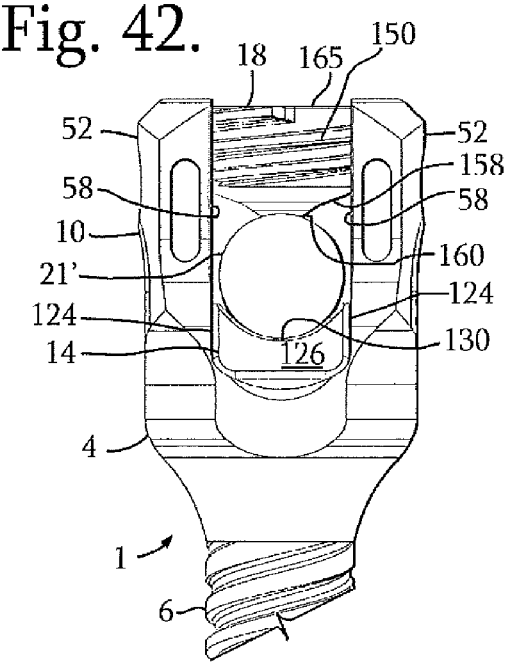
FIG. 42 is an enlarged and partial front elevational view of the bone screw assembly of FIG. 1 assembled with an alternative rod in lieu of the rod shown in FIG. 1, the alternative rod having a smaller diameter (5.5 mm) than a diameter (6.0 mm) of the rod shown in FIG. 1.

FIG. 42 illustrates the bone screw assembly 1 assembled with a rod 21' that has a diameter smaller than the rod 21 shown in the other figures. The insert 14 rod receiving surface 130 adequately aligns the smaller rod 21' within the receiver 10 when the closure 18 pressed down on the rod 21'.

It is to be understood that while certain forms of the present invention have been illustrated and described herein, it is not to be limited to the specific forms or arrangement of parts described and shown.

What is claimed and desired to be secured by Letters Patent is as follows:

1. In a spinal implant with a bone screw having a shank for implanting into bone, the bone screw capturing a longitudinal connecting member at an adjustable angle with respect to the shank, the improvement comprising:
   a) a receiver having a pair of spaced upstanding arms forming a channel for receiving the longitudinal connecting member, the receiver being integral with the shank, the receiver forming a cavity communicating with the channel, the cavity partially defined by a curved seating surface having a first radius, the receiver further having an arcuate pivot track formed in an inner surface of one of the upstanding arms, the pivot track being spaced from the seating surface, the pivot track having a second radius, the second radius originating at a pivot axis disposed perpendicular to and intersecting with a central axis of rotation of the shank; and
   b) an insert having a bottom curved surface sized and shaped for slidable engagement with the receiver seating surface, a projection in slidable engagement with the pivot track and a top surface sized and shaped for closely receiving the longitudinal connecting member.

2. The improvement of claim 1 further comprising a closure having a first guide and advancement structure for mating engagement with a second guide and advancement structure located on the receiver arms, the closure having a frusto-conical lower surface and a domed bottom surface located adjacent to the lower surface, the domed bottom surface being in engagement with the longitudinal connecting member during an interim adjustment stage of assembly allowing slidable movement of the insert with respect to the receiver, at least one of the domed bottom surface and the frusto-conical surface being in fixed frictional engagement with the longitudinal connecting member when the closure is rotated downwardly in the receiver into a final assembled position wherein the longitudinal connecting member is in fixed frictional engagement with both the insert and the closure structure, the insert also being in fixed frictional engagement with the receiver.

3. The improvement of claim 2 wherein the closure first guide and advancement structure is a multi-start form.

4. The improvement of claim 3 wherein the multi-start form in a flange form.

5. The improvement of claim 1 wherein the receiver seating surface first radius also originates at the pivot axis.

6. The improvement of claim 1 wherein the pivot axis is located at a top surface of the receiver and runs in a direction from one upstanding arm to the other upstanding arm.

7. The improvement of claim 1 wherein the receiver pivot track is in the form of first and second opposed arcuate apertures formed in the inner surfaces of the receiver arms and the insert has first and second opposed projections, each projection located in one of the apertures.

8. The improvement of claim 7 wherein the receiver arms have first and second opposed grooves each running parallel to the central axis, the first groove communicates with the first arcuate aperture and the second groove communicates with the second arcuate aperture, the first and second grooves sized and shaped to receive the respective first and second projections of the insert during assembly of the insert with the receiver.

9. The improvement of claim 8 further comprising first and second inwardly directed surface portions, the first surface portion located at an intersection of the first groove and the first aperture and the second surface portion located at an intersection of the second groove and the second aperture, the surface portions retaining the insert projections within the first and second apertures during sliding pivotal adjustment of the insert with respect to the receiver.

10. The improvement of claim 1 wherein the receiver opposed upstanding arms each have an integral break-off extension.

11. The improvement of claim 1 wherein the receiver has an inwardly directed stop and during assembly of the insert with the receiver, the insert projection must be forced against and pressed to a position beyond the stop prior to being in sliding engagement with the pivot track, the stop capturing the insert projection in the pivot track.

12. The improvement of claim 11 wherein the insert is top loaded into the receiver with the projection insertable into a groove formed in the receiver arm, the groove running parallel to the shank axis.

13. The improvement of claim 1 wherein the insert has a drive structure sized and shaped for receiving a bit of a drive tool.

14. The improvement of claim 13 further comprising a two piece drive tool having an inner portion with the drive bit for engaging the insert drive structure and a second outer portion fixable to the receiver arms.

15. The improvement of claim 13 wherein the insert drive structure is an aperture formed in the insert top surface.

16. The improvement of claim 15 wherein the insert drive feature extends through the insert.

17. The improvement of claim 1 wherein the receiver curved seating surface having a first radius is a first seating surface sized and shaped for receiving the insert and further comprising a second seating surface located adjacent the first seating surface, the second seating surface sized and shaped for receiving a portion of the longitudinal connecting member.

18. The improvement of claim 17 wherein the second seating surface slopes downwardly in a direction of the shank and outwardly away from the first seating surface.

19. The improvement of claim 17 wherein the second seating surface is a pair of opposed seating surfaces located on either side of the first seating surface.

20. A spinal bone screw pivotable with respect to a longitudinal connecting member in a single plane, the bone screw comprising:
   a) a shank having a thread;
   b) a receiver having a pair of spaced upstanding arms forming a channel for receiving the longitudinal connecting member, the receiver being integral with the shank, the receiver forming a cavity communicating with the channel, the receiver arms having opposed inner surfaces with opposed arcuate grooves, the grooves each defined in part by a radius originating at a pivot axis disposed perpendicular to and intersecting with a central axis of rotation of the shank; and
   c) a discrete insert located within the receiver cavity, the insert having a pair of opposed outwardly extending projections, each projection located within one of the arcuate grooves, the insert projections being slidable in the arcuate grooves, the insert having a seating surface in fixed, frictional engagement with the longitudinal connecting member.

21. The bone screw of claim 20 wherein the insert has a bottom surface and the receiver has a curved surface partially defining the receiver cavity, the bottom surface being in sliding engagement with the curved surface until the insert is pressed into fixed frictional engagement with the curved surface by a force pressing the longitudinal connecting member against the insert seating surface.

22. The bone screw of claim 20 further comprising a closure having a first guide and advancement structure for mating engagement with a second guide and advancement structure located on the receiver arms, the closure having a sloping lower surface and a partially spherical bottom surface located adjacent to the lower surface, the bottom surface being in engagement with the longitudinal connecting member during an interim adjustment stage of assembly allowing slidable movement of the insert with respect to the bone screw, at least one of the bottom surface and the lower surface being in fixed frictional engagement with the longitudinal connecting member when the closure is rotated downwardly in the receiver into a final assembled position wherein the longitudinal connecting member is in fixed frictional engagement with both the insert and the closure, the insert also being in fixed frictional engagement with the receiver.

23. The bone screw of claim 20 wherein the receiver has a pair of opposed inwardly directed stops and wherein during assembly of the insert with the receiver, the insert projections are forced against and pressed beyond the stops to a position within the arcuate grooves, the stops capturing the insert projections in the arcuate grooves.

24. A spinal bone screw pivotable in a single plane with respect to a longitudinal connecting member in the form of a rod, the bone screw comprising:
  a) a shank having a thread;
  b) a receiver having a pair of spaced upstanding arms forming a channel sized and shaped for receiving the rod, the receiver being integral with the shank, the receiver forming a cavity communicating with the channel, the cavity partially defined by a bottom partially cylindrical surface having a first radius, the receiver arms having opposed inner planar surfaces, each planar surface having an arcuate aperture communicating with an elongate groove, each groove being parallel to a central axis of rotation of the shank, each arcuate aperture being evenly spaced from the receiver bottom surface; and
  c) a discrete insert located within the receiver cavity, the insert having a bottom surface in sliding engagement with the receiver bottom surface, the insert further having a pair of outwardly extending projections, each projection located within one of the receiver arcuate apertures, the insert projections being captured in the receiver apertures, the insert having an upper seating surface sized and shaped for receiving and frictionally engaging the rod.

25. The bone screw of claim 24 wherein the receiver has first and second nubs located in the respective first and second grooves, each nub partially obstructing a path of the insert projection through the respective groove, the nubs capturing the insert projections in the receiver arcuate apertures.

26. A spinal bone screw pivotable with respect to a longitudinal connecting member in a single plane, the bone screw comprising:
  a) a shank having a thread;
  b) a receiver having a pair of spaced upstanding arms forming a channel for receiving the longitudinal connecting member, the receiver being integral with the shank, the receiver forming a cavity communicating with the channel, the cavity partially defined by a bottom surface having a first radius, the radius originating at a pivot axis disposed perpendicular to and intersecting with a central axis of rotation of the shank; and
  c) a discrete insert captured within the receiver cavity, the insert having a bottom surface with a second radius in slidable engagement with the receiver bottom surface, the second radius being substantially equal to the first radius, the insert having a top surface sized and shaped for frictional engagement with the longitudinal connecting member.

27. The bone screw of claim 26 further comprising a closure having a first guide and advancement structure for mating engagement with a second guide and advancement structure located on the receiver arms, the closure having a frusto-conical lower surface and a partially spherical bottom surface located adjacent to the lower surface, the bottom surface being in engagement with the longitudinal connecting member during an interim adjustment stage of assembly allowing slidable movement of the insert with respect to the bone screw, at least one of the bottom surface and the lower surface being in fixed frictional engagement with the longitudinal connecting member when the closure is rotated downwardly in the receiver into a final assembled position wherein the longitudinal connecting member is in fixed frictional engagement with both the insert and the closure, the insert also being in fixed frictional engagement with the receiver.

28. The bone screw of claim 26 wherein the receiver arms have arcuate apertures and the insert has a pair of opposed outwardly extending projections, the projections being captured within the apertures.

29. The bone screw of claim 26 wherein the receiver cavity is further defined by a rod receiving surface disposed at an angle to the receiver bottom surface that.

* * * * *